US009102729B2

(12) United States Patent
Masignani et al.

(10) Patent No.: US 9,102,729 B2
(45) Date of Patent: Aug. 11, 2015

(54) POLYPEPTIDES FROM NON-TYPEABLE HAEMOPHILUS INFLUENZAE

(71) Applicant: Novartis Vaccines and Diagnostics SRL, Siena (IT)

(72) Inventors: Vega Masignani, Siena (IT); Beatrice Maria Arico, Siena (IT)

(73) Assignee: Novartis Vaccines and Diagnostics SRL, Emeryville, CA (US)

( * ) Notice: Subject to any disclaimer, the term of this patent is extended or adjusted under 35 U.S.C. 154(b) by 0 days.

(21) Appl. No.: 14/264,972

(22) Filed: Apr. 29, 2014

(65) Prior Publication Data

US 2014/0234363 A1    Aug. 21, 2014

Related U.S. Application Data

(60) Division of application No. 13/357,394, filed on Jan. 24, 2012, now abandoned, which is a division of application No. 12/800,898, filed on May 25, 2010, now Pat. No. 8,124,098, which is a continuation of application No. 11/596,557, filed as application No. PCT/IB2005/001775 on May 16, 2005, now Pat. No. 7,749,518.

(30) Foreign Application Priority Data

May 14, 2004 (GB) .................................. 04108668

(51) Int. Cl.
  *A61K 39/102* (2006.01)
  *C07K 14/285* (2006.01)
  *A61K 39/00* (2006.01)

(52) U.S. Cl.
  CPC ............ *C07K 14/285* (2013.01); *A61K 39/102* (2013.01); *A61K 39/00* (2013.01); *A61K 2039/505* (2013.01); *A61K 2039/53* (2013.01)

(58) Field of Classification Search
  CPC ................... A61K 2039/505; A61K 2039/53; A61K 39/00; C07K 14/285
  See application file for complete search history.

(56) References Cited

U.S. PATENT DOCUMENTS 7,241,867 B2   7/2007   Bakaletz

FOREIGN PATENT DOCUMENTS

| WO | WO 91/01146 A1 | 2/1991 |
|----|----------------|--------|
| WO | WO 99/11241 A1 | 3/1999 |
| WO | WO 99/44636 A2 | 9/1999 |
| WO | WO 99/52549 A1 | 10/1999 |
| WO | WO 00/07621 A2 | 2/2000 |
| WO | WO 00/23105 A2 | 4/2000 |
| WO | WO 00/56360 A2 | 9/2000 |
| WO | WO 01/21152 A1 | 3/2001 |
| WO | WO 01/21207 A2 | 3/2001 |
| WO | WO 02/28889 A2 | 4/2002 |
| WO | WO 0234768 | 5/2002 |
| WO | WO 02/083723 A | 10/2002 |
| WO | WO 03/076575 A2 | 9/2003 |
| WO | WO 2004/078949 A | 9/2004 |
| WO | WO 2006/138527 A2 | 12/2006 |
| WO | WO 2007/084053 A1 | 7/2007 |

OTHER PUBLICATIONS

Brusic, et al., "Prediction of MHC Class II-Binding Peptides Using an Evolutionary Algorithm and Artificial Neural Network," *Bioinformatics* 14(2):121-130 (1998).
Carter, "Epitope Mapping of a Protein Using the Geysen (PEPSCAN) Procedure," *Metheds in Molecular Biology* vol. 36: *Peptide Analysis Protocols*, Dunn & Pennington, Eds., Humana Press, Totowa, NJ, pp. 207-223 (1994).
Davenport, et al., "An Empirical Method for the Prediction of T-Cell Epitopes," *Immunogenetics* 42:392-397 (1995).
De Lalla, et al., "Cutting Edge: Identification of Novel T Cell Epitopes in Lol p5a by Computational Prediction," *J Immunol* 163:1725-1729 (1999).
Erdile, et al., "Role of Attached Lipid in Immunogenicity of *Borrelia Burgdorfei* OspA," *Inf Immun* 61(1):81-90 (1993).
Feller, et al., "Identifying Antigenic T-Cell Sites," *Nature* 349:720-721 (1991).
Fleischmann, et al., "Whole-Genome Random Sequencing and Assembly of *Haemophilus influenzae* Rd," *Science* 296:496-512 (1995).
Genbank Accession No. NC_000907, "*Haemophilus influenzae* RD KW20,".
Geysen, et al., "Use of Peptide Synthesis to Probe Viral Antigens for Epitopes to a Resolution of a Single Amino Acid," *PNAS USA* 81:3998-4002 (1984).
Hopp, et al., "Retrospective: 12 Years of Antigenic Determinant Predictions, and More," *Peptide Res* 6(4):183-190 (1993).
Jameson, et al., "The Antigenic Index: A Novel Algorithm for Predicting Antigenic Determinants," *Cabios* 4(1):181-186 (1988).
Li, et al., "Identification and Characterization of Genomic Loci Unique to the Brazilian Purpuric Fever Clonal Group of *H. influenzae* Biogroup Aegyptiud: Functionality Explored Using Meningococcal Homology," *Mol Microbiol* 47(4):1101-1111 (2003).
Maksyutov, et al., "ADEPT: A Computer Program for Prediction of Protein Antigenic Determinants," *Cabios* 9(3):291-297 (1993).
Mason, et al., "Nontypable *Haemophilus influenzae* Gene Expression Induced in Vivo in a *Chinchilla* Model of Otitis Media," *Inf Immun* 71(6):3454-3462 (2003).
McMicheal, "Vaccines for *Moraxella catarrhalis*," *Vaccine* 19:s101-s107 (2001).

(Continued)

*Primary Examiner* — Padma V Baskar
(74) *Attorney, Agent, or Firm* — Robins Law Group; Roberta L. Robins

(57) ABSTRACT

Polypeptides comprising non-typeable *Haemophilus influenzae* (NTHi) amino acid sequences. Over 2500 specific NTHi proteins are disclosed. The invention also provides related polypeptides, nucleic acids, antibodies and methods. These can all be used in medicine for treating or preventing disease and/or infection caused by *H. influenzae*, such as otitis media.

15 Claims, No Drawings

(56) References Cited

OTHER PUBLICATIONS

Meister, et al., "Two Novel T Cell Epitope Prediction Algorithms Based on MHC-Binding Motifs; Comparison of Predicted and Published Epitopes From Myocobacterium Tuberculosis and HIV Protein Sequences," *Vaccine* 13(6):581-591 (1995).

Needleman, et al., "A General Method Applied to the Search for Similarities in the Amino Acid Sequence of Two Proteins," *J Mol Biol* 48:443-453 (1970).

Raddrizzani, et al., "Epitope Scanner Using Virtual Matrix-Based Algorithms," *Breifings in Bioinformatics* 1(2):179-189 (2000).

Rice, et al., "EMBOSS: The European Molecular Biology Open Software Suite," *Trends Genet* 16:276-277 (2000).

Roberts, et al., "Prediction of HIV Peptide Epitopes by a Novel Alforithm," *AIDS Res Hum Retroviruses* 12(7):593-610 (1996).

Singhi, et al., "Evaluation of Polymerase Chain Reaction (PCR) for Diagnosing *Haemophilus influenzae* B Meningitis," *Ann Trop Microbiol* 37(3):190-195 (2003).

Welling, et al., "Prediction of Sequential Antigenic Regions in Proteins," *FEBS* 188(2):215-218 (1985).

Yadav, et al., "Rapid Detection of *Haemophius influenzae* by Hel Gene Polymerase Chain Reaction," *Lett Applied Microbiol* 37:190-195 (2003).

Lederman et al., *Molecular Immunology* 28:1171-1181 (1991).

Li et al., *Proc. Natl. Acad. Sci.* 77:3211-3214 (1980).

Accession No. G86194 (Date: Mar. 2, 2001).

Greenspan et al., Nature Biotechnology, 7:936-937 (1999).

Houghton et al., (Vaccines, 1986, Edited by Fred Brown: Cold Spring Harbor Laboratory).

Accession No. H64038, Aug. 18, 1995.

POLYPEPTIDES FROM NON-TYPEABLE HAEMOPHILUS INFLUENZAE

CROSS-REFERENCE TO RELATED APPLICATIONS

This application is a divisional of U.S. patent application Ser. No. 13/357,394, filed Jan. 24, 2012, now abandoned, which is a divisional of U.S. patent application Ser. No. 12/800,898, filed May 25, 2010, now U.S. Pat. No. 8,124,098, which is a continuation of U.S. patent application Ser. No. 11/596,557, filed Feb. 14, 2008, now U.S. Pat. No. 7,749,518, which is a 371 of PCT/IB05/01775, filed May 16, 2005, and claims priority to United Kingdom patent application no. 0410866.8, filed May 14, 2004, from which applications priority is claimed pursuant to 35 U.S.C. §§119/120 and which applications are incorporated herein by reference in their entireties.

INCORPORATION BY REFERENCE OF MATERIAL ON COMPACT DISC

This application incorporates by reference the Sequence Listing contained on the two compact discs (Copy 1 and Copy 2), filed concurrently herewith, containing the following file:

File name: PP022930.0003 SequenceList.txt; created Nov. 10, 2006; 6,676 KB in size.

TECHNICAL FIELD

This invention is in the field of *Haemophilus influenzae* immunology and vaccinology.

BACKGROUND ART

*Haemophilus influenzae* is a small, non-motile, Gram-negative coccobacillus. It is a respiratory pathogen that causes a wide spectrum of human infections, including: asymptomatic colonization of the upper respiratory tract (i.e. carriage); infections that extend from colonized mucosal surfaces to cause otitis media (inflammation of the middle ear), bronchitis, conjunctivitis, sinusitis, urinary tract infections and pneumonia; and invasive infections, such as bacteremia, septic arthritis, epiglottitis, pneumonia, empyema, pericarditis, cellulitis, osteomyelitis and meningitis. *H. influenzae* was the first bacterium for which a complete genome sequence was published [1].

*H. influenzae* strains are either capsulated (typeable) or non-capsulated (non-typeable), and there are six major serological types of capsulated strains (a to f). 95% of *H. influenzae*-caused invasive diseases are caused by *H. influenzae* type b ('Hib') strains. The most serious manifestation of Hib disease is meningitis, but the introduction in the 1980s of vaccines based on conjugated Hib capsular saccharides has hugely reduced incidence of this disease.

Although Hib infections can now be controlled by vaccination, other pathogenic *H. influenzae* strains remain a risk. For instance, non-typeable *H. influenzae* (NTHi) is responsible for otitis media (OM), particularly chronic OM. While OM is rarely associated with mortality, it is associated with significant morbidity. Hearing loss is the most common complication of OM, with behavioral, educational and language development delays being additional consequences of early onset OM with effusion. Acute OM is the most common bacterial infection in children in the USA. The non-typeable *H. influenzae* biogroup aegyptius causes epidemic conjunctivitis and Brazilian purpuric fever (BPF) [2], with BPF having a mortality of up to 70%.

To date, antibiotics are the main tool against the spectrum of clinical entities known collectively as OM, but widespread use of antibiotics for OM has met with controversy due to the emergence of multiple-antibiotic resistant microorganisms. Progress towards a vaccine is slow due to an incomplete understanding of both the pathogenesis of OM and the immune response to it.

The genome sequence of the serotype d strain KW20 [1,3] has been useful for understanding basic *H. influenzae* biology, but it has not been so useful in countering pathogenic *H. influenzae* strains, as serotype d strains are generally not pathogens.

It is an object of the invention to provide polypeptides for use in the development of vaccines for preventing and/or treating infections caused by non-typeable *H. influenzae* strains. In particular, it is an object to provide polypeptides for use in improved vaccines for preventing and/or treating otitis media. The polypeptides may also be useful for diagnostic purposes, and as targets for antibiotics.

DISCLOSURE OF THE INVENTION

Polypeptides

The invention provides polypeptides comprising the *H. influenzae* amino acid sequences disclosed in the examples. These amino acid sequences are the even SEQ ID NOs between 2 and 5080. There are thus 2540 amino acid sequences, and these are referred to as NTHnnnn, where nnnn is a number between 0001 and 2832 (there are 292 NTHnnnn numbers that have no sequence; see Table I). Further NTHi sequences of the invention are given as SEQ ID NOS: 5088 onwards.

The invention also provides polypeptides comprising amino acid sequences that have sequence identity to the *H. influenzae* amino acid sequences disclosed in the examples. Depending on the particular sequence, the degree of sequence identity is preferably greater than 50% (e.g. 60%, 70%, 75%, 80%, 85%, 90%, 91%, 92%, 93%, 94%, 95%, 96%, 97%, 98%, 99% or more). These polypeptides include homologs, orthologs, allelic variants and functional mutants. Typically, 50% identity or more between two polypeptide sequences is considered to be an indication of functional equivalence. Identity between polypeptides is preferably determined by the Smith-Waterman homology search algorithm as implemented in the MPSRCH program (Oxford Molecular), using an affine gap search with parameters gap open penalty=12 and gap extension penalty=1.

These polypeptide may, compared to the NTHi sequences of the examples, include one or more (e.g. 1, 2, 3, 4, 5, 6, 7, 8, 9, 10, etc.) conservative amino acid replacements i.e. replacements of one amino acid with another which has a related side chain. Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cystine, serine, threonine, tyrosine. Phenylalanine, tryptophan, and tyrosine are sometimes classified jointly as aromatic amino acids. In general, substitution of single amino acids within these families does not have a major effect on the biological activity. The polypeptides may also include one or more (e.g. 1, 2, 3, 4, 5, 6, 7, 8, 9, 10, etc.) single amino acid deletions relative to the NTHi sequences of the examples. The polypeptides may also include one or more (e.g. 1, 2, 3, 4, 5, 6, 7, 8, 9, 10, etc.) insertions (e.g. each of 1, 2, 3, 4 or 5 amino acids) relative to the NTHi sequences of the examples.

Preferred polypeptides of the invention are listed in Table II, including polypeptides that are lipidated, that are located in the outer membrane, that are located in the inner membrane, that are located in the periplasm, or that are not found in non-pathogenic *H. influenzae* strains. Particularly preferred polypeptides are those that fall into more than one of these categories e.g. polypeptides that are located in the outer membrane and are also not found in non-pathogenic *H. influenzae* strains.

A particularly preferred polypeptide is NTH0867. NTH0861, NTH0863 and NTH0865 are also preferred. As described below, these four proteins are embodied by SEQ ID NOS: 1566, 5095, 1570, 5094, 1574, 5093, 1578 and 5092. Within these eight SEQ ID NOS, 1566-1578 are preferred.

The invention further provides polypeptides comprising fragments of the *H. influenzae* amino acid sequences disclosed in the examples. The fragments should comprise at least n consecutive amino acids from the sequences and, depending on the particular sequence, n is 7 or more (e.g. 8, 10, 12, 14, 16, 18, 20, 22, 24, 26, 28, 30, 35, 40, 45, 50, 60, 70, 80, 90, 100 or more).

The fragment may comprise at least one T-cell or, preferably, a B-cell epitope of the sequence. T- and B-cell epitopes can be identified empirically (e.g. using PEPSCAN [4,5] or similar methods), or they can be predicted (e.g. using the Jameson-Wolf antigenic index [6], matrix-based approaches [7], TEPITOPE [8], neural networks [9], OptiMer & EpiMer [10, 11], ADEPT [12], Tsites [13], hydrophilicity [14], antigenic index [15] or the methods disclosed in reference 16 etc.). Other preferred fragments are (a) the N-terminal signal peptides of the NTHi polypeptides of the invention, (b) the NTHi polypeptides, but without their N-terminal signal peptides, (c) the NTHi polypeptides, but without their N-terminal amino acid residue.

Polypeptides of the invention can be prepared in many ways e.g. by chemical synthesis (in whole or in part), by digesting longer polypeptides using proteases, by translation from RNA, by purification from cell culture (e.g. from recombinant expression), from the organism itself (e.g. after bacterial culture, or direct from patients), etc. A preferred method for production of peptides<40 amino acids long involves in vitro chemical synthesis [17,18]. Solid-phase peptide synthesis is particularly preferred, such as methods based on tBoc or Fmoc [19] chemistry. Enzymatic synthesis [20] may also be used in part or in full. As an alternative to chemical synthesis, biological synthesis may be used e.g. the polypeptides may be produced by translation. This may be carried out in vitro or in vivo.

Biological methods are in general restricted to the production of polypeptides based on L-amino acids, but manipulation of translation machinery (e.g. of aminoacyl tRNA molecules) can be used to allow the introduction of D-amino acids (or of other non natural amino acids, such as iodotyrosine or methylphenylalanine, azidohomoalanine, etc.) [21]. Where D-amino acids are included, however, it is preferred to use chemical synthesis. Polypeptides of the invention may have covalent modifications at the C-terminus and/or N-terminus.

Polypeptides of the invention can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.).

Polypeptides of the invention are preferably provided in purified or substantially purified form i.e. substantially free from other polypeptides (e.g. free from naturally-occurring polypeptides), particularly from other *Haemophilus* or host cell polypeptides, and are generally at least about 50% pure (by weight), and usually at least about 90% pure i.e. less than about 50%, and more preferably less than about 10% (e.g. 5%) of a composition is made up of other expressed polypeptides.

Polypeptides of the invention are preferably *H. influenzae* polypeptides. Polypeptides of the invention preferably have the function indicated in Table III for the relevant sequence.

Polypeptides of the invention may be attached to a solid support. Polypeptides of the invention may comprise a detectable label (e.g. a radioactive or fluorescent label, or a biotin label).

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can occur as single chains or associated chains. Polypeptides of the invention can be naturally or non-naturally glycosylated (i.e. the polypeptide has a glycosylation pattern that differs from the glycosylation pattern found in the corresponding naturally occurring polypeptide).

The invention provides polypeptides comprising a sequence —X—Y— or —Y—X—, wherein: —X— is an amino acid sequence as defined above and —Y— is not a sequence as defined above i.e. the invention provides fusion proteins. Where the N-terminus codon of a polypeptide-coding sequence is not ATG then that codon will be translated as the standard amino acid for that codon rather than as a Met, which occurs when the codon is a start codon.

The invention provides a process for producing polypeptides of the invention, comprising the step of culturing a host cell of to the invention under conditions which induce polypeptide expression.

The invention provides a process for producing a polypeptide of the invention, wherein the polypeptide is synthesised in part or in whole using chemical means.

The invention provides a composition comprising two or more polypeptides of the invention.

The invention also provides a hybrid polypeptide represented by the formula $NH_2$-A-[-X-L-]$_n$-B—COOH, wherein X is a polypeptide of the invention as defined above, L is an optional linker amino acid sequence, A is an optional N-terminal amino acid sequence, B is an optional C-terminal amino acid sequence, and n is an integer greater than 1. The value of n is between 2 and x, and the value of x is typically 3, 4, 5, 6, 7, 8, 9 or 10. Preferably n is 2, 3 or 4; it is more preferably 2 or 3; most preferably, n=2. For each n instances, —X— may be the same or different. For each n instances of [—X-L-], linker amino acid sequence -L- may be present or absent. For instance, when n=2 the hybrid may be $NH_2$—$X_1$-$L_1$-$X_2$-$L_2$-COOH, $NH_2$—$X_1$—$X_2$—COOH, $NH_2$—$X_1$-$L_1$-$X_2$—COOH, $NH_2$—$X_1$—$X_2$-$L_2$-COOH, etc. Linker amino acid sequence(s) -L- will typically be short (e.g. 20 or fewer amino acids i.e. 19, 18, 17, 16, 15, 14, 13, 12, 11, 10, 9, 8, 7, 6, 5, 4, 3, 2, 1). Examples include short peptide sequences which facilitate cloning, poly-glycine linkers (i.e. Gly$_n$ where n=2, 3, 4, 5, 6, 7, 8, 9, 10 or more), and histidine tags (i.e. His$_n$ where n=3, 4, 5, 6, 7, 8, 9, 10 or more). Other suitable linker amino acid sequences will be apparent to those skilled in the art. -A- and —B— are optional sequences which will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct polypeptide trafficking, or short peptide sequences which facilitate cloning or purification (e.g. histidine tags i.e. His$_n$ where n=3, 4, 5, 6, 7, 8, 9, 10 or more). Other suitable N-terminal and C-terminal amino acid sequences will be apparent to those skilled in the art.

Various tests can be used to assess the in vivo immunogenicity of polypeptides of the invention. For example, polypeptides can be expressed recombinantly and used to screen patient sera by immunoblot. A positive reaction between the polypeptide and patient serum indicates that the patient has previously mounted an immune response to the protein in question i.e. the protein is an immunogen. This method can also be used to identify immunodominant proteins.

Antibodies

The invention provides antibodies that bind to polypeptides of the invention. These may be polyclonal or monoclonal and may be produced by any suitable means (e.g. by recombinant expression). To increase compatibility with the human immune system, the antibodies may be chimeric or humanised [e.g. refs. 22 & 23], or fully human antibodies may be used. The antibodies may include a detectable label (e.g. for diagnostic assays). Antibodies of the invention may be attached to a solid support. Antibodies of the invention are preferably neutralizing antibodies.

Monoclonal antibodies are particularly useful in identification and purification of the individual polypeptides against which they are directed. Monoclonal antibodies of the invention may also be employed as reagents in immunoassays, radioimmunoassays (RIA) or enzyme-linked immunosorbent assays (ELISA), etc. In these applications, the antibodies can be labelled with an analytically-detectable reagent such as a radioisotope, a fluorescent molecule or an enzyme. The monoclonal antibodies produced by the above method may also be used for the molecular identification and characterization (epitope mapping) of polypeptides of the invention.

Antibodies of the invention are preferably provided in purified or substantially purified form. Typically, the antibody will be present in a composition that is substantially free of other polypeptides e.g. where less than 90% (by weight), usually less than 60% and more usually less than 50% of the composition is made up of other polypeptides.

Antibodies of the invention can be of any isotype (e.g. IgA, IgG, IgM i.e. an α, γ or μ heavy chain), but will generally be IgG. Within the IgG isotype, antibodies may be IgG1, IgG2, IgG3 or IgG4 subclass. Antibodies of the invention may have a κ or a λ light chain.

Antibodies of the invention can take various forms, including whole antibodies, antibody fragments such as F(ab')2 and F(ab) fragments, Fv fragments (non-covalent heterodimers), single-chain antibodies such as single chain Fv molecules (scFv), minibodies, oligobodies, etc. The term "antibody" does not imply any particular origin, and includes antibodies obtained through non-conventional processes, such as phage display.

The invention provides a process for detecting polypeptides of the invention, comprising the steps of: (a) contacting an antibody of the invention with a biological sample under conditions suitable for the formation of an antibody-antigen complexes; and (b) detecting said complexes.

The invention provides a process for detecting antibodies of the invention, comprising the steps of (a) contacting a polypeptide of the invention with a biological sample (e.g. a blood or serum sample) under conditions suitable for the formation of an antibody-antigen complexes; and (b) detecting said complexes.

Nucleic Acids

The invention provides nucleic acid comprising the *H. influenzae* nucleotide sequences disclosed in the examples. These nucleic acid sequences are the odd SEQ ID NOs between 1 and 5080.

The invention also provides nucleic acid comprising nucleotide sequences having sequence identity to the *H. influenzae* nucleotide sequences disclosed in the examples. Identity between sequences is preferably determined by the Smith-Waterman homology search algorithm as described above.

The invention also provides nucleic acid which can hybridize to the *H. influenzae* nucleic acid disclosed in the examples. Hybridization reactions can be performed under conditions of different "stringency". Conditions that increase stringency of a hybridization reaction of widely known and published in the art [e.g. page 7.52 of reference 24]. Examples of relevant conditions include (in order of increasing stringency): incubation temperatures of 25° C., 37° C., 50° C., 55° C. and 68° C.; buffer concentrations of 10×SSC, 6×SSC, 1×SSC, 0.1× SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or de-ionized water. Hybridization techniques and their optimization are well known in the art [e.g. see references 24-27, etc.].

In some embodiments, nucleic acid of the invention hybridizes to a target of the invention under low stringency conditions; in other embodiments it hybridizes under intermediate stringency conditions; in preferred embodiments, it hybridizes under high stringency conditions. An exemplary set of low stringency hybridization conditions is 50° C. and 10×SSC. An exemplary set of intermediate stringency hybridization conditions is 55° C. and 1×SSC. An exemplary set of high stringency hybridization conditions is 68° C. and 0.1×SSC.

Nucleic acid comprising fragments of these sequences are also provided. These should comprise at least n consecutive nucleotides from the *H. influenzae* sequences and, depending on the particular sequence, n is 10 or more (e.g. 12, 14, 15, 18, 20, 25, 30, 35, 40, 50, 60, 70, 80, 90, 100, 150, 200 or more).

The invention provides nucleic acid of formula 5'-X—Y—Z-3', wherein: —X— is a nucleotide sequence consisting of x nucleotides; —Z— is a nucleotide sequence consisting of z nucleotides; —Y— is a nucleotide sequence consisting of either (a) a fragment of one of the odd-numbered SEQ ID NOS: 1 to 5079, or (b) the complement of (a); and said nucleic acid 5'-X—Y—Z-3' is neither (i) a fragment of one of the odd-numbered SEQ ID NOS: 1 to 5079 nor (ii) the complement of (i). The —X— and/or —Z— moieties may comprise a promoter sequence (or its complement).

The invention also provides nucleic acid encoding the polypeptides and polypeptide fragments of the invention.

The invention includes nucleic acid comprising sequences complementary to the sequences disclosed in the sequence listing (e.g. for antisense or probing, or for use as primers), as well as the sequences in the orientation actually shown.

Nucleic acids of the invention can be used in hybridisation reactions (e.g. Northern or Southern blots, or in nucleic acid microarrays or 'gene chips') and amplification reactions (e.g. PCR, SDA, SSSR, LCR, TMA, NASBA, etc.) and other nucleic acid techniques.

Nucleic acid according to the invention can take various forms (e.g. single-stranded, double-stranded, vectors, primers, probes, labelled etc.). Nucleic acids of the invention may be circular or branched, but will generally be linear. Unless otherwise specified or required, any embodiment of the invention that utilizes a nucleic acid may utilize both the double-stranded form and each of two complementary single-stranded forms which make up the double-stranded form. Primers and probes are generally single-stranded, as are antisense nucleic acids.

Nucleic acids of the invention are preferably provided in purified or substantially purified form i.e. substantially free from other nucleic acids (e.g. free from naturally-occurring nucleic acids), particularly from other *Haemophilus* or host cell nucleic acids, generally being at least about 50% pure (by weight), and usually at least about 90% pure. Nucleic acids of the invention are preferably *H. influenzae* nucleic acids.

Nucleic acids of the invention may be prepared in many ways e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases), from genomic or cDNA libraries, etc.

Nucleic acid of the invention may be attached to a solid support (e.g. a bead, plate, filter, film, slide, microarray support, resin, etc.). Nucleic acid of the invention may be labelled e.g. with a radioactive or fluorescent label, or a biotin label. This is particularly useful where the nucleic acid is to be used in detection techniques e.g. where the nucleic acid is a primer or as a probe.

The term "nucleic acid" includes in general means a polymeric form of nucleotides of any length, which contain deoxyribonucleotides, ribonucleotides, and/or their analogs. It includes DNA, RNA, DNA/RNA hybrids. It also includes DNA or RNA analogs, such as those containing modified backbones (e.g. peptide nucleic acids (PNAs) or phosphorothioates) or modified bases. Thus the invention includes mRNA, tRNA, rRNA, ribozymes, DNA, cDNA, recombinant nucleic acids, branched nucleic acids, plasmids, vectors, probes, primers, etc. Where nucleic acid of the invention takes the form of RNA, it may or may not have a 5' cap.

Nucleic acids of the invention comprise NTHi sequences, but they may also comprise non-NTHi sequences (e.g. in nucleic acids of formula 5'-X—Y—Z-3', as defined above). This is particularly useful for primers, which may thus comprise a first sequence complementary to a PCAV nucleic acid target and a second sequence which is not complementary to the nucleic acid target. Any such non-complementary sequences in the primer are preferably 5' to the complementary sequences. Typical non-complementary sequences comprise restriction sites or promoter sequences.

Nucleic acids of the invention can be prepared in many ways e.g. by chemical synthesis (at least in part), by digesting longer nucleic acids using nucleases (e.g. restriction enzymes), by joining shorter nucleic acids (e.g. using ligases or polymerases), from genomic or cDNA libraries, etc.

Nucleic acids of the invention may be part of a vector i.e. part of a nucleic acid construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, "viral vectors" which is designed to result in the production of a recombinant virus or virus-like particle, or "shuttle vectors", which comprise the attributes of more than one type of vector. Preferred vectors are plasmids. A "host cell" includes an individual cell or cell culture which can be or has been a recipient of exogenous nucleic acid. Host cells include progeny of a single host cell, and the progeny may not necessarily be completely identical (in morphology or in total DNA complement) to the original parent cell due to natural, accidental, or deliberate mutation and/or change. Host cells include cells transfected or infected in vivo or in vitro with nucleic acid of the invention.

Where a nucleic acid is DNA, it will be appreciated that "U" in a RNA sequence will be replaced by "T" in the DNA. Similarly, where a nucleic acid is RNA, it will be appreciated that "T" in a DNA sequence will be replaced by "U" in the RNA.

The term "complement" or "complementary" when used in relation to nucleic acids refers to Watson-Crick base pairing. Thus the complement of C is G, the complement of G is C, the complement of A is T (or U), and the complement of T (or U) is A. It is also possible to use bases such as I (the purine inosine) e.g. to complement pyrimidines (C or T). The terms also imply a direction—the complement of 5'-ACAGT-3' is 5'-ACTGT-3' rather than 5'-TGTCA-3'.

Nucleic acids of the invention can be used, for example: to produce polypeptides; as hybridization probes for the detection of nucleic acid in biological samples; to generate additional copies of the nucleic acids; to generate ribozymes or antisense oligonucleotides; as single-stranded DNA primers or probes; or as triple-strand forming oligonucleotides.

The invention provides a process for producing nucleic acid of the invention, wherein the nucleic acid is synthesised in part or in whole using chemical means.

The invention provides vectors comprising nucleotide sequences of the invention (e.g. cloning or expression vectors) and host cells transformed with such vectors.

The invention also provides a kit comprising primers (e.g. PCR primers) for amplifying a template sequence contained within a *Haemophilus* bacterium (e.g. *H. influenzae*) nucleic acid sequence, the kit comprising a first primer and a second primer, wherein the first primer is substantially complementary to said template sequence and the second primer is substantially complementary to a complement of said template sequence, wherein the parts of said primers which have substantial complementarity define the termini of the template sequence to be amplified. The first primer and/or the second primer may include a detectable label (e.g. a fluorescent label).

The invention also provides a kit comprising first and second single-stranded oligonucleotides which allow amplification of a *Haemophilus* template nucleic acid sequence contained in a single- or double-stranded nucleic acid (or mixture thereof), wherein: (a) the first oligonucleotide comprises a primer sequence which is substantially complementary to said template nucleic acid sequence; (b) the second oligonucleotide comprises a primer sequence which is substantially complementary to the complement of said template nucleic acid sequence; (c) the first oligonucleotide and/or the second oligonucleotide comprise(s) sequence which is not compementary to said template nucleic acid; and (d) said primer sequences define the termini of the template sequence to be amplified. The non-complementary sequence(s) of feature (c) are preferably upstream of (i.e. 5' to) the primer sequences. One or both of these (c) sequences may comprise a restriction site [e.g. ref.28] or a promoter sequence [e.g. 29].

The first oligonucleotide and/or the second oligonucleotide may include a detectable label (e.g. a fluorescent label).

The template sequence may be any part of a genome sequence.

The invention provides a process for detecting nucleic acid of the invention, comprising the steps of: (a) contacting a nucleic probe according to the invention with a biological sample under hybridising conditions to form duplexes; and (b) detecting said duplexes.

The invention provides a process for detecting *H. influenzae* in a biological sample (e.g. blood), comprising the step of contacting nucleic acid according to the invention with the biological sample under hybridising conditions. The process may involve nucleic acid amplification (e.g. PCR, SDA, SSSR, LCR, TMA, NASBA, etc.) or hybridisation (e.g. microarrays, blots, hybridisation with a probe in solution etc.). PCR detection of *H. influenzae* in clinical samples has been reported [e.g. see refs. 30 & 31]. Clinical assays based on nucleic acid are described in general in ref. 32.

The invention provides a process for preparing a fragment of a target sequence, wherein the fragment is prepared by extension of a nucleic acid primer. The target sequence and/or the primer are nucleic acids of the invention. The primer extension reaction may involve nucleic acid amplification (e.g. PCR, SDA, SSSR, LCR, TMA, NASBA, etc.).

Nucleic acid amplification according to the invention may be quantitative and/or real-time.

For certain embodiments of the invention, nucleic acids are preferably at least 7 nucleotides in length (e.g. 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 90, 100, 110, 120, 130, 140, 150, 160, 170, 180, 190, 200, 225, 250, 275, 300 nucleotides or longer).

For certain embodiments of the invention, nucleic acids are preferably at most 500 nucleotides in length (e.g. 450, 400, 350, 300, 250, 200, 150, 140, 130, 120, 110, 100, 90, 80, 75, 70, 65, 60, 55, 50, 45, 40, 39, 38, 37, 36, 35, 34, 33, 32, 31, 30, 29, 28, 27, 26, 25, 24, 23, 22, 21, 20, 19, 18, 17, 16, 15 nucleotides or shorter).

Primers and probes of the invention, and other nucleic acids used for hybridization, are preferably between 10 and 30 nucleotides in length (e.g. 10, 11, 12, 13, 14, 15, 16, 17, 18, 19, 20, 21, 22, 23, 24, 25, 26, 27, 28, 29, or 30 nucleotides).

Pharmaceutical Compositions

The invention provides compositions comprising: (a) polypeptide, antibody, and/or nucleic acid of the invention; and (b) a pharmaceutically acceptable carrier. These compositions may be suitable as immunogenic compositions, for instance, or as diagnostic reagents, or as vaccines. Vaccines according to the invention may either be prophylactic (i.e. to prevent infection) or therapeutic (i.e. to treat infection), but will typically be prophylactic.

A 'pharmaceutically acceptable carriers' includes any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in ref. 138.

Compositions of the invention may include an antimicrobial, particularly if packaged in a multiple dose format.

Compositions of the invention may comprise detergent e.g. a Tween (polysorbate), such as Tween 80. Detergents are generally present at low levels e.g. <0.01%.

Compositions of the invention may include sodium salts (e.g. sodium chloride) to give tonicity. A concentration of 10±2 mg/ml NaCl is typical.

Compositions of the invention will generally include a buffer. A phosphate buffer is typical.

Compositions of the invention may comprise a sugar alcohol (e.g. mannitol) or a disaccharide (e.g. sucrose or trehalose) e.g. at around 15-30 mg/ml (e.g. 25 mg/ml), particularly if they are to be lyophilised or if they include material which has been reconstituted from lyophilised material. The pH of a composition for lyophilisation may be adjusted to around 6.1 prior to lyophilisation.

Polypeptides of the invention may be administered in conjunction with other immunoregulatory agents. In particular, compositions will usually include a vaccine adjuvant. Adjuvants which may be used in compositions of the invention include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 33], or mixtures of different mineral compounds, with the compounds taking any suitable form (e.g. gel, crystalline, amorphous, etc.), and with adsorption being preferred. The mineral containing compositions may also be formulated as a particle of metal salt [34].

Aluminium phosphates are particularly preferred, particularly in compositions which include a *H. influenzae* saccharide antigen, and a typical adjuvant is amorphous aluminium hydroxyphosphate with $PO_4$/Al molar ratio between 0.84 and 0.92, included at 0.6 mg $Al^{3+}$/ml. Adsorption with a low dose of aluminium phosphate may be used e.g. between 50 and 100 µg $Al^{3+}$ per conjugate per dose. Where there is more than one conjugate in a composition, not all conjugates need to be adsorbed.

B. Oil Emulsions

Oil emulsion compositions suitable for use as adjuvants in the invention include squalene-water emulsions, such as MF59 [Chapter 10 of ref 33; see also ref. 35] (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

C. Saponin Formulations [Chapter 22 of Ref 33]

Saponin formulations may also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref 36. Saponin formulations may also comprise a sterol, such as cholesterol [37].

Combinations of saponins and cholesterols can be used to form unique particles called immunostimulating complexes (ISCOMs) [chapter 23 of ref 33]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 37-39. Optionally, the ISCOMS may be devoid of additional detergent [40].

A review of the development of saponin based adjuvants can be found in refs. 41 & 42.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 43-48. Virosomes are discussed further in, for example, ref 49

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 50. Such "small particles" of 3dMPL are small enough to be sterile filtered through a 0.22 µm membrane [50]. Other non-toxic LPS derivatives include monophosphoryl lipid A mimics, such as aminoalkyl glucosaminide phosphate derivatives e.g. RC-529 [51,52].

Lipid A derivatives include derivatives of lipid A from *Escherichia coli* such as OM-174. OM-174 is described for example in refs. 53 & 54.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 55, 56 and 57 disclose possible analog substitutions e.g. replacement of guanosine with 2'-deoxy-7-deazaguanosine. The adjuvant effect of CpG oligonucleotides is further discussed in refs. 58-63.

The CpG sequence may be directed to TLR9, such as the motif GTCGTT or TTCGTT [64]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 65-67. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 64 & 68-70.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 71 and as parenteral adjuvants in ref. 72. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 73-80. Numerical reference for amino acid substitutions is preferably based on the alignments of the A and B subunits of ADP-ribosylating toxins set forth in ref. 81, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [82], etc.) [83], interferons (e.g. interferon-γ), macrophage colony stimulating factor, and tumor necrosis factor.

G. Bioadhesives and Mucoadhesives

Bioadhesives and mucoadhesives may also be used as adjuvants in the invention. Suitable bioadhesives include esterified hyaluronic acid microspheres [84] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [85].

H. Microparticles

Microparticles may also be used as adjuvants in the invention. Microparticles (i.e. a particle of ~100 nm to ~150 µm in diameter, more preferably ~200 nm to ~30 µm in diameter, and most preferably ~500 nm to ~10 µm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref 33)

Examples of liposome formulations suitable for use as adjuvants are described in refs. 86-88.

J. Polyoxyethylene Ether and Polyoxyethylene Ester Formulations

Adjuvants suitable for use in the invention include polyoxyethylene ethers and polyoxyethylene esters [89]. Such formulations further include polyoxyethylene sorbitan ester surfactants in combination with an octoxynol [90] as well as polyoxyethylene alkyl ethers or ester surfactants in combination with at least one additional non-ionic surfactant such as an octoxynol [91]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 92 and 93.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquamod and its homologues (e.g. "Resiquimod 3M"), described further in refs. 94 and 95.

The invention may also comprise combinations of aspects of one or more of the adjuvants identified above. For example, the following adjuvant compositions may be used in the invention: (1) a saponin and an oil-in-water emulsion [96]; (2) a saponin (e.g. QS21)+a non-toxic LPS derivative (e.g. 3dMPL) [97]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [98]; (5) combinations of 3dMPL with, for example, QS21 and/or oil-in-water emulsions [99]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 33.

The use of an aluminium hydroxide or aluminium phosphate adjuvant is particularly preferred, and antigens are generally adsorbed to these salts. Calcium phosphate is another preferred adjuvant.

The pH of compositions of the invention is preferably between 6 and 8, preferably about 7. Stable pH may be maintained by the use of a buffer. Where a composition comprises an aluminium hydroxide salt, it is preferred to use a histidine buffer [100]. The composition may be sterile and/or pyrogen-free. Compositions of the invention may be isotonic with respect to humans.

Compositions may be presented in vials, or they may be presented in ready-filled syringes. The syringes may be supplied with or without needles. A syringe will include a single dose of the composition, whereas a vial may include a single dose or multiple doses. Injectable compositions will usually be liquid solutions or suspensions. Alternatively, they may be presented in solid form (e.g. freeze-dried) for solution or suspension in liquid vehicles prior to injection.

Compositions of the invention may be packaged in unit dose form or in multiple dose form. For multiple dose forms, vials are preferred to pre-filled syringes. Effective dosage volumes can be routinely established, but a typical human dose of the composition for injection has a volume of 0.5 ml.

Where a composition of the invention is to be prepared extemporaneously prior to use (e.g. where a component is presented in lyophilised form) and is presented as a kit, the kit may comprise two vials, or it may comprise one ready-filled syringe and one vial, with the contents of the syringe being used to reactivate the contents of the vial prior to injection.

Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials, and a typical quantity of each meningococcal saccharide antigen per dose is between 1 μg and 10 mg per antigen.

Pharmaceutical Uses

The invention also provides a method of treating a patient, comprising administering to the patient a therapeutically effective amount of a composition of the invention. The patient may either be at risk from the disease themselves or may be a pregnant woman ('maternal immunisation').

The invention provides nucleic acid, polypeptide, or antibody of the invention for use as medicaments (e.g. as immunogenic compositions or as vaccines) or as diagnostic reagents. It also provides the use of nucleic acid, polypeptide, or antibody of the invention in the manufacture of: (i) a medicament for treating or preventing disease and/or infection caused by *H. influenzae*; (ii) a diagnostic reagent for detecting the presence of *H. influenzae* or of antibodies raised against *H. influenzae*; and/or (iii) a reagent which can raise antibodies against *H. influenzae*. Said *H. influenzae* can be any serotype or strain, but is preferably a non-typeable *H. influenzae*. Said disease may be, for instance, otitis media (including acute otitis media), bronchitis, conjunctivitis, sinusitis, a urinary tract infection, pneumonia, bacteremia, septic arthritis, epiglottitis, pneumonia, empyema, pericarditis, cellulitis, osteomyelitis, lower respiratory tract infection or meningitis. The invention is particularly useful for preventing inflammation of the middle ear, by eliciting an immune response that prevents bacteria from moving from the throat to the middle ear via the eustachian tube, where the middle ear is then colonised.

The patient is preferably a human. Where the vaccine is for prophylactic use, the human is preferably a child (e.g. a toddler or infant); where the vaccine is for therapeutic use, the human is preferably an adult. A vaccine intended for children may also be administered to adults e.g. to assess safety, dosage, immunogenicity, etc.

One way of checking efficacy of therapeutic treatment involves monitoring NTHi infection after administration of the composition of the invention. One way of checking efficacy of prophylactic treatment involves monitoring immune responses against an administered polypeptide after administration. Immunogenicity of compositions of the invention can be determined by administering them to test subjects (e.g. children 12-16 months age, or animal models [e.g. a chinchilla model [146]) and then determining standard parameters including ELISA titres (GMT) of IgG. These immune responses will generally be determined around 4 weeks after administration of the composition, and compared to values determined before administration of the composition.

Where more than one dose of the composition is administered, more than one post-administration determination may be made.

Administration of polypeptide antigens is a preferred method of treatment for inducing immunity. Administration of antibodies of the invention is another preferred method of treatment. This method of passive immunisation is particularly useful for newborn children or for pregnant women. This method will typically use monoclonal antibodies, which will be humanised or fully human.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

Bacterial infections affect various areas of the body and so compositions may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition). The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. refs 101 & 102].

Combinations

Within the >2500 proteins described in the examples, NTH0861, NTH0863, NTH0865 and NTH0867 are particularly preferred for use with the invention (particularly in vaccines), and these four proteins can be used in combinations. Thus the invention provides a composition comprising: (a) a NTH0861 protein; and (b) at least one further NTHi protein. The invention also provides a composition comprising: (a) a NTH0863 protein; and (b) at least one further NTHi protein. The invention also provides a composition comprising: (a) a NTH0865 protein; and (b) at least one further NTHi protein. The invention also provides a composition comprising: (a) a NTH0867 protein; and (b) at least one further NTHi protein. The further NTHi protein can be selected from proteins of the invention as described above.

The combinations are preferably selected within these four proteins, and so the invention provides a composition comprising two or more (i.e. 2, 3 or 4) of NTH0861, NTH0863, NTH0865 and/or NTH0867. Preferred compositions comprise: (1) NTH0861 and NTH0863; (2) NTH0861 and NTH0865; (3) NTH0861 and NTH0867; (4) NTH0863 and NTH0865; (5) NTH0863 and NTH0867; (6) NTH0865 and NTH0867; (7) NTH0861, NTH0863 and NTH0865; (8) NTH0861, NTH0863 and NTH0867; (9) NTH0863, NTH0865 and NTH0867; (10) NTH0861, NTH0865 and NTH0867; (11) NTH0861, NTH0863, NTH0865 and NTH0867.

The NTH0861 protein preferably comprises SEQ ID NO: 1566, SEQ ID NO: 5095, or an amino acid sequence having sequence identity (as described above) to SEQ ID NO: 1566 and/or to SEQ ID NO: 5095. The NTH0863 protein preferably comprises SEQ ID NO: 1570, SEQ ID NO: 5094, or an amino acid sequence having sequence identity (as described above) to SEQ ID NO: 1570 and/or to SEQ ID NO: 5094. The NTH0865 protein preferably comprises SEQ ID NO: 1574, SEQ ID NO: 5093, or an amino acid sequence having sequence identity (as described above) to SEQ ID NO: 1574 and/or to SEQ ID NO: 5093. The NTH0867 protein preferably comprises SEQ ID NO: 1578, SEQ ID NO: 5092, or an amino acid sequence having sequence identity (as described above) to SEQ ID NO: 1578 and/or to SEQ ID NO: 5092.

Further Antigenic Components of Compositions of the Invention

The invention also provides a composition comprising a polypeptide or the invention and one or more of the following further antigens:

a saccharide antigen from *N. meningitidis* serogroup A, C, W135 and/or Y (preferably all four), such as the oligosaccharide disclosed in ref. 103 from serogroup C [see also ref. 104] or the oligosaccharides of ref. 105.

a saccharide antigen from *Streptococcus pneumoniae* [e.g. 106, 107, 108].

an antigen from hepatitis A virus, such as inactivated virus [e.g. 109, 110].

an antigen from hepatitis B virus, such as the surface and/or core antigens [e.g. 110, 111].

a diphtheria antigen, such as a diphtheria toxoid [e.g. chapter 3 of ref. 112] e.g. the $CRM_{197}$ mutant [e.g. 113].

a tetanus antigen, such as a tetanus toxoid [e.g. chapter 4 of ref. 112].

an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 114 & 115].

a saccharide antigen from *Haemophilus influenzae* B [e.g. 104].

polio antigen(s) [e.g. 116, 117] such as IPV.

measles, mumps and/or rubella antigens [e.g. chapters 9, 10 & 11 of ref. 112].

influenza antigen(s) [e.g. chapter 19 of ref. 112], such as the haemagglutinin and/or neuraminidase surface proteins.

an antigen from *Moraxella catarrhalis* [e.g. 118].

an protein antigen from *Streptococcus agalactiae* (group B *streptococcus*) [e.g. 119, 120].

a saccharide antigen from *Streptococcus agalactiae* (group B *streptococcus*).

an antigen from *Streptococcus pyogenes* (group A *streptococcus*) [e.g. 120, 121, 122].

an antigen from *Staphylococcus aureus* [e.g. 123].

The composition may comprise one or more of these further antigens.

Toxic protein antigens may be detoxified where necessary (e.g. detoxification of pertussis toxin by chemical and/or genetic means [115]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. DTP combinations are thus preferred.

Saccharide antigens are preferably in the form of conjugates. Carrier proteins for the conjugates include diphtheria toxin, tetanus toxin, the *N. meningitidis* outer membrane protein [124], synthetic peptides [125,126], heat shock proteins [127,128], pertussis proteins [129,130], protein D from *H. influenzae* [131], cytokines [132], lymphokines [132], streptococcal proteins, hormones [132], growth factors [132], toxin A or B from *C. difficile* [133], iron-uptake proteins [134], etc. A preferred carrier protein is the CRM197 diphtheria toxoid [135].

Antigens in the composition will typically be present at a concentration of at least 1 µg/ml each. In general, the concentration of any given antigen will be sufficient to elicit an immune response against that antigen.

As an alternative to using proteins antigens in the immunogenic compositions of the invention, nucleic acid (preferably DNA e.g. in the form of a plasmid) encoding the antigen may be used.

Antigens are preferably adsorbed to an aluminium salt.

Screening Methods

The invention provides a process for determining whether a test compound binds to a polypeptide of the invention. If a test compound binds to a polypeptide of the invention and this binding inhibits the life cycle of the *H. influenzae* bacterium, then the test compound can be used as an antibiotic or as a lead compound for the design of antibiotics. The process will typically comprise the steps of contacting a test compound with a polypeptide of the invention, and determining whether the test compound binds to said polypeptide. Preferred polypeptides of the invention for use in these processes are enzymes (e.g. tRNA synthetases), membrane transporters and ribosomal polypeptides. Suitable test compounds include polypeptides, polypeptides, carbohydrates, lipids, nucleic acids (e.g. DNA, RNA, and modified forms thereof), as well as small organic compounds (e.g. MW between 200 and 2000 Da). The test compounds may be provided individually, but will typically be part of a library (e.g. a combinatorial library). Methods for detecting a binding interaction include NMR, filter-binding assays, gel-retardation assays, displacement assays, surface plasmon resonance, reverse two-hybrid etc. A compound which binds to a polypeptide of the invention can be tested for antibiotic activity by contacting the compound with GBS bacteria and then monitoring for inhibition of growth. The invention also provides a compound identified using these methods.

Preferably, the process comprises the steps of: (a) contacting a polypeptide of the invention with one or more candidate compounds to give a mixture; (b) incubating the mixture to allow polypeptide and the candidate compound(s) to interact; and (c) assessing whether the candidate compound binds to the polypeptide or modulates its activity.

Once a candidate compound has been identified in vitro as a compound that binds to a polypeptide of the invention then it may be desirable to perform further experiments to confirm the in vivo function of the compound in inhibiting bacterial growth and/or survival. Thus the method comprise the further step of contacting the compound with a NTHi bacterium and assessing its effect.

The polypeptide used in the screening process may be free in solution, affixed to a solid support, located on a cell surface or located intracellularly. Preferably, the binding of a candidate compound to the polypeptide is detected by means of a label directly or indirectly associated with the candidate compound. The label may be a fluorophore, radioisotope, or other detectable label.

General

The invention provides a computer-readable medium (e.g. a floppy disk, a hard disk, a CD-ROM, a DVD etc.) and/or a computer memory and/or a computer database containing one or more of the sequences in the sequence listing.

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

The N-terminus residues in the amino acid sequences in the sequence listing are given as the amino acid encoded by the first codon in the corresponding nucleotide sequence. Where the first codon is not ATG, it will be understood that it will be translated as methionine when the codon is a start codon, but will be translated as the indicated non-Met amino acid when the sequence is at the C-terminus of a fusion partner. The invention specifically discloses and encompasses each of the amino acid sequences of the sequence listing having a N-terminus methionine residue (e.g. a formyl-methionine residue) in place of any indicated non-Met residue.

Alternative start codons can be used in biology. The amino acid sequences in the sequence listing are based on particular start codons, but downstream start codons may alternatively be used. Thus the invention specifically discloses and encompasses each of the amino acid sequences of the sequence listing, starting at any methionine residue from the sequence that is downstream of the N-terminal residue shown in the sequence listing (e.g. SEQ ID NOS: 5088, 5089 & 5090).

As indicated in the above text, nucleic acids and polypeptides of the invention may include sequences that:

(a) are identical (i.e. 100% identical) to the sequences disclosed in the sequence listing;

(b) share sequence identity with the sequences disclosed in the sequence listing;

(c) have 1, 2, 3, 4, 5, 6, 7, 8, 9 or 10 single nucleotide or amino acid alterations (deletions, insertions, substitutions), which may be at separate locations or may be contiguous, as compared to the sequences of (a) or (b); and (d) when aligned with a particular sequence from the sequence listing using a pairwise alignment algorithm, a moving window of x monomers (amino acids or nucleotides) moving from start (N-terminus or 5') to end (C-terminus of 3'), such that for an alignment that extends to p monomers (where p>x) there are p−x+1 such windows, each window has at least x·y identical aligned monomers, where: x is selected from 20, 25, 30, 35, 40, 45, 50, 60, 70, 80, 90, 100, 150, 200; y is selected from 0.50, 0.60, 0.70, 0.75, 0.80, 0.85, 0.90, 0.91, 0.92, 0.93, 0.94, 0.95, 0.96, 0.97, 0.98, 0.99; and if x·y is not an integer then it is rounded up to the nearest integer. The preferred pairwise alignment algorithm is the Needleman-Wunsch global alignment algorithm [136], using default parameters (e.g. with Gap opening penalty=10.0, and with Gap extension penalty=0.5, using the EBLOSUM62 scoring matrix). This algorithm is conveniently implemented in the needle tool in the EMBOSS package [137].

The nucleic acids and polypeptides of the invention may additionally have further sequences to the N-terminus/5' and/or C-terminus/3' of these sequences (a) to (d).

The practice of the present invention will employ, unless otherwise indicated, conventional methods of chemistry, biochemistry, molecular biology, immunology and pharmacology, within the skill of the art. Such techniques are explained fully in the literature. See, e.g., references 138-145, etc.

MODES FOR CARRYING OUT THE INVENTION

Genome sequencing has been carried out on a low-passage clinical NTHi isolate (strain 86-028NP [146]). A total of 2540 coding sequences were identified in the genome, and these are given in the sequence listing together with their inferred translation products. Annotation of 1489 of the polypeptide sequences is given in Table III. From the sequenced material, polypeptide-coding sequences of particular interest were selected for further work, with particular attention to immunogenic proteins for vaccine development.

Lipoproteins

Of the 2540 coding sequences, the following 39 were identified as lipoproteins: NTH0094, NTH10163, NTH0167, NTH0255, NTH0289, NTH-0838, NTH-0909, NTH0997, NTH1000, NTH1016, NTH11174, NTH1298, NTH1313, NIH1413, NIH1416, NTH1552, NTH1623, NIH1675, NIH1680, NTH1739, NTH1873, NTH1922, NTH1942, NIH1974, NTH2142, NTH2169, NTH2251, NTH2349, NTH2356, NTH2358, NTH2524, NTH2588, NTH2595, NTH2641, NTH2673, NTH2715, NIH2754, NTH2758, and NTH2769. Lipoproteins are surface-exposed and, as such, they represent accessible immunological targets e.g. for diagnostic and for immunisation purposes. Moreover, it has been found in *B. burgdorferi* [147] that OspA protein is immunogenic in a lipidated form but is non-immunogenic in a non-lipidated form, and the authors concluded that post-translational lipid attachment is a critical determinant of OspA immunogenicity.

Outer Membrane

As *H. influenzae* is a Gram-negative bacterium, its cell wall includes an outer membrane. Of the 2540 coding sequences, the following 48 were identified as being located in this outer membrane: NTH0017, NTH0193, NTH0227, NTH0241, NTH0252, NTH0270, NTH0432, NTH0498, NTH0502, NTH0504, NTH0512, NTH0539, NTH0638, NTH0647, NTH0648, NTH0788, NTH0839, NTH0867, NTH0914, NTH1054, NTH1075, NTH1082, NTH1200, NTH1203, NTH1214, NTH1290, NTH1390, NTH1582, NTH1652, NTH1666, NTH1744, NTH1819, NTH1845, NTH1900, NTH1953, NTH1956, NTH1958, NTH1962, NTH2039, NTH2232, NTH2234, NTH2235, NTH2269, NTH2448, NTH2484, NTH2493, and NTH2727. Outer membrane proteins (OMPs) are surface-exposed and, as such, they represent accessible immunological targets e.g. for diagnostic and for immunisation purposes. OMPs are often invasins, adhesins, etc. which, if blocked, offers a means of preventing bacterial infection.

NTH1845 is an Aida-like autotransporter ('Lav') and is a preferred protein of the invention. It is conserved between NTHi strains, including one known to cause meningitis, but there is no corresponding gene in the Rd sequence or in strain R2846. It lies between the tmk and holb genes. A preferred form of NTH1845 starts at Met-22 (i.e. SEQ ID NO: 5090).

Periplasm

As *H. influenzae* is a Gram-negative bacterium, it has a periplasm between its cell cytoplasmic membrane and its outer membrane. Of the 2540 coding sequences, the following 105 were identified as being located in the periplasm: NTH0014, NTH1049, NTH0057, NTH0059, NTH0106, NTH0119, NTH0120, NTH0132, NTH0174, NTH0190, NTH0206, NTH0244, NTH0346, NTH0405, NTH0421, NTH0468, NTH0485, NTH0513, NTH0547, NTH0619, NTH0643, NTH0661, NTH0691, NTH0738, NTH0820, NTH0835, NTH0848, NTH0849, NTH0856, NTH0861, NTH0863, NTH0865, NTH0910, NTH0926, NTH0961, NTH1015, NTH1018, NTH1121, NTH1164, NTH1185, NTH1190, NTH1261, NTH1268, NTH1301, NTH1311, NTH1388, NTH1394, NTH1406, NTH1407, NTH1414, NTH1435, NTH1468, NTH1541, NTH1570, NTH1600, NTH1601, NTH1619, NTH1622, NTH1724, NTH1745, NTH1773, NTH1781, NTH1798, NTH1807, NTH1829, NTH1865, NTH1871, NTH1892, NTH1897, NTH1916, NTH1917, NTH1965, NTH1999, NTH2116, NTH2119, NTH2133, NTH2135, NTH2149, NTH2150, NTH2187, NTH2217, NTH2227, NTH2256, NTH2258, NTH2277, NTH2291, NTH2316, NTH2342, NTH2344, NTH2369, NTH2394, NTH2432, NTH2434, NTH2451, NTH2496, NTH2508, NTH2537, NTH2541, NTH2572, NTH2575, NTH2610, NTH2705, NTH2726, NTH2738, and NTH2778. Periplasmic proteins represent useful immunological targets e.g. for diagnostic and for immunisation purposes.

Inner Membrane

As *H. influenzae* is a Gram-negative bacterium, it has an inner membrane. Of the 2540 coding sequences, the following 740 were identified as being located in the inner membrane: NTH0002, NTH0015, NTH0019, NTH0020, NTH0021, NTH0025, NTH0032, NTH0034, NTH0035, NTH0041, NTH0043, NTH0045, NTH0048, NTH0050, NTH0052, NTH0060, NTH0061, NTH0067, NTH0073, NTH0076, NTH0085, NTH0089, NTH0091, NTH0097, NTH0107, NTH0110, NTH0116, NTH0118, NTH0121, NTH0128, NTH0134, NTH0135, NTH0151, NTH0155, NTH0157, NTH0158, NTH0180, NTH0184, NTH0185, NTH0186, NTH0189, NTH0199, NTH0203, NTH0208, NTH0209, NTH0223, NTH0224, NTH0228, NTH0232, NTH0237, NTH0238, NTH0242, NTH0247, NTH0248, NTH0251, NTH0253, NTH0254, NTH0256, NTH0263, NTH0269, NTH0278, NTH0279, NTH0280, NTH0290, NTH0295, NTH0297, NTH0302, NTH0307, NTH0311, NTH0317, NTH0320, NTH0321, NTH0325, NTH0326, NTH0333, NTH0334, NTH0341, NTH0347, NTH0351, NTH0352, NTH0353, NTH0356, NTH0358, NTH0366, NTH0371, NTH0372, NTH0388, NTH0397, NTH0400, NTH0401, NTH0402, NTH0407, NTH0411, NTH0412, NTH0417, NTH0418, NTH0420, NTH0426, NTH0427, NTH0434, NTH0435, NTH0437, NTH0444, NTH0453, NTH0455, NTH0457, NTH0459, NTH0460, NTH0461, NTH0462, NTH0463, NTH0465, NTH0469, NTH0473, NTH0475, NTH0478, NTH0484, NTH0489, NTH0490, NTH0493, NTH0496, NTH0507, NTH0509, NTH0518, NTH0524, NTH0526, NTH0528, NTH0529, NTH0544, NTH0545, NTH0549, NTH0565, NTH0566, NTH0574, NTH0580, NTH0581, NTH0584, NTH0585, NTH0586, NTH0587, NTH0590, NTH0617, NTH0618, NTH0622, NTH0624, NTH0626, NTH0630, NTH0636, NTH0637, NTH0642, NTH0644, NTH0646, NTH0654, NTH0656, NTH0658, NTH0673, NTH0675, NTH0676, NTH0677,
NTH0678, NTH0680, NTH01694, NTH0696, NTH0702,
NTH0703, NTH0706, NTH0709, NTH0710, NTH0712,
NTH0715, NTH0718, NTH0728, NTH0730, NTH0740,
NTH0744, NTH0745, NTH0749, NTH0750, NTH0755,
NTH0762, NTH0764, NTH0765, NTH0771, NTH0774,
NTH0794, NTH0795, NTH0796, NTH0797, NTH0798,
NTH0802, NTH0803, NTH0804, NTH0813, NTH0814,
NTH0815, NTH0821, NTH0822, NTH0827, NTH0829,
NTH0834, NTH0836, NTH850, NTH0851, NTH0852,
NTH0858, NTH0872, NTH0874, NTH0875, NTH0880,
NTH0887, NTH0888, NTH0894, NTH0904, NTH0913,
NTH0927, NTH0928, NTH0941, NTH0948, NTH0949,
NTH0950, NTH0952, NTH0953, NTH0955, NTH0964,
NTH0968, NTH0973, NTH0986, NTH0987, NTH0989,
NTH0994, NTH0996, NTH1002, NTH1003, NTH1004,
NTH1005, NTH1009, NTH1010, NTH1012, NTH1020,
NTH1021, NTH1026, NTH1028, NTH1031, NTH1032,
NTH1037, NTH1039, NTH1042, NTH1043, NTH1048,
NTH1052, NTH1058, NTH1063, NTH1064, NTH1069,
NTH1073, NTH1080, NTH1083, NTH1084, NTH1085,
NTH1086, NTH1087, NTH1089, NTH1090, NTH1091,
NTH1092, NTH1098, NTH1102, NTH1103, NTH1104,
NTH1106, NTH1123, NTH1124, NTH1125, NTH1130,
NTH1138, NTH1141, NTH1150, NTH1151, NTH1178,
NTH1181, NTH1184, NTH1188, NTH1189, NTH1191,
NTH1192, NTH1193, NTH1201, NTH1205, NTH1216,
NTH1220, NTH1221, NTH1224, NTH1225, NTH1226,
NTH1229, NTH1230, NTH1231, NTH1233, NTH1234,
NTH1236, NTH1238, NTH1240, NTH1241, NTH1250,
NTH1252, NTH1254, NTH1255, NTH1256, NTH1262,
NTH1273, NTH1275, NTH1279, NTH1280, NTH1281,
NTH1282, NTH1283, NTH1286, NTH1287, NTH1293,
NTH1295, NTH1297, NTH1300, NTH1302, NTH1305,
NTH1306, NTH1307, NTH1308, NTH1309, NTH1315,
NTH1319, NTH1321, NTH1327, NTH1332, NTH1334,
NTH1336, NTH1337, NTH1341, NTH1346, NTH1348,
NTH1354, NTH1357, NTH1359, NTH1363, NTH1365,
NTH1368, NTH1374, NTH1376, NTH1379, NTH1380,
NTH1383, NTH1391, NTH1393, NTH1398, NTH1400,
NTH1411, NTH1412, NTH1420, NTH1421, NTH1425,
NTH1427, NTH1428, NTH1429, NTH1430, NTH1431,
NTH1434, NTH1437, NTH1438, NTH1439, NTH1447,
NTH1448, NTH1450, NTH1454, NTH1455, NTH1464,
NTH1467, NTH1470, NTH1471, NTH1472, NTH1473,
NTH1474, NTH1479, NTH1491, NTH1492, NTH1493,
NTH1495, NTH1500, NTH1503, NTH1506, NTH1510,
NTH1515, NTH1525, NTH1526, NTH1527, NTH1528,
NTH1531, NTH1532, NTH1537, NTH1538, NTH1540,
NTH1548, NTH1559, NTH1562, NTH1567, NTH1569,
NTH1573, NTH1575, NTH1581, NTH1584, NTH1586,
NTH1587, NTH1588, NTH1590, NTH1594, NTH1597,
NTH1599, NTH1602, NTH1605, NTH1606, NTH1608,
NTH1609, NTH1617, NTH1618, NTH1620, NTH1621,
NTH1625, NTH1629, NTH1631, NTH1634, NTH1637,
NTH1638, NTH1653, NTH1654, NTH1657, NTH1662,
NTH1664, NTH1668, NTH1671, NTH1686, NTH1687,
NTH1688, NTH1689, NTH1690, NTH1692, NTH1693,
NTH1698, NTH1701, NTH1707, NTH1712, NTH1718,
NTH1719, NTH1722, NTH1725, NTH1729, NTH1732,
NTH1735, NTH1760, NTH1767, NTH1770, NTH1778,
NTH1779, NTH1782, NTH1783, NTH1788, NTH1793,
NTH1795, NTH1796, NTH1799, NTH1803, NTH1805,
NTH1806, NTH1813, NTH1815, NTH1820, NTH1824,
NTH1828, NTH1835, NTH1836, NTH1842, NTH1849,
NTH1850, NTH1859, NTH1861, NTH1870, NTH1872,
NTH1881, NTH1882, NTH1885, NTH1888, NTH1889,
NTH1891, NTH1896, NTH1898, NTH1899, NTH1906,
NTH1908, NTH1919, NTH1923, NTH1925, NTH1927,
NTH1935, NTH1939, NTH1941, NTH1951, NTH1960,
NTH1963, NTH1966, NTH1967, NTH1968, NTH1978,
NTH1981, NTH1986, NTH1992, NTH1993, NTH1995,
NTH1996, NTH1997, NTH1998, NTH2001, NTH2005,
NTH2008, NTH2009, NTH2010, NTH2024, NTH2025,
NTH2038, NTH2040, NTH2041, NTH2043, NTH2050,
NTH2052, NTH2055, NTH2060, NTH2062, NTH2064,
NTH2065, NTH2070, NTH2071, NTH2073, NTH2078,
NTH2079, NTH2081, NTH2083, NTH2089, NTH2091,
NTH2092, NTH2093, NTH2094, NTH2095, NTH2096,
NTH2097, NTH2099, NTH2101, NTH2112, NTH2115,
NTH2118, NTH2120, NTH2122, NTH2126, NTH2128,
NTH2129, NTH2130, NTH2131, NTH2136, NTH2138,
NTH2145, NTH2146, NTH2162, NTH2163, NTH2166,
NTH2169, NTH2170, NTH2173, NTH2181, NTH2183,
NTH2191, NTH2193, NTH2195, NTH2196, NTH2200,
NTH2204, NTH2205, NTH2209, NTH2213, NTH2226,
NTH2228, NTH2231, NTH2242, NTH2243, NTH2247,
NTH2250, NTH2253, NTH2257, NTH2259, NTH2262,
NTH2263, NTH2266, NTH2273, NTH2274, NTH2282,
NTH2284, NTH2285, NTH2288, NTH2292, NTH2296,
NTH2299, NTH2318, NTH2323, NTH2324, NTH2326,
NTH2327, NTH2333, NTH2343, NTH2346, NTH2347,
NTH2352, NTH2361, NTH2364, NTH2365, NTH2368,
NTH2370, NTH2371, NTH2376, NTH2377, NTH2381,
NTH2382, NTH2388, NTH2398, NTH2402, NTH2405,
NTH2406, NTH2407, NTH2408, NTH2414, NTH2422,
NTH2430, NTH2433, NTH2438, NTH2447, NTH2455,
NTH2457, NTH2458, NTH2472, NTH2478, NTH2481,
NTH2486, NTH2495, NTH2497, NTH2498, NTH2499,
NTH2501, NTH2505, NTH2525, NTH2531, NTH2532,
NTH2533, NTH2534, NTH2542, NTH2543, NTH2545,
NTH2546, NTH2548, NTH2549, NTH2550, NTH2552,
NTH2554, NTH2556, NTH2557, NTH2558, NTH2562,
NTH2566, NTH2567, NTH2568, NTH2569, NTH2570,
NTH2573, NTH2577, NTH2578, NTH2587, NTH2591,
NTH2593, NTH2597, NTH2600, NTH2602, NTH2603,
NTH2604, NTH2605, NTH2612, NTH2613, NTH2615,
NTH2616, NTH2618, NTH2626, NTH2633, NTH2640,
NTH2647, NTH2648, NTH2649, NTH2650, NTH2661,
NTH2663, NTH2664, NTH2667, NTH2668, NTH2674,
NTH2675, NTH2680, NTH2690, NTH2701, NTH2702,
NTH2703, NTH2708, NTH2711, NTH2724, NTH2725,
NTH2732, NTH2735, NTH2740, NTH2743, NTH2749,
NTH2750, NTH2755, NTH2756, NTH2757, NTH2764,
NTH2765, NTH2774, NTH2777, NTH2779, NTH2781,
NTH2793, NTH2794, NTH2796, NTH2797, NTH2798,
NTH2806, NTH2807, NTH2813, NTH2814, NTH2823, and
NTH2824. Inner membrane proteins represent useful immunological targets e.g. for diagnostic and for immunisation purposes.

Of these proteins, NTH1069 in particular has been identified as a virulence-associated protein. A preferred form of this protein starts at Met-27 (i.e. SEQ ID NO: 5088). Another preferred form starts at Met-19 (SEQ ID NO: 5089).

Adhesin

An adhesin having amino acid sequence SEQ ID NO: 5091 has been identified in a NTHi strain isolated from a patient with meningitis. It is homologous to the Hia adhesin from *N. meningitidis*.

*H. influenzae* Rd

The genome sequence of the serotype d strain KW20 [1,3] was published in 1995. As serotype d strains are generally not pathogens, but the sequenced NTHi strain is from a clinical infection, expressed NTHi sequences that are not seen in serotype d are likely to be the proteins that are involved in pathogenic mechanisms. Blocking these proteins, either by antibiotic treatment or by antibody binding, thus has therapeutic potential. Of the 2540 coding sequences, the following 613 are not seen in the Rd genome: NTH0001, NTH0002, NTH0004, NTH0005, NTH0012, NTH0016, NTH0021, NTH0022, NTH0024, NTH0032, NTH0033, NTH0034, NTH0035, NTH0036, NTH0037, NTH0038, NTH0040, NTH0045, NTH0050, NTH0051, NTH0052, NTH0053, NTH0064, NTH0089, NTH0092, NTH0097, NTH0101, NTH0104, NTH0110, NTH0114, NTH0122, NTH0123, NTH0124, NTH0125, NTH0129, NTH0135, NTH0136, NTH0138, NTH0140, NTH0146, NTH0148, NTH0151, NTH0153, NTH0154, NTH0159, NTH0161, NTH0164, NTH0169, NTH0173, NTH0176, NTH0177, NTH0187, NTH0191, NTH0192, NTH0193, NTH0194, NTH0195, NTH0197, NTH0198, NTH0199, NTH0226, NTH0235, NTH0236, NTH0238, NTH0250, NTH0251, NTH0254, NTH0255, NTH0256, NTH0264, NTH0265, NTH0278, NTH0279, NTH0280, NTH0282, NTH0283, NTH0284, NTH0285, NTH0289, NTH0297, NTH0298, NTH0299, NTH0300, NTH0302, NTH0307, NTH0308, NTH0312, NTH0313, NTH0319, NTH0327, NTH0328, NTH0331, NTH0334, NTH0335, NTH0339, NTH0341, NTH0348, NTH0363, NTH0371, NTH0375, NTH0378, NTH0379, NTH0384, NTH0385, NTH0396, NTH0407, NTH0408, NTH0411, NTH0417, NTH0419, NTH0420, NTH0424, NTH0429, NTH0430, NTH0431, NTH0432, NTH0433, NTH0434, NTH0435, NTH0438, NTH0455, NTH0478, NTH0484, NTH0485, NTH0486, NTH0487, NTH0488, NTH0489, NTH0498, NTH0500, NTH0501, NTH0506, NTH0509, NTH0510, NTH0511, NTH0520, NTH0523, NTH0526, NTH0527, NTH0531, NTH0534, NTH0536, NTH0539, NTH0559, NTH0561, NTH0573, NTH0577, NTH0579, NTH0580, NTH0581, NTH0582, NTH0583, NTH0584, NTH0585, NTH0586, NTH0588, NTH0599, NTH0603, NTH0604, NTH0606, NTH0615, NTH0617, NTH0631, NTH0637, NTH0644, NTH0645, NTH0653, NTH0662, NTH0663, NTH0664, NTH0667, NTH0668, NTH0673, NTH0677, NTH0680, NTH0681, NTH0683, NTH0687, NTH0690, NTH0691, NTH0692, NTH0694, NTH0695, NTH0696, NTH0706, NTH0707, NTH0711, NTH0715, NTH0716, NTH0717, NTH0721, NTH0724, NTH0725, NTH0726, NTH0728, NTH0729, NTH0730, NTH0749, NTH0752, NTH0756, NTH0768, NTH0776, NTH0792, NTH0797, NTH0818, NTH0827, NTH0832, NTH0839, NTH0841, NTH0843, NTH0844, NTH0862, NTH0864, NTH0866, NTH0867, NTH0877, NTH0879, NTH0885, NTH0886, NTH0892, NTH0895, NTH0896, NTH0900, NTH0901, NTH0904, NTH0906, NTH0921, NTH0924, NTH0928, NTH0929, NTH0930, NTH0931, NTH0932, NTH0933, NTH0937, NTH0938, NTH0942, NTH0949, NTH0953, NTH0955, NTH0961, NTH0964, NTH0970, NTH0971, NTH0972, NTH0973, NTH0985, NTH0987, NTH0991, NTH0992, NTH0993, NTH0994, NTH0995, NTH0996, NTH1007, NTH1016, NTH1017, NTH1020, NTH1025, NTH1026, NTH1027, NTH1028, NTH1029, NTH1037, NTH1040, NTH1049, NTH1067, NTH1069, NTH1070, NTH1073, NTH1082, NTH1086, NTH1089, NTH1090, NTH1108, NTH1111, NTH1112, NTH1114, NTH1115, NTH1116, NTH1122, NTH1129, NTH1131, NTH1142, NTH1149, NTH1150, NTH1153, NTH1157, NTH1159, NTH1161, NTH1162, NTH1176, NTH1178, NTH1179, NTH1193, NTH1195, NTH1196, NTH1204, NTH1205, NTH1207, NTH1208, NTH1209, NTH1210, NTH1211, NTH1214, NTH1216, NTH1220, NTH1225, NTH1234, NTH1235, NTH1237, NTH1241, NTH1244, NTH1245, NTH1246, NTH1247, NTH1248, NTH1249, NTH1250, NTH1251, NTH1252, NTH1253, NTH1270, NTH1271, NTH1294, NTH1299, NTH1313, NTH1315, NTH1316, NTH1325, NTH1330, NTH1333, NTH1337, NTH1339, NTH1342, NTH1353, NTH1361, NTH1367, NTH1374, NTH1375, NTH1381, NTH1382, NTH1390, NTH1391, NTH1395, NTH1396, NTH1399, NTH1414, NTH1415, NTH1418, NTH1419, NTH1437, NTH1441, NTH1454, NTH1456, NTH1471, NTH1474, NTH1487, NTH1489, NTH1490, NTH1491, NTH1492, NTH1493, NTH1494, NTH1495, NTH1496, NTH1497, NTH1504, NTH1516, NTH1540, NTH1543, NTH1555, NTH1563, NTH1564, NTH1567, NTH1571, NTH1573, NTH1574, NTH1580, NTH1587, NTH1598, NTH1599, NTH1600, NTH1601, NTH1602, NTH1603, NTH1605, NTH1606, NTH1607, NTH1611, NTH1612, NTH1615, NTH1616, NTH1626, NTH1627, NTH1628, NTH1647, NTH1656, NTH1657, NTH1658, NTH1676, NTH1677, NTH1687, NTH1697, NTH1702, NTH1703, NTH1713, NTH1734, NTH1740, NTH1742, NTH1744, NTH1745, NTH1748, NTH1749, NTH1751, NTH1752, NTH1753, NTH1754, NTH1755, NTH1756, NTH1757, NTH1758, NTH1759, NTH1760, NTH1765, NTH1769, NTH1770, NTH1778, NTH1798, NTH1804, NTH1811, NTH1812, NTH1815, NTH1816, NTH1817, NTH1818, NTH1820, NTH1821, NTH1822, NTH1829, NTH1832, NTH1833, NTH1837, NTH1842, NTH1845, NTH1854, NTH1857, NTH1904, NTH1910, NTH1914, NTH1916, NTH1920, NTH1921, NTH1922, NTH1945, NTH1946, NTH1947, NTH1948, NTH1956, NTH1962, NTH1964, NTH1968, NTH1989, NTH1994, NTH2019, NTH2031, NTH2035, NTH2043, NTH2056, NTH2060, NTH2069, NTH2075, NTH2093, NTH2096, NTH2109, NTH2110, NTH2112, NTH2113, NTH2114, NTH2117, NTH2156, NTH2159, NTH2170, NTH2197, NTH2198, NTH2199, NTH2206, NTH2207, NTH2216, NTH2217, NTH2219, NTH2220, NTH2221, NTH2222, NTH2223, NTH2226, NTH2229, NTH2245, NTH2273, NTH2284, NTH2287, NTH2305, NTH2309, NTH2315, NTH2316, NTH2323, NTH2326, NTH2330, NTH2332, NTH2343, NTH2349, NTH2353, NTH2362, NTH2363, NTH2364, NTH2386, NTH2414, NTH2442, NTH2451, NTH2455, NTH2456, NTH2457, NTH2458, NTH2460, NTH2461, NTH2463, NTH2464, NTH2466, NTH2467, NTH2468, NTH2471, NTH2480, NTH2481, NTH2482, NTH2483, NTH2484, NTH2485, NTH2486, NTH2487, NTH2488, NTH2500, NTH2510, NTH2524, NTH2525, NTH2527, NTH2528, NTH2536, NTH2537, NTH2549, NTH2562, NTH2563, NTH2572, NTH2573, NTH2575, NTH2584, NTH2585, NTH2590, NTH2604, NTH2607, NTH2608, NTH2609, NTH2635, NTH2647, NTH2648, NTH2650, NTH2655, NTH2664, NTH2668, NTH2679, NTH2684, NTH2693, NTH2694, NTH2696, NTH2697, NTH2703, NTH2704, NTH2706, NTH2707, NTH2708, NTH2709, NTH2710, NTH2711, NTH2712, NTH2713, NTH2715, NTH2716, NTH2718, NTH2719, NTH2720, NTH2721, NTH2723, NTH2724, NTH2725, NTH2726, NTH2727, NTH2729, NTH2730, NTH2731, NTH2737, NTH2744, NTH2753, NTH2778, NTH2781, NTH2783, NTH2784, NTH2785, NTH2791, NTH2804, NTH2806, NTH2809, NTH2810, and NTH2816.

NTH0861 to NTH0867

Protein NMB0419 from *Neisseria meningitidis* has been found to participate in the meningococcal invasion mechanism [2]. The protein was shown to modulate bacterial interaction with monolayers of human repiratory epithelial cells, promoting invasion. A homologous protein BPF001 is seen in *H. influenzae* biogroup aegyptius, but study of this protein was not possible.

The NTHi genome includes a region (SEQ ID NO: 5081) encoding a string of four polypeptides (NTH0861, NTH0863, NTH0865 and NTH0867) with strong similarity to NMB0419. This region and the four polypeptides are shown below:

```
GCCAGCTTGCTGCCTGCGGTCGACTCTANGAGACCCCTACAACAAAACATAATGCTAAAC

AAAAAATGTTTGGTTGTTTCAATTGTTGATTAATAAATGGACGATTTCTATGCGATTCAC
                          (SEQ ID NO: 1578)  NTH0867   M  R  F  T

AAAAACACTTTTTACCACCGCACTTTTAGGTGCTTCTATCTTTTCTTTTCAATCCACCGC
 K  T  L  F  T  T  A  L  L  G  A  S  I  F  S  F  Q  S  T  A

TTGGGCGGATACGCTGGAACAGCAATTCCAACAAGGTTCTGAAGCCACTACGAGAGGCGA
 W  A  D  T  L  E  Q  Q  F  Q  Q  G  S  E  A  T  T  R  G  D

TTATCAAACCACCTTTAAATTTTTGTTACCTCTGGCGGAGCAGGGAAATGCAGAGGCTCA
 Y  Q  T  T  F  K  F  L  L  P  L  A  E  Q  G  N  A  E  A  Q

ATTGATGTTGGGCGTGATGTATGCAAGAGGAATAGGCGTCAAACAAGATGATTTTGAAGC
 L  M  L  G  V  M  Y  A  R  G  I  G  V  K  Q  D  D  F  E  A

GGTGAAGTGGTATCGCCAAGCGGCGGAGCAGGGATATGCAAATGCTCAAGCTATATTGGG
 V  K  W  Y  R  Q  A  A  E  Q  G  Y  A  N  A  Q  A  I  L  G

ATTCTCATATCTTTTAGGACAAAGCGGTGTTCAAGTAAATAAATCTTTAGCCAAAGAATG
 F  S  Y  L  L  G  Q  S  G  V  Q  V  N  K  S  L  A  K  E  W

GTTTGGTAAGGCTTGTGATAATGGTGATCAAAATGGTTGCGAATATTATGGCAAGTTAAA
 F  G  K  A     D  N  G  D  Q  N  G     E  Y  Y  G  K  L  N

TAGAGGGGAGCTCTAATGCCAACTTTACAATGCGAATTTTGGAATGTAGGGCAAGGGTTA
 R  G  E  L  *

TTTTCAAGTGGGCGTATTCAAATGGGAGACGCCCCAGCCTTTCATTGGGTTTATGGTTTG

CAAGTTCCTCATCATGGTTCAAAGCCAATTTTAGTGAATAAAAATAAAAGATTATCCATT

CATTCAATTTAATAGGAAAACAAATGAAACTCACAAAAACACTTCTTACCACCGCACTTT
                                                 (SEQ ID NO: 1574)
         NTH0865   M  K  L  T  K  T  L  L  T  T  A  L  F

TCGGTGCTTCTATTTTTTCTTTTCAATCCACCGCTTGGGCGGATACGCCGGAACAGCAAT
 G  A  S  I  F  S  F  Q  S  T  A  W  A  D  T  P  E  Q  Q  F

TCCAACAAGGTTTAACCGCTTATGAGCAAAGCAACTATCAAACCGCCTTTAAACTTTGGT
 Q  Q  G  L  T  A  Y  E  Q  S  N  Y  Q  T  A  F  K  L  W  L

TACCTCTGGCGGAGCAGGGAGATGCACAGGCTCAAGGTGGTTTGGGCATGATGTATGAAA
 P  L  A  E  Q  G  D  A  Q  A  Q  G  G  L  G  M  M  Y  E  R

GAGGACTTGGCGTAAAACAAGATGATTTCAAAGCAGTGAACTGGTATCGCAAAGCGGCGG
 G  L  G  V  K  Q  D  D  F  K  A  V  N  W  Y  R  K  A  A  R

AGCAGGGGGATGCAGATGCTCAATTAAATTTGGGTGCGATGTATGCAATCGGACGTGGCG
 Q  G  D  A  D  A  Q  L  N  L  G  A  M  Y  A  I  G  R  G  V

TAAAACAAGATGGTGTTGAAGCGGTGAAGTGGTTTCGCAAAGCGGCAGAGCAGGGAAATG
 K  Q  D  G  V  E  A  V  K  W  F  R  K  A  A  E  Q  G  N  A

CAAAGGCTCAAAATGGTTTGGGCATGATGTATGACGGAGGACTTGGCATAAAACAAGATT
 K  A  Q  N  G  L  G  M  M  Y  D  G  G  L  G  I  K  Q  D  Y

ATTTCAAAGCGGTGAAATGGCATCGCAAAGCGGCGGAGCAGGGATATGGAGGTGCTCAAG
 F  K  A  V  K  W  H  R  K  A  A  E  Q  G  Y  G  G  A  Q  V

TTATGTTGGGATTCTCATATCTTTCGGGAAAAGGTGTTCAAGTAAATAAATCTTTAGCCA
 M  L  G  F  S  Y  L  S  G  K  G  V  Q  V  N  K  S  L  A  K

AAGAATGGTTTGGTAAGGCTTGTGATAATGGTGAACAAGTGGGTTGTGAATATTATGGCA
 E  W  F  G  K  A     D  N  G  E  Q  V  G     E  Y  Y  G  K

AGCTAAATAGAGGGGAACGCTAATGCCAACTTTACAATGCGAATTTTGGAATGTAGGGCA
 L  N  R  G  E  R  *

AGGGTTATTTTCAAGTGGGCGTATTCAAATGGGAGACGCCCAAGCCTTTCATTGGGTTTA

TGGTTTGCAAGTTCCTCATCATGGTTCAAAGCCAATTTTAGTGAATAAAAATAAAAGATT

ATCCATTCATTCAATTTAATAGGAAAACAAATGAAACTCACAAAAACACTTCTTACCAC
         (SEQ ID NO: 1570) NTH0863   M  K  L  T  K  T  L  L  T  T

CGCACTTTTCGGTGCTTCTGTATTTTCTTTTCAATCCACCGCTTGGGCGGATACGCTGGA
 A  L  F  G  A  S  V  F  S  F  Q  S  T  A  W  A  D  T  L  E

ACAGCAATTCCAACAAGGTTTAACCGCTTATGAGCAAAGCAACTATCAAACCGCCTTTAA
```

```
                   Q  Q  F  Q  Q  G  L  T  A  Y  E  Q  S  N  Y  Q  T  A  F  K
ACTTTGGTTACCTATGGCAGAGCAGGGATATGCAAAGGCTCAATTTAATTTGGGCGTGAT
 L  W  L  P  M  A  E  Q  G  Y  A  K  A  Q  F  N  L  G  V  M

GTATGCTAAGGGGCAAGGCGTCAAACAAGATGATTTTGAAGCGGTGAAGTGGTTTCGCAA
 Y  A  K  G  Q  G  V  K  Q  D  D  F  E  A  V  K  W  F  R  K

AGCGGCGGAGCAGGGATATGCAGAGGCTAAATTTAATTTGGGCCATATGTATTCTAAGGG
 A  A  E  Q  G  Y  A  E  A  K  F  N  L  G  H  M  Y  S  K  G

ACGAGGCGTCAAACAAGATGATTTTGAAGCAGTGAACTGGTATCGCAAAGCGGCGGAGCA
 R  G  V  K  Q  D  D  F  E  A  V  N  W  Y  R  K  A  A  E

GGGAGATGCAGATGCTCAAGCTATATTGGGATTCTTATATCTTTTAGGAGAAAGAGGTGT
 G  D  A  D  A  Q  A  I  L  G  F  L  Y  L  L  G  E  R  G  V

CAAGTAAATAATTCTTTAGCCAAGNAATGGTNTGGTAAGGCTTGTGATAATGGTAATCAA
 K  *

AATGGCTGCGAATATTATGGCAAGCTAAATAGAGGGGAGCTCTAATGCCCACTTTTACAA

TGCGAATTNTGGAATGTAGGGCAAGGGTTATTTTCAAGTGGGCGTATTCAAGTGGAGACG

CNNCCAAGCCTTTCATTGGGTTTATGGTTTGCAAGTTCCTCATCATGGTTCANAGCCCAA

TTTAGTGNAATAAAAATAAAAGATTATCCATTCATTCAATTTAATAGGAAAACAAAATGA
                              (SEQ ID NO: 1566) NTH0861 M  K

AACTCACAAAAACACTTCTTACCACCGCACTTTTAGGTGCTTCTGTATTATCTTTTCAAT
 L  T  K  T  L  L  T  T  A  L  L  G  A  S  V  L  S  F  Q  S

CCACCGCTTGGGCGGATACGCTGGAACAGCAATTCCAACAAGGTTTAACCGCTTATGAGC
 T  A  W  A  D  T  L  E  Q  Q  F  Q  Q  G  L  T  A  Y  E  Q

AAAGCAACTATCAAACCGCCTTTAAACTTTGGTTACCTCTGGCGGAGCAGGGAGATGCAA
 S  N  Y  Q  T  A  F  K  L  W  L  P  A  E  Q  G  D  A  N

ATGTTCAATTTAATTTGGGCGTGATGTATGCTGAGGGGCAAGGCGTCAAACAAGATGATT
 V  Q  F  N  L  G  V  M  Y  A  E  G  Q  G  V  K  Q  D  D  F

TTGAAGCGGTGAAATGGTATCGCAAAGCGGCGGAGCAGGGAGATGCAAATGCTCAGGCTT
 E  A  V  K  W  Y  R  K  A  A  E  Q  G  D  A  N  A  Q  A  Y

ATTTAGGTTTGGCTTATACTGAAGGGCGTGGTGTAAGACAAGATTATACCGAAGCGGTGA
 L  G  L  A  Y  T  E  G  R  G  V  R  Q  D  Y  T  E  A  V  K

AGTGGTTTCGCAAAGCGGCGGAGCAGGGACATGCAAATGCTCAAGCTATATGGGATCTCT
 W  F  R  K  A  A  E  Q  G  H  A  N  A  Q  A  I  W  D  L  F

TTCTTTAGGGTACCGAGCCGAATCGATCCA
 L  *
```

The four coding sequences are aligned (ClustalW) below:

```
NTH0863  ATGAAACTCACAAAAACACTTCTTACCACCGCACTTTTCGGTGCTTCTGTATTTTCTTTT

NTH0867  ATGCGATTCACAAAAACACTTTTTACCACCGCACTTTTAGGTGCTTCTATCTTTTCTTTT

NTH0865  ATGAAACTCACAAAAACACTTCTTACCACCGCACTTTTCGGTGCTTCTATTTTTTCTTTT

NTH0861  ATGAAACTCACAAAAACACTTCTTACCACCGCACTTTTAGGTGCTTCTGTATTATCTTTT
         *** * *************  ****************  ********  *  ** ******

NTH0863  CAATCCACCGCTTGGGCGGATACGCTGGAACAGCAATTCCAACAAGGTTTAACCGCTTAT

NTH0867  CAATCCACCGCTTGGGCGGATACGCTGGAACAGCAATTCCAACAAGGTTCTGAAGCCACT

NTH0865  CAATCCACCGCTTGGGCGGATACGCCGGAACAGCAATTCCAACAAGGTTTAACCGCTTAT

NTH0861  CAATCCACCGCTTGGGCGGATACGCTGGAACAGCAATTCCAACAAGGTTTAACCGCTTAT
         *************************  **************************    **   *

NTH0863  GAGCAAAGCAACTATCAAACCGCCTTTAAACTTTGGTTACCTATGGCAGAGCAGGGATAT

NTH0867  ACGAGAGGCGATTATCAAACCACCTTTAAATTTTGTTACCTCTGGCGGAGCAGGGAAAT

NTH0865  GAGCAAAGCAACTATCAAACCGCCTTTAAACTTTGGTTACCTCTGGCGGAGCAGGGAGAT
```

```
NTH0861 GAGCAAAGCAACTATCAAACCGCCTTTAAACTTTGGTTACCTCTGGCGGAGCAGGGAGAT
        *  *  ** * ********* ******** *** ******* **** ********* **

NTH0863 GCAAAGGCTCAATTTAATTTGGGCGTGATGTATGCTAAGGGGCAAGGCGTCAAACAAGAT

NTH0867 GCAGAGGCTCAATTGATGTTGGGCGTGATGTATGCAAGAGGAATAGGCGTCAAACAAGAT

NTH0865 GCACAGGCTCAAGGTGGTTTGGGCATGATGTATGAAAGAGGACTTGGCGTAAAACAAGAT

NTH0861 GCAAATGTTCAATTTAATTTGGGCGTGATGTATGCTGAGGGGCAAGGCGTCAAACAAGAT
        *** * * ****      ****** *********   **    ***** *********

NTH0863 GATTT-------------------------------------------------------

NTH0867 GATTT-------------------------------------------------------

NTH0865 GATTTCAAAGCAGTGAACTGGTATCGCAAAGCGGCGGAGCAGGGGGATGCAGATGCTCAA

NTH0861 GATTT-------------------------------------------------------
        *****

NTH0863 ------------------------------------------------------TGAAGCG

NTH0867 ------------------------------------------------------TGAAGCG

NTH0865 TTAAATTTGGGTGCGATGTATGCAATCGGACGTGGCGTAAAACAAGATGGTGTTGAAGCG

NTH0861 ------------------------------------------------------TGAAGCG
                                                              *******

NTH0863 GTGAAGTGGTTTCGCAAAGCGGCGGAGCAGGGATATGCAGAGGCTAAATTTAATTTGGGC

NTH0867 GTGAAGTGGTATCGCCAAGCGGCGGAGCAGGGATATGCAAA-------------------

NTH0865 GTGAAGTGGTTTCGCAAAGCGGCAGAGCAGGGAAATGCAAAGGCTCAAAATGGTTTGGGC

NTH0861 GTGAAATGGTATCGCAAAGCGGCGGAGCAGGGAGATGCAAA-------------------
        ***** **** **** ******* ******** ***** *

NTH0863 CATATGTATTCTAAGGGACGAGGCGTCAAACAAGATGATTTTGAAGCAGTGAACTGGTAT

NTH0867 ------------------------------------------------------------

NTH0865 ATGATGTATGACGGAGGACTTGGCATAAAACAAGATTATTTCAAAGCGGTGAAATGGCAT

NTH0861 ------------------------------------------------------------

NTH0863 CGCAAAGCGGCGGAGCAGGGAGATGCAGATGCTCAAGCTATATTGGGATTCTTATATCTT

NTH0867 -----------------------------TGCTCAAGCTATATTGGGATTCTCATATCTT

NTH0865 CGCAAAGCGGCGGAGCAGGGATATGGAGGTGCTCAAGTTATGTTGGGATTCTCATATCTT

NTH0861 -----------------------------TGCTCAGGCTTATTTAGGTTTGGCTTATACT
                                     ****** * *  ** ** **    *** *

NTH0863 TTAGGAGAAAGAGGTGT-CAAGTAAATAATTCTTTAGCCAAGNAATGGTNTGGTAAGGCT

NTH0867 TTAGGACAAAGCGGTGTTCAAGTAAATAAATCTTTAGCCAAAGAATGGTTTGGTAAGGCT

NTH0865 TCGGGAAAA---GGTGTTCAAGTAAATAAATCTTTAGCCAAAGAATGGTTTGGTAAGGCT

NTH0861 GAAGGGCGT---GGTGTAAGACAAGATTATACCGAAGCGGTGAAGTGGTTTCGCAAAGC-
          **       ****   *  * ** *   ***    * ****  * ** **

NTH0863 TGTGATAATGGTAATCAAAATGGCTGCGAATATTATGGCAAGCTAAATAGAGGGGAGCTC

NTH0867 TGTGATAATGGTGATCAAAATGGTTGCGAATATTATGGCAAGTTAAATAGAGGGGAGCTC

NTH0865 TGTGATAATGGTGAACAAGTGGGTTGTGAATATTATGGCAAGCTAAATAGAGGGGAACGC

NTH0861 ---------GGCGGAGCAGGGACATGCAAATGCT----CAAGCTATAT----GGGATCTC
                   **      *   ** *** *     **** ** **    **** * *

NTH0863 TAATGCCCACTTTTACAATGCGAATTNTGGAATGTAGGGCAAGGGTTATTTTCAAGTGGG

NTH0867 TAATGCCAACTTT-ACAATGCGAATTTTGGAATGTAGGGCAAGGGTTATTTTCAAGTGGG

NTH0865 TAATGCCAACTTT-ACAATGCGAATTTTGGAATGTAGGGCAAGGGTTATTTTCAAGTGGG

NTH0861 TTTCTTTAGGGTA-CCGAGCCGAATC----GATCCA------------------------
```

```
                  *         *    * *  *****     **  *
NTH0863  CGTATTCAAGTGGAGACGCNNCCAAGCCTTTCATTGGGTTTATGGTTTGCAAGTTCCTCA

NTH0867  CGTATTCAAATGG-GAGACGCCCCAGCCTTTCATTGGGTTTATGGTTTGCAAGTTCCTCA

NTH0865  CGTATTCAAATGG-GAGACGCCCAAGCCTTTCATTGGGTTTATGGTTTGCAAGTTCCTCA

NTH0861  ------------------------------------------------------------

NTH0863  TCATGGTTCANAGCCCAATTTAGTGNAATAAAAATAAAAGATTATCCATTCATTCAATTT

NTH0867  TCATGGTTCAAAGCCAATTTTAGTGAA-TAAAAATAAAAGATTATCCATTCATTCAATTT

NTH0865  TCATGGTTCAAAGCCAATTTTAGTGAA-TAAAAATAAAAGATTATCCATTCATTCAATTT

NTH0861  ------------------------------------------------------------

SEQ ID NO: 5083
NTH0863  AATAGGAAAACAAA

SEQ ID NO: 5085
NTH0867  AATAGGAAAACAA-

SEQ ID NO: 5084
NTH0865  AATAGGAAAACAAA

SEQ ID NO: 5082
NTH0861  --------------
```

The encoded polypeptides are aligned below, together with the bpf001 and NMB0419 sequences:

```
NTH0861  -----------MKLTKTLLTTALLG---------ASVLSFQS---TAWADTLEQQFQQG

NTH0863  -----------MKLTKTLLTTALFG---------ASVFSFQS---TAWADTLEQQFQQG

NTH0865  -----------MKLTKTLLTTALFG---------ASIFSFQS---TAWADTPEQQFQQG

NTH0867  -----------MRFTKTLFTTALLG---------ASIFSFQS---TAWADTLEQQFQQG

BPF001   -----------MKLTKTLFTSALLG---------ASILSFHP---TVAAMDFGT--QVG

NMB0419  -----------MKQTVKWLAAALIALGLNRAVWADDVSDFRENLQAAAQGNAAAQYNLG
                    *: *  . :::**:.         .: .*:    :.         : *

NTH0861  LTAYE----QSNYQTAFKLWLPLAEQ-GDANVQFNLGVMYAEGQGVKQDDFEAVKWYRKA

NTH0863  LTAYE----QSNYQTAFKLWLPMAEQ-GYAKAQFNLGVMYAKGQGVKQDDFEAVKWFRKA

NTH0865  LTAYE----QSNYQTAFKLWLPLAEQ-GDAQAQGGLGMMYERGLGVKQDDFKAVNWYRKA

NTH0867  SEATT----RGDYQTTFKFLLPLAEQ-GNAEAQLMLGVMYARGIGVKQDDFEAVKWYRQA

BPF001   IDAYR----KNDFAQAAEQFKDAGIVRGDPTAQLFLGRMYYNGEFFKQDYVEAAKWYRKA

NMB0419  AMYYKGRGVRRDDAEAVRWYRQAAEQ-GLAQAQYNLGWMYANGRGVRQDDTEAVRWYRQA
                 : :   :  .      *  .* ** ** .*  .:**  :*..*:*:*

NTH0861  AEQG--------------------------------------------------------

NTH0863  AEQG--------------------------------------------------------

NTH0865  AEQGDADAQLNLGAMYAIGRGVKQDGVEAVKWFRKAAEQGNAKAQNGLGMMYDGGLGIKQ

NTH0867  AEQG--------------------------------------------------------

BPF001   AEQGEEFGLLFLG------------------------------------ETYEDGEGVEK

NMB0419  AAQGVVQAQYNLG------------------------------------VIYAEGRGVRQ
         * **

NTH0861  ----------------DANAQAYLGLAYTEGR-GVRQDYTEAVKWFRKAAEQGHANAQAI

NTH0863  ----------------YAEAKFNLGHMYSKGR-GVKQDDFEAVNWYRKAAEQGDADAQAI

NTH0865  DYFKAVKWHRKAAEQGYGGAQVMLGFSYLSGK-GVQVNKSLAKEWFGKACDNGEQVGCEY
```

```
NTH0867    ---------------YANAQAILGFSYLLGQSGVQVNKSLAKEWFGKACDNGDQNGCEY

BPF001     DYAEAAKLYRKAAEQGSAEGQMALGKMYRFGN-GVEKDYAEAIKLYRKSAEQGNFTALFF

NMB0419    DDVEAVRWFRQAAAQGVAQAQNNLGVMYAERR-GVRQDRALAQEWFGKACQNGDQDGCDN
                     . .:  **  *   .**. :   *  : : *:..:*.  .

SEQ ID NO: 1566
NTH0861    WDLFL----------------

SEQ ID NO: 1570
NTH0863    LGFLYLLGERGVK---------

SEQ ID NO: 1574
NTH0865    YGKLNR-GER------------

SEQ ID NO: 1578
NTH0867    YGKLNR-GEL------------

SEQ ID NO: 5086
BPF001     LGEMYDNGVGVKQNKAESQRII

SEQ ID NO: 5087
NMB0419    DQRLKAGY--------------
               :
```

The serial repeats of four closely-related genes that are also related to genes involved in bacterial invasion is noteworthy, and NTH0861, NTH0863, NTH0865 and NTH0867 are of particular interest for immunisation purposes. NTH0867 in particular is an outer-membrane protein that is not seen in the Rd genome, and is of special interest.

Moreover, as well as being caused by NTHi, acute otitis media is often caused by *Moraxella catarrhalis* and *Streptococcus pneumoniae*. Four proteins have been identified that in the NTHi genome that have homologs in the *M. catarrhalis* genome, namely NTH0861 (SEQ ID NO: 1566), NTH0863 (SEQ ID NO: 1570), NTH0865 (SEQ ID NO: 1574) and NTH0867 (SEQ ID NO: 1578). These proteins can thus be used as antigens for a general AOM vaccine. The corresponding *M. catarrhalis* antigens can also be used, either on their own or in combination with the NTHi antigens.

A variant of SEQ ID NO: 1566 is given as SEQ ID NO: 5095:

```
                      10        20        30        40        50        60        70        80
                      |         |         |         |         |         |         |         |
           1566    MKLTKTLLTTALLGASVLSFQSTAWADTLEQQFQQGLTAYEQSNYQTAFKLWLPLAEQGDANVQFNLGVMYAEGQGVKQD
           5095    MKLTKTLLTTALLGASVFSFQSTAWADTPEQQFQQGSTAYEQSDYQTAFKLWLPMAEQGDANVQFNLGVMYAKGQGVKQD
                   *****************:********* ******* ******:*********:****************:*******
                      90       100       110       120       130       140       150       160
                      |         |         |         |         |         |         |         |
           1566    DFEAVKWYRKAAEQ-----------------------------------GDANAQAYLGLAYTEGRGVRQDYTEAVKWF
           5095    DFEAVKWYRKAAEQGHAKAQFNLGVMYAKGQGVKQDDFKAVKWYRKAAEQGYADAQANLGSAYSAGRGVRQDYIEAVKWF
                   **************                                    * *:*** ** **: ******* ******
                     170       180       190       200       210
                      |         |         |         |         |
           1566    RKAAEQGHANAQAIWDLFL-----------------------------------
           5095    KKAAENGSADGQFKLGVLYLIGQSIQKDRTLAKEWFGKACDNGEQRGCEYYGKLNRGEL
                   :****:* *:.*    .*.
```

A variant of SEQ ID NO: 1570 is given as SEQ ID NO: 5094:

```
                      10        20        30        40        50        60        70        80
                      |         |         |         |         |         |         |         |
           1570    MKLTKTLLTTALFGASVFSFQSTAWADTLEQQFQQGLTAYEQSNYQTAFKLWLPMAEQGYAKAQFNLGVMTAKGQGVKQD
           5094    MKLTKTLLTTALLGASVFSFQSTAWADTPEQQFQQGSTAYEQSDYQTAFKLWLPMAEQGDANVQFNLGVMYAKGQGVKQD
                   ************:*************** ******* ******:*************  : ******** *********
```

```
                  90        100       110       120       130       140       150
                   |         |         |         |         |         |         |
1570      DFEAVKWFRKAAEQGYAEAKFNLGHMYSKG-RGVKQDDFEAVNWYRKAAEQGDADAQAILGFLYLLGERGVK
5094      DFEAVKWFRKAAEQGHAKAQAILGFSYLLGERGVQVNKSLAKEWFGKACDNGNQDGCEYYG---KLNRGGF-
          ***************:*:*:  **.*  * ***: :.  * :*: **.::*: *.     *   *.. *.
```

A variant of SEQ ID NO: 1574 is given as SEQ ID NO: 5093:

```
                  10        20        30        40        50        60        70        80
                   |         |         |         |         |         |         |         |
1574      MKLTKTLLTTALFGASIFSFQSTAWADTPEQQFQQGLTAYEQSNYQTAFKLWLPLAEQGDAQAQGGLGMMYERGLGVKQD
5093      MKLTKTLLTTALFGASIFSFQSTAWADTPEQQFQQGLTAYEQSDYQTAFKLWLPMAEQGYAQAQGGLGMMYERGLGVKQD
          *******************************************:**********:****.*********************
                  90        100       110       120       130       140       150       160
                   |         |         |         |         |         |         |         |
1574      DFKAVNWYRKAAEQGDADAQLNLGAMYAIGRGVKQDGVEAVKWFRKAAEQGNAKAQNGLGMMYDGGLGIKQDYFKAVKWH
5093      DFKAVNWYRKAAEQGDADAQLNLGAMYAIGHGVKQDGVEAVKWFRKAAEQGNAKAQNGLGMMYRGRLGIKQDYFKAVKWY
          *****************************:*******************************.* *************:
                  170       180       190       200       210
                   |         |         |         |         |
1574      RKAAEQGYGGAQVMLGFSYLSGKGVQVNKSLAKEWFGKACDNGEQVGCEYYGKLNRGER
5093      RKAAEQGYGGAQVMLGFSYLSGKGVQVNKSLAKEWFGKACDNGEQVGCEYYSKLNRGER
          ***************************************************.*******
```

A variant of SEQ ID NO: 1578 is given as SEQ ID NO: 5092:

```
                  10        20        30        40        50        60        70        80
                   |         |         |         |         |         |         |         |
5092      MRFTKTLFTTALLGASVFSFQSTAWADTLEQQFQQGSEATTRGDYQTTFKFLLPLAEQGNALAQMMLGVMYAKGQGVKQD
1578      MRFTKTLFTTALLGASIFSFQSTAWADTLEQQFQQGSEATTRGDYQTTFKFLLPLAEQGNAEAQLMLGVMYARGIGVKQD
          ***************:*********************************************  **:*******:* *****
                  90        100       110       120       130       140
                   |         |         |         |         |         |
5092      DVEAVKWYRKAAEQGYADAQAMLGFSYLLGQSGVQVNKSLAKEWFGKACDNGDQNGCEYYGKLNRGEL
1578      DFEAVKWYRQAAEQGYANAQAILGFSYLLGQSGVQVNKSLAKEWFGKACDNGDQNGCEYYGKLNRGEL
          *.*******:*******.***:********************************************
```

Preferred NTH0861 proteins have identity to both of SEQ ID NOS: 1566 and 5095. Preferred NTH0863 proteins have identity to both of SEQ ID NOS: 1570 and 5094. Preferred NTH0865 proteins have identity to both of SEQ ID NOS: 1574 and 5093. Preferred NTH0867 proteins have identity to both of SEQ ID NOS: 1578 and 5092.

It will be understood that the invention has been described by way of example only and modifications may be made whilst remaining within the scope and spirit of the invention.

TABLE I

| MISSING NTHnnnn VALUES between NTH0001 and NTH2832 | | | | | | | | | | | |
|---|---|---|---|---|---|---|---|---|---|---|---|
| 0008 | 0031 | 0042 | 0054 | 0056 | 0066 | 0074 | 0077 | 0093 | 0111 | 0160 | 0162 |
| 0166 | 0171 | 0179 | 0210 | 0213 | 0214 | 0219 | 0229 | 0231 | 0276 | 0281 | 0288 |
| 0293 | 0322 | 0332 | 0357 | 0362 | 0381 | 0395 | 0398 | 0404 | 0406 | 0409 | 0410 |

TABLE I-continued

MISSING NTHnnnn VALUES between NTH0001 and NTH2832

| | | | | | | | | | | | |
|---|---|---|---|---|---|---|---|---|---|---|---|
| 0415 | 0439 | 0445 | 0446 | 0452 | 0466 | 0471 | 0491 | 0497 | 0516 | 0533 | 0538 |
| 0541 | 0546 | 0551 | 0553 | 0556 | 0569 | 0578 | 0598 | 0600 | 0610 | 0623 | 0639 |
| 0649 | 0666 | 0693 | 0713 | 0722 | 0727 | 0742 | 0746 | 0757 | 0763 | 0780 | 0789 |
| 0791 | 0793 | 0800 | 0809 | 0816 | 0855 | 0883 | 0891 | 0902 | 0911 | 0915 | 0916 |
| 0922 | 0943 | 0944 | 0957 | 0975 | 0978 | 0980 | 0998 | 0999 | 1013 | 1034 | 1044 |
| 1047 | 1055 | 1056 | 1065 | 1072 | 1076 | 1079 | 1099 | 1113 | 1118 | 1119 | 1128 |
| 1133 | 1134 | 1136 | 1146 | 1147 | 1158 | 1160 | 1170 | 1194 | 1199 | 1213 | 1219 |
| 1223 | 1232 | 1243 | 1257 | 1260 | 1288 | 1289 | 1296 | 1312 | 1317 | 1329 | 1335 |
| 1347 | 1350 | 1356 | 1358 | 1362 | 1364 | 1372 | 1377 | 1385 | 1452 | 1458 | 1469 |
| 1478 | 1481 | 1486 | 1488 | 1502 | 1517 | 1518 | 1529 | 1536 | 1547 | 1553 | 1557 |
| 1560 | 1566 | 1592 | 1595 | 1596 | 1604 | 1642 | 1649 | 1667 | 1669 | 1674 | 1691 |
| 1699 | 1711 | 1715 | 1721 | 1723 | 1727 | 1728 | 1731 | 1737 | 1741 | 1743 | 1746 |
| 1750 | 1761 | 1772 | 1784 | 1797 | 1810 | 1814 | 1823 | 1843 | 1844 | 1856 | 1864 |
| 1866 | 1878 | 1902 | 1909 | 1918 | 1957 | 1961 | 1979 | 1985 | 1987 | 1990 | 2004 |
| 2006 | 2015 | 2017 | 2023 | 2033 | 2037 | 2042 | 2054 | 2077 | 2080 | 2098 | 2104 |
| 2107 | 2125 | 2154 | 2167 | 2171 | 2174 | 2179 | 2194 | 2203 | 2210 | 2218 | 2237 |
| 2239 | 2240 | 2244 | 2254 | 2255 | 2267 | 2268 | 2270 | 2275 | 2278 | 2286 | 2290 |
| 2295 | 2300 | 2302 | 2312 | 2320 | 2334 | 2340 | 2355 | 2357 | 2366 | 2367 | 2374 |
| 2380 | 2400 | 2409 | 2431 | 2444 | 2459 | 2523 | 2540 | 2547 | 2551 | 2574 | 2580 |
| 2589 | 2601 | 2611 | 2614 | 2624 | 2628 | 2637 | 2639 | 2645 | 2652 | 2658 | 2662 |
| 2677 | 2692 | 2699 | 2700 | 2728 | 2734 | 2746 | 2760 | 2767 | 2773 | 2787 | 2799 |
| 2805 | 2808 | 2819 | 2822 | | | | | | | | |

TABLE II

Preferred polypeptides

| | | | | | | | |
|---|---|---|---|---|---|---|---|
| NTH0001 | NTH0002 | NTH0004 | NTH0005 | NTH0012 | NTH0014 | NTH0015 | NTH0016 |
| NTH0017 | NTH0019 | NTH0020 | NTH0021 | NTH0022 | NTH0024 | NTH0025 | NTH0032 |
| NTH0033 | NTH0034 | NTH0035 | NTH0036 | NTH0037 | NTH0038 | NTH0040 | NTH0041 |
| NTH0043 | NTH0045 | NTH0048 | NTH0049 | NTH0050 | NTH0051 | NTH0052 | NTH0053 |
| NTH0057 | NTH0059 | NTH0060 | NTH0061 | NTH0064 | NTH0067 | NTH0073 | NTH0076 |
| NTH0085 | NTH0089 | NTH0091 | NTH0092 | NTH0094 | NTH0097 | NTH0101 | NTH0104 |
| NTH0106 | NTH0107 | NTH0110 | NTH0114 | NTH0116 | NTH0118 | NTH0119 | NTH0120 |
| NTH0121 | NTH0122 | NTH0123 | NTH0124 | NTH0125 | NTH0128 | NTH0129 | NTH0132 |
| NTH0134 | NTH0135 | NTH0136 | NTH0138 | NTH0140 | NTH0146 | NTH0148 | NTH0151 |
| NTH0153 | NTH0154 | NTH0155 | NTH0157 | NTH0158 | NTH0159 | NTH0161 | NTH0163 |
| NTH0164 | NTH0167 | NTH0169 | NTH0173 | NTH0174 | NTH0176 | NTH0177 | NTH0180 |
| NTH0184 | NTH0185 | NTH0186 | NTH0187 | NTH0189 | NTH0190 | NTH0191 | NTH0192 |
| NTH0193 | NTH0194 | NTH0195 | NTH0197 | NTH0198 | NTH0199 | NTH0203 | NTH0206 |
| NTH0208 | NTH0209 | NTH0223 | NTH0224 | NTH0226 | NTH0227 | NTH0228 | NTH0232 |
| NTH0235 | NTH0236 | NTH0237 | NTH0238 | NTH0241 | NTH0242 | NTH0244 | NTH0247 |
| NTH0248 | NTH0250 | NTH0251 | NTH0252 | NTH0253 | NTH0254 | NTH0255 | NTH0256 |
| NTH0263 | NTH0264 | NTH0265 | NTH0269 | NTH0270 | NTH0278 | NTH0279 | NTH0280 |
| NTH0282 | NTH0283 | NTH0284 | NTH0285 | NTH0289 | NTH0290 | NTH0295 | NTH0297 |
| NTH0298 | NTH0299 | NTH0300 | NTH0302 | NTH0307 | NTH0308 | NTH0310 | NTH0311 |
| NTH0312 | NTH0313 | NTH0317 | NTH0319 | NTH0320 | NTH0321 | NTH0325 | NTH0326 |
| NTH0327 | NTH0328 | NTH0331 | NTH0333 | NTH0334 | NTH0335 | NTH0339 | NTH0341 |
| NTH0346 | NTH0347 | NTH0348 | NTH0351 | NTH0352 | NTH0353 | NTH0356 | NTH0358 |
| NTH0363 | NTH0366 | NTH0371 | NTH0372 | NTH0375 | NTH0378 | NTH0379 | NTH0384 |
| NTH0385 | NTH0388 | NTH0396 | NTH0397 | NTH0400 | NTH0401 | NTH0402 | NTH0405 |
| NTH0407 | NTH0408 | NTH0411 | NTH0412 | NTH0417 | NTH0418 | NTH0419 | NTH0420 |
| NTH0421 | NTH0424 | NTH0426 | NTH0427 | NTH0429 | NTH0430 | NTH0431 | NTH0432 |
| NTH0433 | NTH0434 | NTH0435 | NTH0437 | NTH0438 | NTH0444 | NTH0453 | NTH0455 |
| NTH0457 | NTH0459 | NTH0460 | NTH0461 | NTH0462 | NTH0463 | NTH0465 | NTH0468 |
| NTH0469 | NTH0473 | NTH0475 | NTH0478 | NTH0484 | NTH0485 | NTH0486 | NTH0487 |
| NTH0488 | NTH0489 | NTH0490 | NTH0493 | NTH0496 | NTH0498 | NTH0500 | NTH0501 |
| NTH0502 | NTH0504 | NTH0506 | NTH0507 | NTH0509 | NTH0510 | NTH0511 | NTH0512 |
| NTH0513 | NTH0518 | NTH0520 | NTH0523 | NTH0524 | NTH0526 | NTH0527 | NTH0528 |
| NTH0529 | NTH0531 | NTH0534 | NTH0536 | NTH0539 | NTH0544 | NTH0545 | NTH0547 |
| NTH0549 | NTH0559 | NTH0561 | NTH0565 | NTH0566 | NTH0573 | NTH0574 | NTH0577 |
| NTH0579 | NTH0580 | NTH0581 | NTH0582 | NTH0583 | NTH0584 | NTH0585 | NTH0586 |
| NTH0587 | NTH0588 | NTH0590 | NTH0599 | NTH0603 | NTH0604 | NTH0606 | NTH0615 |
| NTH0617 | NTH0618 | NTH0619 | NTH0622 | NTH0624 | NTH0626 | NTH0630 | NTH0631 |
| NTH0636 | NTH0637 | NTH0638 | NTH0642 | NTH0643 | NTH0644 | NTH0645 | NTH0646 |
| NTH0647 | NTH0648 | NTH0653 | NTH0654 | NTH0656 | NTH0658 | NTH0661 | NTH0662 |
| NTH0663 | NTH0664 | NTH0667 | NTH0668 | NTH0673 | NTH0675 | NTH0676 | NTH0677 |
| NTH0678 | NTH0680 | NTH0681 | NTH0683 | NTH0687 | NTH0690 | NTH0691 | NTH0692 |
| NTH0694 | NTH0695 | NTH0696 | NTH0702 | NTH0703 | NTH0706 | NTH0707 | NTH0709 |
| NTH0710 | NTH0711 | NTH0712 | NTH0715 | NTH0716 | NTH0717 | NTH0718 | NTH0721 |
| NTH0724 | NTH0725 | NTH0726 | NTH0728 | NTH0729 | NTH0730 | NTH0738 | NTH0740 |
| NTH0744 | NTH0745 | NTH0749 | NTH0750 | NTH0752 | NTH0755 | NTH0756 | NTH0762 |
| NTH0764 | NTH0765 | NTH0768 | NTH0771 | NTH0774 | NTH0776 | NTH0788 | NTH0792 |
| NTH0794 | NTH0795 | NTH0796 | NTH0797 | NTH0798 | NTH0802 | NTH0803 | NTH0804 |
| NTH0813 | NTH0814 | NTH0815 | NTH0818 | NTH0820 | NTH0821 | NTH0822 | NTH0827 |

TABLE II-continued

Preferred polypeptides

| | | | | | | | |
|---|---|---|---|---|---|---|---|
| NTH0829 | NTH0832 | NTH0834 | NTH0835 | NTH0836 | NTH0838 | NTH0839 | NTH0841 |
| NTH0843 | NTH0844 | NTH0848 | NTH0849 | NTH0850 | NTH0851 | NTH0852 | NTH0856 |
| NTH0858 | NTH0861 | NTH0862 | NTH0863 | NTH0864 | NTH0865 | NTH0866 | NTH0867 |
| NTH0872 | NTH0874 | NTH0875 | NTH0877 | NTH0879 | NTH0880 | NTH0885 | NTH0886 |
| NTH0887 | NTH0888 | NTH0892 | NTH0894 | NTH0895 | NTH0896 | NTH0900 | NTH0901 |
| NTH0904 | NTH0906 | NTH0909 | NTH0910 | NTH0913 | NTH0914 | NTH0921 | NTH0924 |
| NTH0926 | NTH0927 | NTH0928 | NTH0929 | NTH0930 | NTH0931 | NTH0932 | NTH0933 |
| NTH0937 | NTH0938 | NTH0941 | NTH0942 | NTH0948 | NTH0949 | NTH0950 | NTH0952 |
| NTH0953 | NTH0955 | NTH0961 | NTH0964 | NTH0968 | NTH0970 | NTH0971 | NTH0972 |
| NTH0973 | NTH0985 | NTH0986 | NTH0987 | NTH0989 | NTH0991 | NTH0992 | NTH0993 |
| NTH0994 | NTH0995 | NTH0996 | NTH0997 | NTH1000 | NTH1002 | NTH1003 | NTH1004 |
| NTH1005 | NTH1007 | NTH1009 | NTH1010 | NTH1012 | NTH1015 | NTH1016 | NTH1017 |
| NTH1018 | NTH1020 | NTH1021 | NTH1025 | NTH1026 | NTH1027 | NTH1028 | NTH1029 |
| NTH1031 | NTH1032 | NTH1037 | NTH1039 | NTH1040 | NTH1042 | NTH1043 | NTH1048 |
| NTH1049 | NTH1052 | NTH1054 | NTH1058 | NTH1063 | NTH1064 | NTH1067 | NTH1069 |
| NTH1070 | NTH1073 | NTH1075 | NTH1080 | NTH1082 | NTH1083 | NTH1084 | NTH1085 |
| NTH1086 | NTH1087 | NTH1089 | NTH1090 | NTH1091 | NTH1092 | NTH1098 | NTH1102 |
| NTH1103 | NTH1104 | NTH1106 | NTH1108 | NTH1111 | NTH1112 | NTH1114 | NTH1115 |
| NTH1116 | NTH1121 | NTH1122 | NTH1123 | NTH1124 | NTH1125 | NTH1129 | NTH1130 |
| NTH1131 | NTH1138 | NTH1141 | NTH1142 | NTH1149 | NTH1150 | NTH1151 | NTH1153 |
| NTH1157 | NTH1159 | NTH1161 | NTH1162 | NTH1164 | NTH1174 | NTH1176 | NTH1178 |
| NTH1179 | NTH1181 | NTH1184 | NTH1185 | NTH1188 | NTH1189 | NTH1190 | NTH1191 |
| NTH1192 | NTH1193 | NTH1195 | NTH1196 | NTH1200 | NTH1201 | NTH1203 | NTH1204 |
| NTH1205 | NTH1207 | NTH1208 | NTH1209 | NTH1210 | NTH1211 | NTH1214 | NTH1216 |
| NTH1220 | NTH1221 | NTH1224 | NTH1225 | NTH1226 | NTH1229 | NTH1230 | NTH1231 |
| NTH1233 | NTH1234 | NTH1235 | NTH1236 | NTH1237 | NTH1238 | NTH1240 | NTH1241 |
| NTH1244 | NTH1245 | NTH1246 | NTH1247 | NTH1248 | NTH1249 | NTH1250 | NTH1251 |
| NTH1252 | NTH1253 | NTH1254 | NTH1255 | NTH1256 | NTH1261 | NTH1262 | NTH1268 |
| NTH1270 | NTH1271 | NTH1273 | NTH1275 | NTH1279 | NTH1280 | NTH1281 | NTH1282 |
| NTH1283 | NTH1286 | NTH1287 | NTH1290 | NTH1293 | NTH1294 | NTH1295 | NTH1297 |
| NTH1298 | NTH1299 | NTH1300 | NTH1301 | NTH1302 | NTH1305 | NTH1306 | NTH1307 |
| NTH1308 | NTH1309 | NTH1311 | NTH1313 | NTH1315 | NTH1316 | NTH1319 | NTH1321 |
| NTH1325 | NTH1327 | NTH1330 | NTH1332 | NTH1333 | NTH1334 | NTH1336 | NTH1337 |
| NTH1339 | NTH1341 | NTH1342 | NTH1346 | NTH1348 | NTH1353 | NTH1354 | NTH1357 |
| NTH1359 | NTH1361 | NTH1363 | NTH1365 | NTH1367 | NTH1368 | NTH1374 | NTH1375 |
| NTH1376 | NTH1379 | NTH1380 | NTH1381 | NTH1382 | NTH1383 | NTH1388 | NTH1390 |
| NTH1391 | NTH1393 | NTH1394 | NTH1395 | NTH1396 | NTH1398 | NTH1399 | NTH1400 |
| NTH1406 | NTH1407 | NTH1411 | NTH1412 | NTH1413 | NTH1414 | NTH1415 | NTH1416 |
| NTH1418 | NTH1419 | NTH1420 | NTH1421 | NTH1425 | NTH1427 | NTH1428 | NTH1429 |
| NTH1430 | NTH1431 | NTH1434 | NTH1435 | NTH1437 | NTH1438 | NTH1439 | NTH1441 |
| NTH1447 | NTH1448 | NTH1450 | NTH1454 | NTH1455 | NTH1456 | NTH1464 | NTH1467 |
| NTH1468 | NTH1470 | NTH1471 | NTH1472 | NTH1473 | NTH1474 | NTH1479 | NTH1487 |
| NTH1489 | NTH1490 | NTH1491 | NTH1492 | NTH1493 | NTH1494 | NTH1495 | NTH1496 |
| NTH1497 | NTH1500 | NTH1503 | NTH1504 | NTH1506 | NTH1510 | NTH1515 | NTH1516 |
| NTH1525 | NTH1526 | NTH1527 | NTH1528 | NTH1531 | NTH1532 | NTH1537 | NTH1538 |
| NTH1540 | NTH1541 | NTH1543 | NTH1548 | NTH1552 | NTH1555 | NTH1559 | NTH1562 |
| NTH1563 | NTH1564 | NTH1567 | NTH1569 | NTH1570 | NTH1571 | NTH1573 | NTH1574 |
| NTH1575 | NTH1580 | NTH1581 | NTH1582 | NTH1584 | NTH1586 | NTH1587 | NTH1588 |
| NTH1590 | NTH1594 | NTH1597 | NTH1598 | NTH1599 | NTH1600 | NTH1601 | NTH1602 |
| NTH1603 | NTH1605 | NTH1606 | NTH1607 | NTH1608 | NTH1609 | NTH1611 | NTH1612 |
| NTH1615 | NTH1616 | NTH1617 | NTH1618 | NTH1619 | NTH1620 | NTH1621 | NTH1622 |
| NTH1623 | NTH1625 | NTH1626 | NTH1627 | NTH1628 | NTH1629 | NTH1631 | NTH1634 |
| NTH1637 | NTH1638 | NTH1647 | NTH1652 | NTH1653 | NTH1654 | NTH1656 | NTH1657 |
| NTH1658 | NTH1662 | NTH1664 | NTH1666 | NTH1668 | NTH1671 | NTH1675 | NTH1676 |
| NTH1677 | NTH1680 | NTH1686 | NTH1687 | NTH1688 | NTH1689 | NTH1690 | NTH1692 |
| NTH1693 | NTH1697 | NTH1698 | NTH1701 | NTH1702 | NTH1703 | NTH1707 | NTH1712 |
| NTH1713 | NTH1718 | NTH1719 | NTH1722 | NTH1724 | NTH1725 | NTH1729 | NTH1732 |
| NTH1734 | NTH1735 | NTH1739 | NTH1740 | NTH1742 | NTH1744 | NTH1745 | NTH1748 |
| NTH1749 | NTH1751 | NTH1752 | NTH1753 | NTH1754 | NTH1755 | NTH1756 | NTH1757 |
| NTH1758 | NTH1759 | NTH1760 | NTH1765 | NTH1767 | NTH1769 | NTH1770 | NTH1773 |
| NTH1778 | NTH1779 | NTH1781 | NTH1782 | NTH1783 | NTH1788 | NTH1793 | NTH1795 |
| NTH1796 | NTH1798 | NTH1799 | NTH1803 | NTH1804 | NTH1805 | NTH1806 | NTH1807 |
| NTH1811 | NTH1812 | NTH1813 | NTH1815 | NTH1816 | NTH1817 | NTH1818 | NTH1819 |
| NTH1820 | NTH1821 | NTH1822 | NTH1824 | NTH1828 | NTH1829 | NTH1832 | NTH1833 |
| NTH1835 | NTH1836 | NTH1837 | NTH1842 | NTH1845 | NTH1849 | NTH1850 | NTH1854 |
| NTH1857 | NTH1859 | NTH1861 | NTH1865 | NTH1870 | NTH1871 | NTH1872 | NTH1873 |
| NTH1881 | NTH1882 | NTH1885 | NTH1888 | NTH1889 | NTH1891 | NTH1892 | NTH1896 |
| NTH1897 | NTH1898 | NTH1899 | NTH1900 | NTH1904 | NTH1906 | NTH1908 | NTH1910 |
| NTH1914 | NTH1916 | NTH1917 | NTH1919 | NTH1920 | NTH1921 | NTH1922 | NTH1923 |
| NTH1925 | NTH1927 | NTH1935 | NTH1939 | NTH1941 | NTH1942 | NTH1945 | NTH1946 |
| NTH1947 | NTH1948 | NTH1951 | NTH1953 | NTH1956 | NTH1958 | NTH1960 | NTH1962 |
| NTH1963 | NTH1964 | NTH1965 | NTH1966 | NTH1967 | NTH1968 | NTH1974 | NTH1978 |
| NTH1981 | NTH1986 | NTH1989 | NTH1992 | NTH1993 | NTH1994 | NTH1995 | NTH1996 |
| NTH1997 | NTH1998 | NTH1999 | NTH2001 | NTH2005 | NTH2008 | NTH2009 | NTH2010 |
| NTH2019 | NTH2024 | NTH2025 | NTH2031 | NTH2035 | NTH2038 | NTH2039 | NTH2040 |
| NTH2041 | NTH2043 | NTH2050 | NTH2052 | NTH2055 | NTH2056 | NTH2060 | NTH2062 |
| NTH2064 | NTH2065 | NTH2069 | NTH2070 | NTH2071 | NTH2073 | NTH2075 | NTH2078 |
| NTH2079 | NTH2081 | NTH2083 | NTH2089 | NTH2091 | NTH2092 | NTH2093 | NTH2094 |

TABLE II-continued

Preferred polypeptides

| | | | | | | | |
|---|---|---|---|---|---|---|---|
| NTH2095 | NTH2096 | NTH2097 | NTH2099 | NTH2101 | NTH2109 | NTH2110 | NTH2112 |
| NTH2113 | NTH2114 | NTH2115 | NTH2116 | NTH2117 | NTH2118 | NTH2119 | NTH2120 |
| NTH2122 | NTH2126 | NTH2128 | NTH2129 | NTH2130 | NTH2131 | NTH2133 | NTH2135 |
| NTH2136 | NTH2138 | NTH2142 | NTH2145 | NTH2146 | NTH2149 | NTH2150 | NTH2156 |
| NTH2159 | NTH2162 | NTH2163 | NTH2166 | NTH2169 | NTH2170 | NTH2173 | NTH2181 |
| NTH2183 | NTH2187 | NTH2191 | NTH2193 | NTH2195 | NTH2196 | NTH2197 | NTH2198 |
| NTH2199 | NTH2200 | NTH2204 | NTH2205 | NTH2206 | NTH2207 | NTH2209 | NTH2213 |
| NTH2216 | NTH2217 | NTH2219 | NTH2220 | NTH2221 | NTH2222 | NTH2223 | NTH2226 |
| NTH2227 | NTH2228 | NTH2229 | NTH2231 | NTH2232 | NTH2234 | NTH2235 | NTH2242 |
| NTH2243 | NTH2245 | NTH2247 | NTH2250 | NTH2251 | NTH2253 | NTH2256 | NTH2257 |
| NTH2258 | NTH2259 | NTH2262 | NTH2263 | NTH2266 | NTH2269 | NTH2273 | NTH2274 |
| NTH2277 | NTH2282 | NTH2284 | NTH2285 | NTH2287 | NTH2288 | NTH2291 | NTH2292 |
| NTH2296 | NTH2299 | NTH2305 | NTH2309 | NTH2315 | NTH2316 | NTH2318 | NTH2323 |
| NTH2324 | NTH2326 | NTH2327 | NTH2330 | NTH2332 | NTH2333 | NTH2342 | NTH2343 |
| NTH2344 | NTH2346 | NTH2347 | NTH2349 | NTH2352 | NTH2353 | NTH2356 | NTH2358 |
| NTH2361 | NTH2362 | NTH2363 | NTH2364 | NTH2365 | NTH2368 | NTH2369 | NTH2370 |
| NTH2371 | NTH2376 | NTH2377 | NTH2381 | NTH2382 | NTH2386 | NTH2388 | NTH2394 |
| NTH2398 | NTH2402 | NTH2405 | NTH2406 | NTH2407 | NTH2408 | NTH2414 | NTH2414 |
| NTH2422 | NTH2430 | NTH2432 | NTH2433 | NTH2434 | NTH2438 | NTH2442 | NTH2447 |
| NTH2448 | NTH2451 | NTH2455 | NTH2456 | NTH2457 | NTH2458 | NTH2460 | NTH2461 |
| NTH2463 | NTH2464 | NTH2466 | NTH2467 | NTH2468 | NTH2471 | NTH2472 | NTH2478 |
| NTH2480 | NTH2481 | NTH2482 | NTH2483 | NTH2484 | NTH2485 | NTH2486 | NTH2487 |
| NTH2488 | NTH2493 | NTH2495 | NTH2496 | NTH2497 | NTH2498 | NTH2499 | NTH2500 |
| NTH2501 | NTH2505 | NTH2508 | NTH2510 | NTH2524 | NTH2525 | NTH2527 | NTH2528 |
| NTH2531 | NTH2532 | NTH2533 | NTH2534 | NTH2536 | NTH2537 | NTH2541 | NTH2542 |
| NTH2543 | NTH2545 | NTH2546 | NTH2548 | NTH2549 | NTH2550 | NTH2552 | NTH2554 |
| NTH2556 | NTH2557 | NTH2558 | NTH2562 | NTH2563 | NTH2566 | NTH2567 | NTH2568 |
| NTH2569 | NTH2570 | NTH2572 | NTH2573 | NTH2575 | NTH2577 | NTH2578 | NTH2584 |
| NTH2585 | NTH2587 | NTH2588 | NTH2590 | NTH2591 | NTH2593 | NTH2595 | NTH2597 |
| NTH2600 | NTH2602 | NTH2603 | NTH2604 | NTH2605 | NTH2607 | NTH2608 | NTH2609 |
| NTH2610 | NTH2612 | NTH2613 | NTH2615 | NTH2616 | NTH2618 | NTH2626 | NTH2633 |
| NTH2635 | NTH2640 | NTH2641 | NTH2647 | NTH2648 | NTH2649 | NTH2650 | NTH2655 |
| NTH2661 | NTH2663 | NTH2664 | NTH2667 | NTH2668 | NTH2673 | NTH2674 | NTH2675 |
| NTH2679 | NTH2680 | NTH2684 | NTH2690 | NTH2693 | NTH2694 | NTH2696 | NTH2697 |
| NTH2701 | NTH2702 | NTH2703 | NTH2704 | NTH2705 | NTH2706 | NTH2707 | NTH2708 |
| NTH2709 | NTH2710 | NTH2711 | NTH2712 | NTH2713 | NTH2715 | NTH2716 | NTH2718 |
| NTH2719 | NTH2720 | NTH2721 | NTH2723 | NTH2724 | NTH2725 | NTH2726 | NTH2727 |
| NTH2729 | NTH2730 | NTH2731 | NTH2732 | NTH2735 | NTH2737 | NTH2738 | NTH2740 |
| NTH2743 | NTH2744 | NTH2749 | NTH2750 | NTH2753 | NTH2754 | NTH2755 | NTH2756 |
| NTH2757 | NTH2758 | NTH2764 | NTH2765 | NTH2769 | NTH2774 | NTH2777 | NTH2778 |
| NTH2779 | NTH2781 | NTH2783 | NTH2784 | NTH2785 | NTH2791 | NTH2793 | NTH2794 |
| NTH2796 | NTH2797 | NTH2798 | NTH2804 | NTH2806 | NTH2807 | NTH2809 | NTH2810 |
| NTH2813 | NTH2814 | NTH2816 | NTH2823 | | | | |

TABLE III

Annotations
aa = length of polypeptide
PSORT = cellular location of polypeptide, according to PSORT algorithm

| NTH | aa | PSORT | Annotation |
|---|---|---|---|
| 0003 | 274 | cytoplasm | Diaminopimelate epimerase (dapF) |
| 0007 | 61 | cytoplasm | tldD protein tldD |
| 0010 | 158 | cytoplasm | transcriptional regulator |
| 0011 | 93 | cytoplasm | usg-1 protein (usg1) |
| 0013 | 274 | cytoplasm | excinuclease ABC, subunit C (uvrC) |
| 0014 | 64 | periplasmic | excinuclease ABC, subunit C (uvrC) |
| 0017 | 161 | outer | 2',3'-cyclic-nucleotide 2'-phosphodiesterase (cpdB) |
| 0018 | 130 | cytoplasm | 16s pseudouridylate 516 synthase (rsuA) |
| 0019 | 98 | inner 1 | bicyclomycin resistance protein (bcr) |
| 0020 | 181 | inner 4 | Na(+)-translocating NADH-quinone reductase, subunit |
| 0023 | 110 | cytoplasm | sigma-E factor regulatory protein (rseB) |
| 0025 | 195 | inner 1 | sigma-E factor negative regulatory protein (mclA) |
| 0026 | 157 | cytoplasm | RNA polymerase sigma-E factor (rpoE) |
| 0027 | 100 | cytoplasm | cell division protein (ftsQ) |
| 0028 | 37 | cytoplasm | cell division protein (ftsA) |
| 0029 | 34 | cytoplasm | cell division protein (ftsA) |
| 0030 | 268 | cytoplasm | aspartate--ammonia ligase (asnA) |
| 0039 | 311 | cytoplasm | ADP-heptose--LPS heptosyltransferase II (rfaF) |
| 0043 | 194 | inner 3 | sodium:dicarboxylate symporter protein |
| 0044 | 79 | cytoplasm | ferritin (rsgA) |
| 0047 | 219 | cytoplasm | heat shock protein (hslU)/ATP-dependent Clp protease, ATP-binding subunit |
| 0048 | 55 | inner 2 | L-lactate permease (lctP) |
| 0049 | 90 | periplasmic | transferrin-binding protein or TonB-dependent receptor |

TABLE III-continued

Annotations
aa = length of polypeptide
PSORT = cellular location of polypeptide, according to PSORT algorithm

| NTH | aa | PSORT | Annotation |
| --- | --- | --- | --- |
| 0055 | 92 | cytoplasm | heat shock protein (hslV) |
| 0057 | 235 | periplasmic | acid phosphatase |
| 0058 | 206 | cytoplasm | rod shape-determining protein (mreB) or cell division protein FtsA ftsA |
| 0059 | 54 | periplasmic | rod shape-determining protein (mreC) |
| 0060 | 104 | inner 0 | ribosomal protein S8 (rpS8) |
| 0061 | 313 | inner 2 | ribosomal protein L6 (rpL6) |
| 0063 | 257 | cytoplasm | fumarate (and nitrate) reduction regulatory protein (fnr) |
| 0065 | 266 | cytoplasm | thiamin ABC transporter, periplasmic-binding protein (tbpA) |
| 0067 | 86 | inner 1 | thiamin ABC transporter, permease protein |
| 0068 | 52 | cytoplasm | UDP-N-acetylenolpyruvoylglucosamine reductase (murB) |
| 0069 | 149 | cytoplasm | RNA polymerase sigma-32 factor (rpoH) |
| 0070 | 127 | cytoplasm | RNA polymerase sigma-32 factor (rpoH) |
| 0071 | 64 | cytoplasm | NifR3/SMM1 family protein |
| 0072 | 201 | cytoplasm | acetolactate synthase III large subunit (ilvI) |
| 0073 | 142 | inner 1 | acetolactate synthase III large subunit (ilvI) |
| 0075 | 166 | cytoplasm | acetolactate synthase III small subunit (ilvH) |
| 0078 | 119 | cytoplasm | orotate phosphoribosyltransferase (pyrE) |
| 0079 | 36 | cytoplasm | orotate phosphoribosyltransferase (pyrE) |
| 0082 | 144 | cytoplasm | DNA polymerase III, chi subunit (holC) |
| 0083 | 85 | cytoplasm | methylglyoxal synthase (mgsA) |
| 0085 | 340 | inner 7 | cytochrome C-type biogenesis protein (ccmF) |
| 0086 | 45 | cytoplasm | cytochrome C-type biogenesis protein (ccmE) |
| 0087 | 312 | cytoplasm | histidyl-tRNA synthetase (hisS) |
| 0088 | 214 | cytoplasm | topoisomerase IV, subunit A (parC) |
| 0091 | 212 | inner 1 | 4-hydroxy-2-oxoglutarate |
| 0094 | 338 | lipo | zinc protease |
| 0098 | 358 | cytoplasm | homoserine O-acetyltransferase (met2) |
| 0099 | 60 | cytoplasm | DNA gyrase, subunit A (gyrA) |
| 0100 | 56 | cytoplasm | DNA gyrase, subunit A (gyrA) |
| 0102 | 102 | cytoplasm | universal stress protein A (uspA) |
| 0103 | 290 | cytoplasm | alanyl-tRNA synthetase (alaS) |
| 0104 | 81 | cytoplasm | alanyl-tRNA synthetase (alaS) |
| 0105 | 557 | cytoplasm | protective surface antigen D15 (Omp85) |
| 0106 | 110 | periplasmic | outer membrane protein |
| 0107 | 257 | inner 1 | cell division protein (ftsZ) |
| 0108 | 352 | cytoplasm | cell division protein (ftsA) |
| 0109 | 496 | cytoplasm | DNA topoisomerase I (topA) |
| 0112 | 259 | cytoplasm | penicillin-binding protein 1B (ponB) |
| 0113 | 35 | cytoplasm | penicillin-binding protein 1B (ponB) |
| 0115 | 279 | cytoplasm | penicillin-binding protein 1A (ponA) |
| 0116 | 310 | inner 1 | GTP-binding protein |
| 0117 | 243 | cytoplasm | phosphomannomutase (yhxB) |
| 0118 | 84 | inner 0 | phosphomannomutase (yhxB) |
| 0119 | 89 | periplasmic | tonB protein |
| 0120 | 147 | periplasmic | biopolymer transport protein (exbD) |
| 0121 | 49 | inner 1 | biopolymer transport protein (exbB) |
| 0126 | 77 | cytoplasm | integrase/recombinase |
| 0128 | 111 | inner 1 | xanthine-guanine phosphoribosyltransferase (gptB) |
| 0130 | 184 | cytoplasm | aminoacyl-histidine dipeptidase (pepD) |
| 0131 | 35 | cytoplasm | aminoacyl-histidine dipeptidase (pepD) |
| 0134 | 182 | inner 1 | phosphoribosylglycinamide formyltransferase (purN) |
| 0137 | 58 | cytoplasm | GTP-binding membrane protein (lepA) |
| 0141 | 78 | cytoplasm | uracil DNA glycosylase (ung) |
| 0142 | 76 | cytoplasm | aldose 1-epimerase (galM) |
| 0143 | 129 | cytoplasm | galactokinase (galK) |
| 0144 | 197 | cytoplasm | galactokinase (galK) |
| 0145 | 346 | cytoplasm | GTP-binding protein TypA |
| 0147 | 179 | cytoplasm | queuine tRNA-ribosyltransferase (tgt) |
| 0150 | 239 | cytoplasm | ribosomal large subunit pseudouridine synthase C |
| 0152 | 463 | cytoplasm | galactoside ABC transporter, ATP-binding protein (mglA) |
| 0153 | 247 | cytoplasm | hemagglutinin/hemolysin-related protein |
| 0154 | 240 | cytoplasm | hemagglutinin/hemolysin-related protein |
| 0155 | 302 | inner 7 | phosphate permease |
| 0157 | 124 | inner 2 | cytochrome D ubiquinol oxidase, subunit I (cydA) or iron(III) ABC transporter, permease protein fbpB |
| 0158 | 103 | inner 2 | cytochrome D ubiquinol oxidase, subunit II (cydB) |
| 0163 | 154 | lipo | 15 kDa peptidoglycan-associated lipoprotein (lpp) |
| 0165 | 165 | cytoplasm | membrane-bound lytic murein transglycosylase C (mltC) |
| 0167 | 194 | lipo | membrane-bound lytic murein transglycosylase C (mltC) |
| 0170 | 51 | cytoplasm | hflK protein (hflK) |
| 0174 | 40 | periplasmic | tail specific protease (prc) |
| 0178 | 116 | cytoplasm | recombination protein (rec2) or competence protein ComA comA |
| 0180 | 147 | inner 2 | ABC transporter, ATP-binding protein (msbA) |
| 0185 | 220 | inner 0 | chorismate synthase (aroC) |

TABLE III-continued

Annotations
aa = length of polypeptide
PSORT = cellular location of polypeptide, according to PSORT algorithm

| NTH | aa | PSORT | Annotation |
|---|---|---|---|
| 0186 | 156 | inner 2 | ATP-binding transport protein (cydD) |
| 0189 | 162 | inner 2 | rod shape-determining protein (mreD) |
| 0190 | 188 | periplasmic | rod shape-determining protein (mreC) |
| 0196 | 68 | cytoplasm | sigma factor |
| 0200 | 68 | cytoplasm | mercuric ion scavenger protein (merP) |
| 0201 | 68 | cytoplasm | mercuric ion scavenger protein (merP) |
| 0202 | 68 | cytoplasm | mercuric ion scavenger protein (merP) |
| 0203 | 63 | inner 0 | orfJ protein |
| 0204 | 306 | cytoplasm | penicillin-binding protein 1A (ponA) |
| 0205 | 38 | cytoplasm | penicillin-binding protein 1A (ponA) |
| 0207 | 175 | cytoplasm | extragenic suppressor (suhB) |
| 0208 | 64 | inner 1 | cytochrome C-type biogenesis |
| 0209 | 117 | inner 2 | 1,4-dihydroxy-2-naphthoate octaprenyltransferase (menA) |
| 0212 | 203 | cytoplasm | lysyl-tRNA synthetase analog (genX) |
| 0215 | 204 | cytoplasm | fumarate reductase, flavoprotein subunit (frdA) or succinate dehydrogenase, flavoprotein subunit sdhA |
| 0216 | 48 | cytoplasm | fumarate reductase, flavoprotein subunit (frdA) |
| 0217 | 40 | cytoplasm | fumarate reductase, flavoprotein subunit (frdA) |
| 0218 | 310 | cytoplasm | nitrogen fixation protein (nifR3) |
| 0220 | 99 | cytoplasm | Hin recombinational enhancer binding protein (fis) or factor-for-inversion stimulation protein Fis, |
| 0221 | 48 | cytoplasm | small protein B (smpB) |
| 0222 | 222 | cytoplasm | magnesium and cobalt transport protein (corA) |
| 0223 | 91 | inner 1 | magnesium and cobalt transport protein (corA) |
| 0225 | 426 | cytoplasm | exoribonuclease II (rnb) or ribonuclease II family protein vacB |
| 0233 | 114 | cytoplasm | uridylate kinase (pyrH) |
| 0234 | 41 | cytoplasm | uridylate kinase (pyrH) |
| 0236 | 35 | cytoplasm | phospho-2-dehydro-3-deoxyheptonate aldolase (phenylalanine |
| 0239 | 322 | cytoplasm | heat shock (chaperone) protein (hscA) |
| 0240 | 44 | cytoplasm | heat shock (chaperone) protein (hscA) |
| 0241 | 193 | outer | usg-1 protein (usg1) |
| 0242 | 268 | inner 2 | tryptophan synthase alpha subunit (trpA) |
| 0243 | 58 | cytoplasm | tryptophan synthase beta subunit (trpB) |
| 0244 | 245 | periplasmic | stationary phase survival protein SurA or peptidyl-prolyl cis-trans isomerase |
| 0245 | 191 | cytoplasm | pyrimidine operon regulatory protein (pyrR) or hypoxanthine-guanine phosphoribosyltransferase, |
| 0246 | 153 | cytoplasm | mazG protein (mazG) |
| 0247 | 159 | inner 3 | ATP synthase F0, subunit a (atpB) |
| 0249 | 203 | cytoplasm | glucose-inhibited division protein (gidB) |
| 0257 | 289 | cytoplasm | selenocysteine-specific elongation factor (selB) |
| 0258 | 212 | cytoplasm | pyruvate dehydrogenase, E1 component (aceE) |
| 0259 | 61 | cytoplasm | pyruvate dehydrogenase, E1 component (aceE) |
| 0260 | 505 | cytoplasm | ribonuclease E (rne) |
| 0262 | 303 | cytoplasm | ATP-dependent helicase (dinG) |
| 0263 | 276 | inner 7 | thiamin ABC transporter, permease protein |
| 0266 | 121 | cytoplasm | N utilization substance protein B (nusB) |
| 0267 | 160 | cytoplasm | thiamin-monophosphate kinase (thiL) |
| 0268 | 144 | cytoplasm | thiamin-monophosphate kinase (thiL) |
| 0269 | 163 | inner 3 | phosphatidylglycerophosphatase A (pgpA) |
| 0272 | 44 | cytoplasm | ribosomal protein L34 (rpL34) |
| 0273 | 119 | cytoplasm | ribonuclease P (rnpA) |
| 0275 | 146 | cytoplasm | impA protein |
| 0277 | 218 | cytoplasm | phospho-2-dehydro-3-deoxyheptonate aldolase (phenylalanine |
| 0286 | 288 | cytoplasm | GTP-binding protein |
| 0287 | 422 | cytoplasm | formate dehydrogenase, beta subunit (fdxH) or ferredoxin, 4Fe—4S bacterial type |
| 0291 | 109 | cytoplasm | mannonate dehydratase (uxuA) |
| 0292 | 46 | cytoplasm | mannonate dehydratase (uxuA) |
| 0294 | 171 | cytoplasm | dihydroxyacid dehydratase (ilvD) |
| 0295 | 308 | inner 1 | threonine deaminase (ilvA) |
| 0296 | 239 | cytoplasm | galactose-1-phosphate uridylyltransferase (galT) |
| 0303 | 283 | cytoplasm | hemoglobin-binding protein |
| 0304 | 68 | cytoplasm | ribosomal protein L24 (rpL24) |
| 0305 | 123 | cytoplasm | ribosomal protein L14 (rpL14) |
| 0309 | 82 | cytoplasm | inorganic pyrophosphatase (ppa) |
| 0311 | 185 | inner 4 | phosphatidylglycerophosphate synthase (pgsA) or CDP-diacylglycerol--glycerol-3-phosphate |
| 0314 | 274 | cytoplasm | dihydrolipoamide dehydrogenase (lpdA) or pyruvate dehydrogenase, E3 component, lipoamide |
| 0315 | 38 | cytoplasm | dihydrolipoamide dehydrogenase (lpdA) |
| 0318 | 358 | cytoplasm | DNA topoisomerase III (topB) or DNA topoisomerase I topA |
| 0320 | 411 | inner 1 | Nqr6 subunit of Na-translocating NADH-quinone reductase |
| 0321 | 191 | inner 1 | single-stranded DNA binding protein (ssb) |
| 0323 | 141 | cytoplasm | excinuclease ABC, subunit A (uvrA) |

TABLE III-continued

Annotations
aa = length of polypeptide
PSORT = cellular location of polypeptide, according to PSORT algorithm

| NTH | aa | PSORT | Annotation |
|---|---|---|---|
| 0324 | 319 | cytoplasm | type IV pilus assembly protein pilF |
| 0325 | 200 | inner 1 | pilus assembly protein PilG pilG |
| 0326 | 386 | inner 8 | branched chain amino acid transport system II carrier |
| 0329 | 395 | cytoplasm | cystathionine beta-lyase (metC) or trans-sulfuration enzyme family protein |
| 0330 | 109 | cytoplasm | sanA protein (sanA) |
| 0333 | 96 | inner 1 | folylpolyglutamate synthase/dihydrofolate synthase (folC) |
| 0336 | 133 | cytoplasm | short chain dehydrogenase/reductase or oxidoreductase, short-chain dehydrogenase/reductase |
| 0337 | 391 | cytoplasm | tryptophan synthase beta subunit (trpB) |
| 0340 | 151 | cytoplasm | cell division protein (ftsH) |
| 0342 | 147 | cytoplasm | peptide methionine sulfoxide reductase pilB |
| 0346 | 46 | periplasmic | small protein A |
| 0347 | 273 | inner 7 | transport protein |
| 0349 | 66 | cytoplasm | protease |
| 0351 | 412 | inner 1 | penicillin-binding protein 1B (ponB) |
| 0352 | 291 | inner 5 | carbon starvation protein A cstA |
| 0354 | 227 | cytoplasm | GTP pyrophosphokinase (relA) |
| 0355 | 367 | cytoplasm | GTP pyrophosphokinase (relA) |
| 0356 | 65 | inner 1 | diacylglycerol kinase (dgkA) |
| 0358 | 56 | inner 1 | diacylglycerol kinase (dgkA) |
| 0359 | 275 | cytoplasm | esterase |
| 0360 | 216 | cytoplasm | UDP-3-O-(3-hydroxymyristoyl)-glucosamine N-acyltransferase |
| 0361 | 141 | cytoplasm | translation elongation factor Ts (tsf) (EF-TS) |
| 0365 | 91 | cytoplasm | exodeoxyribonuclease III (xthA) |
| 0366 | 432 | inner 1 | heme-hemopexin utilization protein A (hxuA) |
| 0367 | 184 | cytoplasm | carboxy-terminal tail specific protease (prc) |
| 0368 | 204 | cytoplasm | carboxy-terminal tail specific protease (prc) |
| 0369 | 163 | cytoplasm | dihydroxyacid dehydratase (ilvD) |
| 0370 | 201 | cytoplasm | acetohydroxy acid synthase II or acetolactate synthase III, large subunit ilvI |
| 0372 | 306 | inner 7 | sodium-dependent transporter or sodium- and chloride-dependent transporter |
| 0373 | 42 | cytoplasm | aminotransferase |
| 0374 | 307 | cytoplasm | aminotransferase |
| 0376 | 128 | cytoplasm | ribosomal protein L17 (rplQ) |
| 0377 | 193 | cytoplasm | DNA-directed RNA polymerase, alpha chain (rpoA) |
| 0380 | 33 | cytoplasm | acylneuraminate cytidylyltransferase (neuA) |
| 0382 | 359 | cytoplasm | peptidyl-prolyl cis-trans isomerse |
| 0386 | 111 | cytoplasm | DNA gyrase, subunit A (gyrA) |
| 0387 | 52 | cytoplasm | DNA gyrase, subunit A (gyrA) |
| 0388 | 242 | inner 3 | sodium/proline symporter (proline permease) (putP) |
| 0391 | 256 | cytoplasm | anaerobic ribonucleoside-triphosphate reductase (nrdD) |
| 0392 | 87 | cytoplasm | anaerobic ribonucleoside-triphosphate reductase (nrdD) |
| 0393 | 211 | cytoplasm | aminotransferase |
| 0394 | 117 | cytoplasm | aerobic respiration control protein ARCA (arcA) or DNA-binding response regulator |
| 0397 | 444 | inner 8 | thiol:disulfide interchange protein (dsbD) |
| 0399 | 362 | cytoplasm | GTP-binding membrane protein (lepA) |
| 0400 | 437 | inner 9 | sodium-dependent transporter |
| 0401 | 206 | inner 5 | nitrite reductase, transmembrane protein (nrfD) |
| 0402 | 138 | inner 3 | cytochrome C-type biogenesis protein or thiol:disulfide interchange protein DsbD dsbD |
| 0403 | 84 | cytoplasm | peptide methionine sulfoxide reductase (msrA) |
| 0405 | 299 | periplasmic | peptide methionine sulfoxide reductase (msrA) |
| 0418 | 297 | inner 3 | cytochrome D ubiquinol oxidase, subunit I (cydA) |
| 0421 | 287 | periplasmic | CTP synthetase (pyrG) |
| 0423 | 385 | cytoplasm | exodeoxyribonuclease VII, large subunit (xseA) |
| 0425 | 92 | cytoplasm | oligopeptide ABC transporter, ATP-binding protein (oppD) |
| 0426 | 311 | inner 6 | oligopeptide ABC transporter, permease protein (oppC) |
| 0427 | 232 | inner 6 | oligopeptide ABC transporter, permease protein (oppB) or iron(III) ABC transporter, permease protein |
| 0428 | 316 | cytoplasm | cysteine synthetase (cysK) |
| 0431 | 116 | cytoplasm | C-5 cytosine-specific DNA-methylase |
| 0436 | 341 | cytoplasm | peptide chain release factor 3 (prfC) |
| 0437 | 295 | inner 1 | enoyl-(acyl-carrier-protein) reductase (fabI) |
| 0441 | 66 | cytoplasm | L-2,4-diaminobutyrate decarboxylase |
| 0442 | 222 | cytoplasm | formamidopyrimidine-DNA glycosylase (fpg) |
| 0443 | 160 | cytoplasm | peptidase T (pepT) |
| 0444 | 178 | inner 0 | fuculokinase (fucK) |
| 0447 | 323 | cytoplasm | L-fucose isomerase (fucI) |
| 0448 | 119 | cytoplasm | L-fucose isomerase (fucI) |
| 0449 | 193 | cytoplasm | dethiobiotin synthase (bioD-1) |
| 0451 | 88 | cytoplasm | GTP cyclohydrolase I (folE) |
| 0453 | 113 | inner 1 | GTP cyclohydrolase I (folE) |
| 0454 | 78 | cytoplasm | GTP cyclohydrolase I (folE) |

TABLE III-continued

Annotations
aa = length of polypeptide
PSORT = cellular location of polypeptide, according to PSORT algorithm

| NTH | aa | PSORT | Annotation |
|---|---|---|---|
| 0456 | 212 | cytoplasm | protein-PII uridylyl transferase (glnD) |
| 0457 | 288 | inner 9 | undecaprenyl-phosphate alpha-N-acetylglucosaminyltransferase or phospho-N-acetylmuramoyl-pentapeptide-transferase |
| 0458 | 293 | cytoplasm | penicillin tolerance protein (lytB) |
| 0459 | 57 | inner 1 | lipoprotein signal peptidase (lspA) |
| 0460 | 122 | inner 1 | lipoprotein signal peptidase (lspA) |
| 0461 | 433 | inner 2 | YhbX/YhjW/YijP/YjdB family protein |
| 0462 | 107 | inner 2 | transporter protein |
| 0463 | 159 | inner 3 | transporter protein |
| 0464 | 349 | cytoplasm | 2',3'-cyclic-nucleotide 2'-phosphodiesterase (cpdB) |
| 0465 | 73 | inner 1 | iron (chelated) ABC transporter, permease protein (yfeD) |
| 0467 | 215 | cytoplasm | transcriptional activator |
| 0468 | 314 | periplasmic | thiamine biosynthesis protein |
| 0469 | 76 | inner 1 | ABC transporter, permease protein |
| 0470 | 328 | cytoplasm | alanyl-tRNA synthetase (alaS) |
| 0472 | 122 | cytoplasm | alanyl-tRNA synthetase (alaS) |
| 0473 | 89 | inner 0 | phosphatidylserine decarboxylase proenzyme (psd) |
| 0474 | 261 | cytoplasm | glutathione reductase (gor) or 2-oxoglutarate dehydrogenase, E3 component, |
| 0475 | 241 | inner 5 | phosphatidylglycerophosphatase B (pgpB) |
| 0476 | 119 | cytoplasm | GTP cyclohydrolase II (ribA) |
| 0477 | 153 | cytoplasm | DNA polymerase III, delta subunit (holA) |
| 0479 | 369 | cytoplasm | glycyl-tRNA synthetase, beta chain (glyS) |
| 0480 | 305 | cytoplasm | UDP-3-0-(3-hydroxymyristoyl) N-acetylglucosamine deacetylase |
| 0481 | 116 | cytoplasm | chorismate mutase/prephenate dehydratase (pheA) |
| 0483 | 271 | cytoplasm | urease accessory protein (ureH) |
| 0490 | 179 | inner 4 | glutamate permease (gltS) sodium/glutamate symporter |
| 0492 | 95 | cytoplasm | ribosomal protein S6 modification protein (rimK) or glutathione synthetase gshB |
| 0493 | 123 | inner 2 | Na+/H+ antiporter (nhaC) |
| 0494 | 326 | cytoplasm | xylose operon regluatory protein (xylR) |
| 0495 | 144 | cytoplasm | lipopolysaccharide biosynthesis protein or lacto-N-neotetraose biosynthesis glycosyl |
| 0496 | 257 | inner 1 | lipopolysaccharide biosynthesis protein |
| 0502 | 46 | outer | penicillin-binding protein 7 |
| 0503 | 138 | cytoplasm | transcription elongation factor (greA) |
| 0504 | 115 | outer | D-alanyl-D-alanine |
| 0505 | 370 | cytoplasm | D-alanyl-D-alanine or penicillin-binding protein 3 |
| 0506 | 38 | cytoplasm | IS1016 family transposase |
| 0507 | 158 | inner 1 | IS1016-V6 protein (IS1016-V6) |
| 0508 | 111 | cytoplasm | IS1016C2 transposase |
| 0514 | 296 | cytoplasm | aminopeptidase A/I (pepA) |
| 0515 | 113 | cytoplasm | stringent starvation protein B (sspB) |
| 0517 | 312 | cytoplasm | 1-deoxyxylulose-5-phosphate synthase (dxs) |
| 0518 | 150 | inner 0 | short chain dehydrogenase/reductase |
| 0519 | 348 | cytoplasm | phosphoribosylaminoimidazole synthetase (purM) |
| 0521 | 40 | cytoplasm | phosphoglycerate mutase (gpmA) |
| 0522 | 70 | cytoplasm | ribosomal protein L31 (rpL31) |
| 0524 | 158 | inner 0 | A/G-specific adenine glycosylase (mutY) |
| 0525 | 86 | cytoplasm | A/G-specific adenine glycosylase (mutY) |
| 0528 | 170 | inner 2 | formate dehydrogenase, gamma subunit (fdxI) |
| 0529 | 319 | inner 2 | fdhE protein (fdhE) |
| 0530 | 137 | cytoplasm | DNA transformation protein (sxy) |
| 0532 | 571 | cytoplasm | immunoglobin A1 protease (iga1) or hemagglutinin/hemolysin-related protein |
| 0535 | 289 | cytoplasm | threonyl-tRNA synthetase (thrS) |
| 0540 | 184 | cytoplasm | competence protein E (comE) |
| 0542 | 213 | cytoplasm | competence protein F (comF) |
| 0543 | 220 | cytoplasm | hflK protein (hflK) or stomatin/Mec-2 family protein |
| 0544 | 295 | inner 1 | hflC protein (hflC) or stomatin/Mec-2 family protein |
| 0547 | 74 | periplasmic | sodium/proline symporter (proline permease) (putP) |
| 0548 | 304 | cytoplasm | cytoplasmic axial filament protein (cafA) |
| 0549 | 108 | inner 1 | cytoplasmic axial filament protein (cafA) |
| 0550 | 93 | cytoplasm | cytoplasmic axial filament protein (cafA) |
| 0552 | 217 | cytoplasm | cell division protein (mukB) |
| 0554 | 248 | cytoplasm | killing protein suppressor (kicA) |
| 0557 | 245 | cytoplasm | fdhD protein (fdhD) |
| 0558 | 38 | cytoplasm | fdhD protein (fdhD) |
| 0560 | 30 | cytoplasm | phosphatidylserine decarboxylase proenzyme (psd) |
| 0563 | 56 | cytoplasm | ribosomal protein L32 (rpL32) |
| 0564 | 225 | cytoplasm | beta-ketoacyl-ACP synthase III (fabH) or 3-oxoacyl-(acyl-carrier-protein) synthase III fabH |
| 0565 | 368 | inner 7 | tryptophan-specific transport protein (mtr) |
| 0566 | 409 | inner 1 | L-serine deaminase (sdaA) |

TABLE III-continued

Annotations
aa = length of polypeptide
PSORT = cellular location of polypeptide, according to PSORT algorithm

| NTH | aa | PSORT | Annotation |
|---|---|---|---|
| 0571 | 292 | cytoplasm | cytidine deaminase (cdd) |
| 0574 | 212 | inner 2 | lipoprotein |
| 0575 | 65 | cytoplasm | transcriptional regulator (bolA) |
| 0576 | 158 | cytoplasm | NADH:ubiquinone oxidoreducatase subunit A, Na translocating or Na(+)-translocating NADH-quinone reductase, subunit |
| 0580 | 160 | inner 0 | translation initiation factor 2 (infB) |
| 0591 | 200 | cytoplasm | beta-phosphoglucomutase pgmB |
| 0592 | 462 | cytoplasm | cell division protein (mukB) |
| 0594 | 393 | cytoplasm | traN-related protein |
| 0595 | 31 | cytoplasm | GTP cyclohydrolase II (ribA) |
| 0596 | 57 | cytoplasm | GTP cyclohydrolase II (ribA) |
| 0597 | 345 | cytoplasm | oligopeptide transporter, periplasmic-binding protein, |
| 0599 | 32 | cytoplasm | oligopeptide transporter, periplasmic-binding protein, |
| 0601 | 240 | cytoplasm | aminopeptidase P (pepP) |
| 0604 | 37 | cytoplasm | aldose 1-epimerase (galM) |
| 0605 | 195 | cytoplasm | aldose 1-epimerase (galM) |
| 0607 | 318 | cytoplasm | C-5 cytosine-specific DNA-methylase |
| 0608 | 104 | cytoplasm | killing protein (kicB) |
| 0609 | 144 | cytoplasm | DNA polymerase III, delta subunit (holA) |
| 0611 | 69 | cytoplasm | rare lipoprotein B |
| 0613 | 75 | cytoplasm | transcriptional regulator (nadR) |
| 0614 | 310 | cytoplasm | transcriptional regulator (nadR) |
| 0616 | 69 | cytoplasm | aerobic respiration control protein ARCA (arcA) |
| 0618 | 368 | inner 7 | sodium/alanine symporter |
| 0619 | 303 | periplasmic | elongation factor Tu (tufB) |
| 0622 | 218 | inner 4 | dedA protein |
| 0626 | 164 | inner 5 | lic-1 operon protein (licB) |
| 0627 | 321 | cytoplasm | lic-1 operon protein (licA) |
| 0628 | 235 | cytoplasm | UDP-N-acetylenolpyruvoylglucosamine reductase (murB) |
| 0629 | 179 | cytoplasm | nitrate/nitrite sensor protein (narQ) |
| 0630 | 151 | inner 1 | small major protein B (smpB) |
| 0632 | 53 | cytoplasm | 6-phosphofructokinase (pfkA) |
| 0633 | 290 | cytoplasm | 6-phosphofructokinase (pfkA) |
| 0635 | 355 | cytoplasm | type I modification enzyme (hsdM) |
| 0636 | 158 | inner 2 | cysteine synthetase (cysZ) |
| 0638 | 328 | outer | cell division protein ZipA |
| 0640 | 122 | cytoplasm | ribosomal protein S12 (rps12) |
| 0641 | 346 | cytoplasm | glucose inhibited division protein (gidA) |
| 0646 | 257 | inner 5 | Na+/H+ antiporter (nhaC) |
| 0647 | 37 | outer | Na+/H+ antiporter (nhaC) |
| 0648 | 362 | outer | colicin tolerance protein (tolB) |
| 0650 | 497 | cytoplasm | cell division protein (mukB) |
| 0651 | 391 | cytoplasm | heme-binding lipoprotein (dppA) |
| 0652 | 78 | cytoplasm | octaprenyl-diphosphate synthase (ispB) |
| 0654 | 103 | inner 1 | ribosomal protein L21 (rpL21) |
| 0655 | 85 | cytoplasm | ribosomal protein L27 (rpL27) |
| 0657 | 83 | cytoplasm | GTP-binding protein (yhbZ) |
| 0658 | 75 | inner 1 | lipopolysaccharide biosynthesis protein |
| 0659 | 55 | cytoplasm | lipopolysaccharide biosynthesis protein |
| 0660 | 255 | cytoplasm | molybdenum transport protein (modE) |
| 0661 | 34 | periplasmic | molybdenum ABC transporter, periplasmic-binding protein |
| 0665 | 144 | cytoplasm | single-stranded DNA binding protein (ssb) |
| 0670 | 366 | cytoplasm | histidinol-phosphate aminotransferase (hisH) |
| 0671 | 31 | cytoplasm | phosphoserine aminotransferase (serC) |
| 0672 | 31 | cytoplasm | phosphoserine aminotransferase (serC) |
| 0674 | 140 | cytoplasm | ribosomal protein L3 (rpL3) |
| 0675 | 200 | inner 1 | ribosomal protein L4 (rpL4) |
| 0676 | 139 | inner 1 | ribosomal protein L23 (rpL23) |
| 0679 | 51 | cytoplasm | ampD signalling protein (ampD) |
| 0682 | 96 | cytoplasm | hemolysin |
| 0684 | 208 | cytoplasm | spermidine/putrescine ABC transporter, ATP-binding protein |
| 0685 | 52 | cytoplasm | lysyl-tRNA synthetase analog (genX) |
| 0686 | 227 | cytoplasm | DNA-binding response regulator (cpxR) |
| 0688 | 256 | cytoplasm | aminoacyl-histidine dipeptidase (pepD) |
| 0689 | 185 | cytoplasm | integrase/recombinase (xerC) |
| 0698 | 399 | cytoplasm | nifS protein |
| 0699 | 51 | cytoplasm | nuclease |
| 0701 | 153 | cytoplasm | DnaA-related protein |
| 0702 | 279 | inner 7 | uracil permease (uraA) |
| 0703 | 129 | inner 3 | uracil permease (uraA) |
| 0704 | 135 | cytoplasm | uracil phosphoribosyltransferase (upp) |
| 0705 | 341 | cytoplasm | glutaminyl-tRNA synthetase (glnS) |
| 0708 | 78 | cytoplasm | cytoplasmic axial filament protein (cafA) |
| 0709 | 258 | inner 5 | anaerobic C4-dicarboxylate membrane transporter protein |

TABLE III-continued

Annotations
aa = length of polypeptide
PSORT = cellular location of polypeptide, according to PSORT algorithm

| NTH | aa | PSORT | Annotation |
|---|---|---|---|
| 0710 | 43 | inner 1 | anaerobic C4-dicarboxylate membrane transporter protein |
| 0714 | 169 | cytoplasm | protein-export protein (secB) |
| 0718 | 175 | inner 1 | glucose inhibited division protein (gidA) |
| 0719 | 224 | cytoplasm | threonyl-tRNA synthetase (thrS) |
| 0720 | 194 | cytoplasm | acyl carrier protein phosphodiesterase (acpD) |
| 0723 | 146 | cytoplasm | DNA topoisomerase I (topA) |
| 0732 | 200 | cytoplasm | recombination protein RecR (recR) |
| 0733 | 202 | cytoplasm | DNA topoisomerase III (topB) |
| 0734 | 322 | cytoplasm | S-adenosylmethionine synthetase (metX) |
| 0735 | 193 | cytoplasm | anthranilate synthase component II (trpG) or para-aminobenzoate synthase glutamine |
| 0736 | 210 | cytoplasm | para-aminobenzoate synthetase component |
| 0737 | 118 | cytoplasm | folylpolyglutamate synthase/dihydrofolate synthase (folC) |
| 0738 | 184 | periplasmic | acetyl-CoA carboxylase, carboxyl transferase subunit beta |
| 0739 | 93 | cytoplasm | acetyl-CoA carboxylase, carboxyl transferase subunit beta |
| 0740 | 177 | inner 1 | periplasmic serine protease |
| 0741 | 321 | cytoplasm | periplasmic serine protease |
| 0743 | 269 | cytoplasm | tRNA pseudouridylate synthase I (truA) |
| 0745 | 235 | inner 2 | peptide ABC transporter, ATP-binding protein (sapF) |
| 0747 | 37 | cytoplasm | peptide ABC transporter, ATP-binding protein (sapF) |
| 0748 | 44 | cytoplasm | peptide ABC transporter, ATP-binding protein (sapD) |
| 0751 | 86 | cytoplasm | pseudouridine synthase RluD (rluD) |
| 0753 | 198 | cytoplasm | tRNA (guanine-N1)-methyltransferase (trmD) |
| 0754 | 116 | cytoplasm | ribosomal protein L19 (rpL19) |
| 0758 | 235 | cytoplasm | ribosomal protein S3 (rpS3) |
| 0759 | 110 | cytoplasm | ribosomal protein L22 (rpL22) |
| 0760 | 91 | cytoplasm | ribosomal protein S19 (rpS19) |
| 0761 | 180 | cytoplasm | ribosomal protein L2 (rpL2) |
| 0762 | 221 | inner 5 | protein-export membrane protein (secD) |
| 0764 | 406 | inner 1 | protein-export membrane protein (secD) |
| 0765 | 97 | inner 1 | preprotein translocase, YajC subunit (yajC) |
| 0769 | 37 | cytoplasm | queuine tRNA-ribosyltransferase (tgt) |
| 0770 | 371 | cytoplasm | tRNA |
| 0772 | 55 | cytoplasm | thiamine biosynthesis lipoprotein ApbE lipoprotein |
| 0773 | 35 | cytoplasm | lipoprotein |
| 0774 | 299 | inner 1 | thiamine biosynthesis lipoprotein ApbE lipoprotein |
| 0777 | 63 | cytoplasm | ribosomal protein L29 (rpL29) |
| 0778 | 74 | cytoplasm | ribosomal protein L16 (rpL16) |
| 0779 | 335 | cytoplasm | dihydrolipoamide acetyltransferase (aceF) or pyruvate dehydrogenase, E2 component, |
| 0781 | 35 | cytoplasm | dihydrolipoamide acetyltransferase (aceF) |
| 0782 | 549 | cytoplasm | pyruvate dehydrogenase, E1 component (aceE) |
| 0787 | 297 | cytoplasm | glycine cleavage system transcriptional activator (gcvA) or transcriptional regulator, LysR family |
| 0788 | 159 | outer-hand | penicillin-binding protein 1A (ponA) |
| 0790 | 164 | cytoplasm | competence protein A (comA) |
| 0794 | 168 | inner 1 | competence protein B (comB) |
| 0795 | 134 | inner 1 | competence protein C (comC) |
| 0796 | 172 | inner 1 | competence protein D (comD) |
| 0798 | 166 | inner 1 | competence protein E (comE) |
| 0801 | 583 | cytoplasm | arginyl-tRNA synthetase (argS) |
| 0802 | 100 | inner 1 | glutaredoxin (grx) |
| 0803 | 406 | inner 0 | beta-ketoacyl-ACP synthase I (fabB) |
| 0804 | 137 | inner 1 | monofunctional biosynthetic peptidoglycan transglycosylase |
| 0805 | 101 | cytoplasm | trp operon repressor (trpR) |
| 0806 | 305 | cytoplasm | soluble lytic murein transglycosylase |
| 0807 | 267 | cytoplasm | 2-hydroxyacid (glycerate) dehydrogenase |
| 0808 | 30 | cytoplasm | 2-dehydro-3-deoxyphosphooctonate aldolase (kdsA) |
| 0810 | 249 | cytoplasm | 2-dehydro-3-deoxyphosphooctonate aldolase (kdsA) |
| 0812 | 84 | cytoplasm | hemK protein (hemK) |
| 0813 | 202 | inner 1 | hemK protein (hemK) |
| 0817 | 411 | cytoplasm | hydrolase |
| 0821 | 240 | inner 1 | transcriptional regulatory protein (ygiX) |
| 0822 | 154 | inner 1 | sensor protein (ygiY) |
| 0823 | 66 | cytoplasm | sensor protein (ygiY) |
| 0824 | 316 | cytoplasm | glutamyl-tRNA synthetase (gltX) |
| 0825 | 80 | cytoplasm | glutamyl-tRNA synthetase (gltX) |
| 0826 | 79 | cytoplasm | glutamyl-tRNA synthetase (gltX) |
| 0828 | 45 | cytoplasm | ribonuclease PH (rph) |
| 0829 | 278 | inner 1 | amidophosphoribosyltransferase (purF) |
| 0830 | 484 | cytoplasm | DNA gyrase, subunit A (gyrA) |
| 0831 | 54 | cytoplasm | DNA gyrase, subunit A (gyrA) |
| 0833 | 583 | cytoplasm | hemin receptor (hemR) or iron-regulated outer membrane protein FrpB frpB |
| 0834 | 143 | inner 2 | colicin transport protein (tolQ) or biopolymer transport protein ExbB exbB |

TABLE III-continued

Annotations
aa = length of polypeptide
PSORT = cellular location of polypeptide, according to PSORT algorithm

| NTH | aa | PSORT | Annotation |
|---|---|---|---|
| 0835 | 139 | periplasmic | colicin transport protein (tolR) or biopolymer transport protein ExbD exbD |
| 0836 | 337 | inner 1 | outer membrane integrity protein (tolA) or IgA-specific serine endopeptidase iga |
| 0840 | 76 | cytoplasm | ABC transporter, ATP-binding protein |
| 0842 | 31 | cytoplasm | type I restriction enzyme (hsdR) |
| 0844 | 53 | cytoplasm | modification methylase |
| 0845 | 184 | cytoplasm | ADP-heptose synthase (rfaE) or aut protein aut |
| 0847 | 389 | cytoplasm | argininosuccinate lyase (argH) |
| 0848 | 295 | periplasmic | glucosephosphate uridylyltransferase (galU) or UTP--glucose-1-phosphate uridylyltransferase galU |
| 0849 | 63 | periplasmic | carbon storage regulator (csrA) |
| 0850 | 461 | inner 4 | ATP-binding protein protein (cydD) |
| 0851 | 94 | inner 2 | ATP-binding protein protein (cydD) |
| 0852 | 160 | inner 1 | NAD(P)H oxidoreductase |
| 0856 | 133 | periplasmic | protease IV (sppA) |
| 0857 | 152 | cytoplasm | molybdenum ABC transporter, periplasmic-binding protein |
| 0858 | 242 | inner 5 | molybdenum ABC transporter, permease protein (modB) or sulfate ABC transporter, permease protein cysT |
| 0859 | 40 | cytoplasm | molybdenum ABC transporter, ATP-binding protein (modC) |
| 0860 | 245 | cytoplasm | molybdenum ABC transporter, ATP-binding protein (modC) or sulfate ABC transporter, ATP-binding protein cysA |
| 0868 | 119 | cytoplasm | type I restriction/modification specificity protein (hsdS) |
| 0869 | 90 | cytoplasm | anthranilate synthase component I trpE |
| 0873 | 145 | cytoplasm | phosphoserine aminotransferase (serC) |
| 0874 | 234 | inner 2 | succinyl-CoA synthetase, beta subunit (sucC) |
| 0875 | 293 | inner 1 | succinyl-CoA synthetase, alpha subunit (sucD) |
| 0882 | 93 | cytoplasm | mazG protein (mazG) |
| 0887 | 285 | inner 1 | 3-oxoacyl-(acyl-carrier-protein) reductase fabG-2 |
| 0890 | 153 | cytoplasm | DNA polymerase III, delta' subunit (holB) |
| 0892 | 41 | cytoplasm | thiol:disulfide interchange protein (dsbD) |
| 0893 | 60 | cytoplasm | thiol:disulfide interchange protein (dsbD) |
| 0897 | 234 | cytoplasm | phosphoribosylaminoimidazolecarboxamide formyltransferase |
| 0898 | 552 | cytoplasm | ATP-dependent RNA helicase DeaD (deaD) |
| 0900 | 64 | cytoplasm | type I restriction/modification specificity protein (hsdS) |
| 0903 | 248 | cytoplasm | type I restriction enzyme (hsdR) |
| 0905 | 106 | cytoplasm | 2-isopropylmalate synthase (leuA) |
| 0907 | 373 | cytoplasm | DNA processing chain A (dprA) |
| 0910 | 106 | periplasmic | nitrite reductase, Fe—S protein (nrfC) |
| 0912 | 98 | cytoplasm | nitrite reductase, cytochrome C-type protein (nrfB) |
| 0913 | 277 | inner 1 | cell division protein FtsK-related protein |
| 0914 | 205 | outer | outer membrane lipoproteins carrier protein (lolA) |
| 0918 | 286 | cytoplasm | glycogen phosphorylase (glgP) |
| 0919 | 323 | cytoplasm | glycogen phosphorylase (glgP) |
| 0920 | 117 | cytoplasm | glycogen phosphorylase (glgP) |
| 0923 | 253 | cytoplasm | glycogen synthase (glgA) |
| 0925 | 105 | cytoplasm | phosphoglycerate mutase (gpmA) |
| 0934 | 242 | cytoplasm | 3-ketoacyl-acyl carrier protein reductase (fabG) |
| 0935 | 48 | cytoplasm | malonyl CoA-acyl carrier protein transacylase (fabD) |
| 0936 | 222 | cytoplasm | malonyl CoA-acyl carrier protein transacylase (fabD) |
| 0939 | 111 | cytoplasm | 3-oxoacyl-(acyl-carrier-protein) synthase III fabH |
| 0945 | 125 | cytoplasm | molybdopterin biosynthesis protein (moeB) or thiF protein thiF |
| 0946 | 404 | cytoplasm | molybdopterin biosynthesis protein (moeA) |
| 0947 | 55 | cytoplasm | GTP cyclohydrolase I (folE) |
| 0950 | 353 | inner 2 | protease (sohB) |
| 0954 | 274 | cytoplasm | recombination associated protein RdgC rdgC |
| 0956 | 354 | cytoplasm | adenosylmethionine-8-amino-7-oxononanoate aminotransferase |
| 0958 | 379 | cytoplasm | 8-amino-7-oxononanoate synthase (bioF) |
| 0960 | 80 | cytoplasm | ABC transporter, ATP-binding protein |
| 0962 | 66 | cytoplasm | ABC transporter, ATP-binding protein |
| 0963 | 317 | cytoplasm | ABC transporter, ATP-binding protein (msbA) |
| 0965 | 313 | cytoplasm | tetraacyldisaccharide 4'-kinase lpxK |
| 0966 | 254 | cytoplasm | 3-deoxy-D-manno-octulosonate cytidylyltransferase (kdsB) |
| 0967 | 77 | cytoplasm | excinuclease ABC, subunit C (uvrC) |
| 0969 | 204 | cytoplasm | ABC transporter, ATP-binding protein |
| 0974 | 90 | cytoplasm | dethiobiotin synthase (bioD-2) |
| 0976 | 223 | cytoplasm | biotin synthesis protein BioC |
| 0977 | 549 | cytoplasm | long chain fatty acid coA ligase |
| 0983 | 574 | cytoplasm | phosphoenolpyruvate carboxylase (ppc) |
| 0984 | 303 | cytoplasm | gcpE protein (gcpE) |
| 0988 | 226 | cytoplasm | rbs repressor (rbsR) |
| 0989 | 322 | inner 1 | ribokinase (rbsK) or ADP-heptose synthase |
| 0990 | 156 | cytoplasm | D-ribose ABC transporter, periplasmic-binding protein (rbsB) |
| 0992 | 223 | cytoplasm | baseplate assembly protein V |
| 0994 | 52 | inner 0 | adhesin/invasin |

TABLE III-continued

Annotations
aa = length of polypeptide
PSORT = cellular location of polypeptide, according to PSORT algorithm

| NTH | aa | PSORT | Annotation |
|---|---|---|---|
| 0997 | 454 | lipo | multidrug efflux pump channel protein mtrE |
| 1001 | 273 | cytoplasm | transcription termination factor (rho) |
| 1002 | 230 | inner 5 | type 4 prepilin-like protein specific leader peptidase |
| 1003 | 143 | inner 1 | pilus assembly protein PilG pilG |
| 1007 | 39 | cytoplasm | glycerol-3-phosphate regulon repressor (glpR) |
| 1008 | 306 | cytoplasm | fructose-1,6-bisphosphatase (fbp) |
| 1012 | 233 | inner 8 | hydroxyacylglutathione hydrolase |
| 1014 | 182 | cytoplasm | tellurite resistance protein (tehB) |
| 1015 | 541 | periplasmic | oligopeptide ABC transporter, periplasmic-binding protein |
| 1018 | 45 | periplasmic | oligopeptide ABC transporter, permease protein (oppB) |
| 1019 | 256 | cytoplasm | methylenetetrahydrofolate |
| 1021 | 428 | inner 0 | L-fucose permease (fucP) or glucose/galactose transporter gluP |
| 1022 | 216 | cytoplasm | L-fuculose phosphate aldolase (fucA) |
| 1023 | 144 | cytoplasm | fucose operon protein (fucU) |
| 1024 | 30 | cytoplasm | fuculokinase (fucK) |
| 1030 | 492 | cytoplasm | anaerobic glycerol-3-phosphate dehydrogenase, subunit A |
| 1031 | 320 | inner 1 | anaerobic glycerol-3-phosphate dehydrogenase, subunit B |
| 1032 | 242 | inner 5 | transporter |
| 1033 | 116 | cytoplasm | arsenate reductase |
| 1041 | 70 | cytoplasm | hypoxanthine phosphoribosyltransferase (hpt) |
| 1043 | 460 | inner 9 | proton glutamate symport protein or sodium/dicarboxylate symporter family protein |
| 1045 | 155 | cytoplasm | anaerobic ribonucleoside-triphosphate reductase activating |
| 1046 | 242 | cytoplasm | transport ATP-binding protein (cydC) ABC transporter |
| 1048 | 212 | inner 4 | transport ATP-binding protein (cydC) |
| 1050 | 359 | cytoplasm | fructose-bisphosphate aldolase (fba) |
| 1051 | 346 | cytoplasm | ADP-heptose--LPS heptosyltransferase II rfaF |
| 1053 | 56 | cytoplasm | peptidyl-prolyl cis-trans isomerse |
| 1054 | 201 | outer | peptidyl-prolyl cis-trans isomerse |
| 1057 | 452 | cytoplasm | thiophene and furan oxidation protein (thdF) |
| 1058 | 224 | inner 2 | inner membrane protein, 60 kDa (yidC) |
| 1059 | 58 | cytoplasm | ribosomal protein S18 (rpS18) |
| 1060 | 149 | cytoplasm | ribosomal protein L9 (rpL9) |
| 1061 | 577 | cytoplasm | heat shock protein (groEL) |
| 1062 | 102 | cytoplasm | chaperonin (groES) |
| 1063 | 190 | inner 4 | urease, gamma subunit (ureA) |
| 1064 | 216 | inner 5 | rod shape-determining protein (rodA) or cell division protein FtsW ftsW |
| 1066 | 66 | cytoplasm | penicillin-binding protein 2 (pbp2) |
| 1068 | 66 | cytoplasm | cell division protein FtsK-related protein |
| 1071 | 447 | cytoplasm | protease IV (sppA) |
| 1074 | 286 | cytoplasm | lic-1 operon protein (licD) |
| 1075 | 213 | outer | aminopeptidase A/I (pepA) |
| 1077 | 141 | cytoplasm | nucleoside diphosphate kinase (ndk) |
| 1078 | 227 | cytoplasm | GTP-binding protein (yhbZ) |
| 1080 | 317 | inner 1 | phosphoribosylamine--glycine ligase (purD) |
| 1081 | 198 | cytoplasm | phosphoribosylaminoimidazolecarboxamide formyltransferase |
| 1082 | 31 | outer | phosphoribosylaminoimidazolecarboxamide formyltransferase |
| 1083 | 45 | inner 0 | phosphoribosylaminoimidazolecarboxamide formyltransferase |
| 1084 | 199 | inner 0 | sufI protein (sufI) |
| 1085 | 125 | inner 1 | 1-acyl-glycerol-3-phosphate acyltransferase (plsC) |
| 1087 | 75 | inner 1 | 1-acyl-glycerol-3-phosphate acyltransferase (plsC) |
| 1091 | 199 | inner 4 | sodium- and chloride-dependent transporter |
| 1092 | 217 | inner 2 | potassium/copper-transporting ATPase |
| 1093 | 68 | cytoplasm | mercuric ion scavenger protein (merP) |
| 1094 | 68 | cytoplasm | mercuric ion scavenger protein (merP) |
| 1095 | 68 | cytoplasm | mercuric ion scavenger protein (merP) |
| 1096 | 144 | cytoplasm | transcriptional regulator, merR family |
| 1097 | 105 | cytoplasm | met repressor (metJ) |
| 1098 | 109 | inner 1 | transcription termination factor (rho) |
| 1100 | 317 | cytoplasm | fumarate reductase, flavoprotein subunit (frdA) or succinate dehydrogenase, flavoprotein subunit sdhA |
| 1101 | 276 | cytoplasm | fumarate reductase, iron-sulfur protein (frdB) or succinate dehydrogenase, iron-sulfur protein sdhB |
| 1102 | 132 | inner 3 | fumarate reductase, 15 kDa hydrophobic protein (frdC) |
| 1103 | 114 | inner 1 | fumarate reductase, 13 kDa hydrophobic protein (frdD) |
| 1109 | 170 | cytoplasm | terminase, small subunit |
| 1116 | 51 | cytoplasm | heme-hemopexin utilization protein A (hxuA) |
| 1117 | 165 | cytoplasm | heme-hemopexin utilization protein A (hxuA) |
| 1120 | 118 | cytoplasm | dihydroneopterin aldolase (folB) |
| 1124 | 338 | inner 1 | nitrate/nitrite sensor protein (narQ) |
| 1125 | 225 | inner 1 | topoisomerase IV, subunit A (parC) |
| 1127 | 139 | cytoplasm | glucose kinase |
| 1132 | 202 | cytoplasm | type I modification enzyme (hsdM) |
| 1135 | 260 | cytoplasm | type I modification enzyme (hsdM) |

TABLE III-continued

Annotations
aa = length of polypeptide
PSORT = cellular location of polypeptide, according to PSORT algorithm

| NTH | aa | PSORT | Annotation |
|---|---|---|---|
| 1137 | 362 | cytoplasm | type I restriction/modification specificity protein (hsdS) |
| 1138 | 226 | inner 0 | thiamin-phosphate pyrophosphorylase |
| 1139 | 254 | cytoplasm | phosphomethylpyrimidine kinase (thiD) |
| 1140 | 32 | cytoplasm | phosphomethylpyrimidine kinase (thiD) |
| 1141 | 263 | inner 1 | hydroxyethylthiazole kinase |
| 1143 | 70 | cytoplasm | outer membrane protein NsgA |
| 1144 | 51 | cytoplasm | ribonuclease E (rne) |
| 1145 | 75 | cytoplasm | ribonuclease E (rne) |
| 1148 | 42 | cytoplasm | ribonuclease E (rne) |
| 1151 | 180 | inner 1 | adenine phosphoribosyltransferase (apt) |
| 1152 | 311 | cytoplasm | DNA polymerase III, subunits gamma and tau (dnaX) |
| 1154 | 221 | cytoplasm | DNA polymerase III, subunits gamma and tau (dnaX) |
| 1155 | 173 | cytoplasm | DNA polymerase III, subunits gamma and tau (dnaX) |
| 1156 | 60 | cytoplasm | uracil phosphoribosyltransferase (upp) |
| 1165 | 406 | cytoplasm | nifS protein (nifS) |
| 1166 | 151 | cytoplasm | iscU protein (iscU) |
| 1167 | 107 | cytoplasm | HesB/YadR/YfhF family protein |
| 1168 | 174 | cytoplasm | co-chaperone Hsc20 (hscB) |
| 1171 | 151 | cytoplasm | heat shock protein (hscA) |
| 1172 | 53 | cytoplasm | D-lactate dehydrogenase (dld) |
| 1173 | 36 | cytoplasm | type I restriction enzyme EcoR124II R protein, |
| 1174 | 183 | lipo | lipoprotein (spr) |
| 1175 | 194 | cytoplasm | tldD protein tldD |
| 1177 | 44 | cytoplasm | hemoglobin-binding protein |
| 1180 | 234 | cytoplasm | peptidase E (pepE) |
| 1182 | 386 | cytoplasm | ribosomal protein S1 (rpS1) |
| 1183 | 94 | cytoplasm | integration host factor, beta-subunit (himD) |
| 1186 | 194 | cytoplasm | orotidine 5′-phosphate decarboxylase (pyrF) |
| 1188 | 181 | inner 1 | lipopolysaccharide biosynthesis protein |
| 1189 | 264 | inner 1 | alpha-1,2-N-acetylglucosamine transferase rfaK |
| 1190 | 57 | periplasmic | lipopolysaccharide biosynthesis protein |
| 1191 | 304 | inner 2 | alpha-2,3-sialyltransferase |
| 1192 | 160 | inner 4 | lipopolysaccharide biosynthesis protein |
| 1197 | 124 | cytoplasm | uridine kinase (udk) |
| 1198 | 195 | cytoplasm | deoxycytidine triphosphate deaminase (dcd) |
| 1201 | 402 | inner 10 | drug resistance translocase family protein |
| 1202 | 158 | cytoplasm | GTP-binding protein |
| 1203 | 55 | outer | hemoglobin-binding protein |
| 1206 | 736 | cytoplasm | TonB-dependent receptor or hemoglobin receptor hmbR |
| 1207 | 91 | cytoplasm | transcriptional regulator, HTH_3 family |
| 1212 | 230 | cytoplasm | glycyl-tRNA synthetase, beta chain (glyS) |
| 1218 | 244 | cytoplasm | glycyl-tRNA synthetase, alpha chain (glyQ) |
| 1228 | 198 | cytoplasm | seryl-tRNA synthetase (serS) |
| 1229 | 282 | inner 2 | cytochrome C-type biogenesis protein (nrfF) |
| 1230 | 176 | inner 1 | thiol:disulfide interchange protein (dsbE) |
| 1231 | 507 | inner 9 | cytochrome C-type biogenesis |
| 1233 | 380 | inner 1 | glutamate dehydrogenase (gdhA) |
| 1242 | 135 | cytoplasm | transcriptional regulator |
| 1253 | 266 | cytoplasm | transcriptional regulatory protein |
| 1254 | 101 | inner 3 | galactoside ABC transporter, permease protein (mglC) |
| 1256 | 185 | inner 6 | intracellular septation protein A ispA |
| 1258 | 154 | cytoplasm | acyl CoA thioester hydrolase family protein |
| 1261 | 158 | periplasmic | soluble lytic murein transglycosylase |
| 1263 | 229 | cytoplasm | pyridoxamine phosphate oxidase (pdxH) |
| 1264 | 162 | cytoplasm | GTP-binding protein |
| 1266 | 69 | cytoplasm | NAD(P)H-flavin oxidoreductase |
| 1267 | 386 | cytoplasm | ATP-binding protein (mrp) |
| 1268 | 460 | periplasmic | methionyl-tRNA synthetase (metG) |
| 1269 | 70 | cytoplasm | phosphoribosylaminoimidazole carboxylase, catalytic |
| 1272 | 596 | cytoplasm | aminopeptidase N (pepN) |
| 1273 | 175 | inner 1 | dihydrodipicolinate reductase (dapB) |
| 1274 | 82 | cytoplasm | ferredoxin |
| 1276 | 329 | cytoplasm | phenylalanyl-tRNA synthetase, alpha subunit (pheS) |
| 1277 | 373 | cytoplasm | phenylalanyl-tRNA synthetase, beta subunit (pheT) |
| 1278 | 286 | cytoplasm | DNA adenine methylase (dam) |
| 1279 | 298 | inner 1 | 3-dehydroquinate synthase (aroB) |
| 1280 | 74 | inner 2 | NADH:ubiquinone oxidoreductase, Na translocating |
| 1281 | 208 | inner 6 | NADH:ubiquinone oxidoreductase, Na translocating |
| 1282 | 269 | inner 1 | NADH:ubiquinone oxidoreductase, Na translocating |
| 1283 | 411 | inner 7 | NADH:ubiquinone oxidoreductase, subunit B (nqrB) |
| 1284 | 48 | cytoplasm | NADH:ubiquinone oxidoreducatase subunit A, Na translocating |
| 1285 | 254 | cytoplasm | NADH:ubiquinone oxidoreducatase subunit A, Na translocating |
| 1286 | 85 | inner 1 | nitrogen fixation protein (rnfG) |
| 1287 | 358 | inner 9 | Na(+)-translocating NADH-quinone reductase, subunit |

TABLE III-continued

Annotations
aa = length of polypeptide
PSORT = cellular location of polypeptide, according to PSORT algorithm

| NTH | aa | PSORT | Annotation |
|---|---|---|---|
| 1290 | 679 | outer | ferredoxin, 4Fe—4S bacterial type |
| 1291 | 58 | cytoplasm | ferredoxin, 4Fe—4S bacterial type |
| 1295 | 406 | inner 1 | polyribonucleotide nucleotidyltransferase pnp |
| 1297 | 296 | inner 1 | polyribonucleotide nucleotidyltransferase pnp |
| 1302 | 452 | inner 1 | O-succinylbenzoate--CoA ligase (menE) or long-chain-fatty-acid--CoA ligase fadD-2 |
| 1303 | 201 | cytoplasm | seqA protein (seqA) |
| 1304 | 85 | cytoplasm | esterase/lipase |
| 1305 | 65 | inner 1 | esterase/lipase |
| 1306 | 144 | inner 0 | esterase/lipase |
| 1307 | 41 | inner 1 | iron (chelated) ABC transporter, permease protein (yfeD) |
| 1308 | 147 | inner 2 | iron (chelated) ABC transporter, permease protein (yfeD) |
| 1309 | 282 | inner 8 | iron (chelated) ABC transporter, permease protein (yfeC) |
| 1310 | 306 | cytoplasm | iron (chelated) transporter, ATP-binding protein (yfeB) |
| 1311 | 293 | periplasmic | iron (chelated) ABC transporter, periplasmic-binding protein |
| 1313 | 154 | lipo | outer membrane integrity protein (tolA) or IgA-specific serine endopeptidase iga |
| 1314 | 253 | cytoplasm | penicillin-binding protein 7 |
| 1318 | 41 | cytoplasm | transcriptional activator (ilvY) |
| 1319 | 292 | inner 9 | rarD protein |
| 1320 | 105 | cytoplasm | glpE protein (glpE) |
| 1321 | 263 | inner 1 | triosephosphate isomerase (tpiA) |
| 1323 | 107 | cytoplasm | integrase/recombinase (xerC) |
| 1324 | 100 | cytoplasm | dnaK suppressor protein (dksA) |
| 1326 | 58 | cytoplasm | poly(A) polymerase (pcnB) |
| 1327 | 450 | inner 10 | C4-dicarboxylate transporter |
| 1331 | 131 | cytoplasm | uracil DNA glycosylase (ung) |
| 1332 | 124 | inner 2 | bicyclomycin resistance protein (bcr) |
| 1338 | 50 | cytoplasm | gamma-glutamyl phosphate reductase (proA) |
| 1339 | 47 | cytoplasm | gamma-glutamyl phosphate reductase (proA) |
| 1340 | 39 | cytoplasm | gamma-glutamyl phosphate reductase (proA) |
| 1341 | 319 | inner 1 | gamma-glutamyl phosphate reductase (proA) |
| 1343 | 98 | cytoplasm | heat shock protein (dnaJ) |
| 1344 | 133 | cytoplasm | acetyl-CoA carboxylase, biotin carboxyl carrier protein |
| 1345 | 443 | cytoplasm | acetyl-CoA carboxylase, biotin carboxylase (accC) |
| 1348 | 320 | inner 7 | sodium/pantothenate symporter (panF) |
| 1349 | 493 | cytoplasm | cell division protein (ftsH) |
| 1351 | 201 | cytoplasm | dihydropteroate synthase (folP-2) |
| 1352 | 445 | cytoplasm | mrsA protein (mrsA) or phosphoglucomutase/phosphomannomutase family |
| 1355 | 438 | cytoplasm | DNA-directed RNA polymerase, beta' chain (rpoC) |
| 1357 | 172 | inner 2 | rod shape-determining protein (rodA) |
| 1359 | 621 | inner 1 | penicillin-binding protein 2 (pbp2) |
| 1361 | 193 | cytoplasm | modification methylase NlaIV |
| 1363 | 432 | inner 1 | 3-phosphoshikimate-1-carboxyvinyltransferase (aroA) or 3- |
| 1365 | 298 | inner 1 | formyltetrahydrofolate deformylase (purU) or phosphoribosylglycinamide formyltransferase purN |
| 1366 | 138 | cytoplasm | DNA-binding protein H-NS (hns) |
| 1369 | 66 | cytoplasm | DNA polymerase III, alpha subunit (dnaE) |
| 1370 | 35 | cytoplasm | DNA polymerase III, alpha subunit (dnaE) |
| 1371 | 847 | cytoplasm | DNA polymerase III, alpha subunit (dnaE) |
| 1373 | 118 | cytoplasm | threonine deaminase (ilvA) |
| 1378 | 196 | cytoplasm | MutT/nudix family protein |
| 1379 | 382 | inner 1 | glutamate 5-kinase (gamma-glutamyl kinase) (proB) |
| 1380 | 128 | inner 0 | dihydrofolate reductase (folA) |
| 1381 | 46 | cytoplasm | dihydrofolate reductase (folA) |
| 1383 | 392 | inner 2 | multidrug resistance protein A (emrA) or fatty acid efflux system protein farA |
| 1384 | 343 | cytoplasm | poly(A) polymerase (pcnB) |
| 1386 | 106 | cytoplasm | 2-amino-4-hydroxy-6-hydroxymethyldihydropteridine- |
| 1388 | 432 | periplasmic | N-acetylmuramoyl-L-alanine amidase |
| 1389 | 227 | cytoplasm | DNA mismatch repair protein (mutL) |
| 1392 | 247 | cytoplasm | hemY protein (hemY) |
| 1393 | 175 | inner 1 | hemY protein (hemY) |
| 1394 | 377 | periplasmic | uroporphyrin-III C-methyltransferase (hemX) |
| 1398 | 194 | inner 0 | transcriptional activator (ilvY) |
| 1400 | 492 | inner 1 | ketol-acid reductoisomerase (ilvC) |
| 1401 | 426 | cytoplasm | anaerobic glycerol-3-phosphate dehydrogenase, subunit C |
| 1402 | 30 | cytoplasm | tRNA (guanine-N1)-methyltransferase (trmD) |
| 1403 | 59 | cytoplasm | 16S rRNA processing protein RimM rimM |
| 1404 | 81 | cytoplasm | 16S rRNA processing protein RimM rimM |
| 1405 | 82 | cytoplasm | ribosomal protein S16 (rpS16) |
| 1407 | 603 | periplasmic | 5'-nucleotidase |
| 1408 | 128 | cytoplasm | shikimic acid kinase I (aroK) |
| 1410 | 249 | cytoplasm | stationary-phase survival protein (surE) |

TABLE III-continued

Annotations
aa = length of polypeptide
PSORT = cellular location of polypeptide, according to PSORT algorithm

| NTH | aa | PSORT | Annotation |
|---|---|---|---|
| 1411 | 128 | inner 2 | lipoprotein B (lppB) |
| 1412 | 74 | inner 1 | lipoprotein B (lppB) |
| 1416 | 354 | lipo | lipoprotein NlpD |
| 1417 | 56 | cytoplasm | lipoprotein NlpD |
| 1420 | 62 | inner 1 | phosphate ABC transporter, permease protein (pstC) |
| 1421 | 282 | inner 5 | phosphate ABC transporter, permease protein (pstA) or sulfate ABC transporter, permease protein cysT |
| 1422 | 255 | cytoplasm | amino acid ABC transporter, ATP-binding protein or sulfate ABC transporter, ATP-binding protein cysA |
| 1423 | 154 | cytoplasm | phosphate regulon transcriptional regulatory protein (phoB) or DNA-binding response regulator NULL |
| 1424 | 72 | cytoplasm | phosphate regulon transcriptional regulatory protein (phoB) |
| 1425 | 425 | inner 1 | phosphate regulon sensor protein (phoR) or sensor histidine kinase NULL |
| 1426 | 44 | cytoplasm | exodeoxyribonuclease I (sbcB) |
| 1427 | 474 | inner 1 | exodeoxyribonuclease I (sbcB) |
| 1428 | 158 | inner 1 | aminopeptidase A/I (pepA) |
| 1429 | 480 | inner 5 | high-affinity choline transport protein (betT) |
| 1430 | 132 | inner 2 | high-affinity choline transport protein (betT) |
| 1431 | 57 | inner 0 | sensor protein (ygiY) |
| 1432 | 139 | cytoplasm | high affinity ribose transport protein (rbsD) |
| 1433 | 493 | cytoplasm | D-ribose ABC transporter, ATP-binding protein (rbsA) |
| 1434 | 323 | inner 9 | D-ribose ABC transporter, permease protein (rbsC) |
| 1435 | 53 | periplasmic | D-ribose ABC transporter, periplasmic-binding protein |
| 1436 | 88 | cytoplasm | D-ribose ABC transporter, periplasmic-binding protein (rbsB) |
| 1438 | 246 | inner 6 | heme exporter protein C (ccmC) or cytochrome c-type biogenesis protein |
| 1439 | 221 | inner 6 | heme exporter protein B (ccmB) |
| 1440 | 212 | cytoplasm | heme exporter ATP-binding protein A (ccmA) or amino acid ABC transporter, ATP-binding protein |
| 1442 | 215 | cytoplasm | superoxide dismutase (sodA) |
| 1443 | 231 | cytoplasm | ABC transporter, ATP-binding protein |
| 1445 | 105 | cytoplasm | anti-sigma factor B antagonist |
| 1446 | 99 | cytoplasm | BolA/YrbA family protein |
| 1447 | 424 | inner 3 | UDP-N-acetylglucosamine 1-carboxyvinyltransferase (murZ) |
| 1448 | 110 | inner 1 | amino acid ABC transporter, periplasmic-binding protein |
| 1449 | 135 | cytoplasm | amino acid ABC transporter, periplasmic-binding protein |
| 1450 | 234 | inner 3 | amino acid ABC transporter, permease protein |
| 1456 | 51 | cytoplasm | ATP-dependent Clp protease, ATPase subunit (clpB) |
| 1457 | 246 | cytoplasm | RNA methyltransferase, TrmH family |
| 1459 | 782 | cytoplasm | virulence-associated protein (vacB) or ribonuclease II family protein vacB |
| 1460 | 83 | cytoplasm | peptidyl-prolyl cis-trans isomerase, FkbP-type (slyD) or FKBP-type peptidyl-prolyl cis-trans isomerase |
| 1462 | 128 | cytoplasm | ribosome binding factor A (rbfA) |
| 1463 | 306 | cytoplasm | tRNA pseudouridine 55 synthase (truB) |
| 1464 | 379 | inner 1 | chorismate mutase/prephenate dehydrogenase (tyrA) |
| 1467 | 38 | inner 1 | chorismate synthase (aroC) |
| 1468 | 286 | periplasmic | penicillin-insensitive murein endopeptidase (mepA) |
| 1472 | 318 | inner 2 | lipid A biosynthesis (kdo)2-(lauroyl)-lipid IVA or HtrB/MsbB family protein |
| 1473 | 126 | inner 1 | oligopeptide transporter, periplasmic-binding protein, |
| 1475 | 696 | cytoplasm | oligopeptidase A (prlC) |
| 1476 | 292 | cytoplasm | type I modification enzyme (hsdM) |
| 1477 | 196 | cytoplasm | type I modification enzyme (hsdM) |
| 1480 | 204 | cytoplasm | riboflavin synthase, alpha chain (ribE) |
| 1482 | 212 | cytoplasm | aminopeptidase N (pepN) |
| 1483 | 140 | cytoplasm | glutaminyl-tRNA synthetase (glnS) |
| 1485 | 699 | cytoplasm | 4-alpha-glucanotransferase (malQ) |
| 1499 | 273 | cytoplasm | glutamine synthetase (glnA) |
| 1500 | 96 | inner 1 | glutamine synthetase (glnA) |
| 1501 | 50 | cytoplasm | glutamine synthetase (glnA) |
| 1503 | 347 | inner 0 | DTDP-glucose 4,6-dehydratase (rffG) |
| 1505 | 527 | cytoplasm | topoisomerase IV, subunit B (parE) |
| 1506 | 315 | inner 1 | lipid A biosynthesis lauroyl acyltransferase (htrB) |
| 1507 | 308 | cytoplasm | ADP-heptose synthase (rfaE) |
| 1508 | 83 | cytoplasm | DNA-directed RNA polymerase, beta' chain (rpoC) |
| 1509 | 829 | cytoplasm | DNA-directed RNA polymerase, beta' chain (rpoC) |
| 1510 | 332 | inner 8 | tellurite resistance protein (tehA) |
| 1511 | 81 | cytoplasm | ribosomal protein L13 (rpL13) |
| 1512 | 153 | cytoplasm | ribosomal protein S9 (rpS9) |
| 1513 | 101 | cytoplasm | urease, beta subunit (ureB) |
| 1514 | 572 | cytoplasm | urease, alpha subunit (ureC) |
| 1515 | 185 | inner 1 | urease accessory protein (ureE) |
| 1519 | 183 | cytoplasm | urease accessory protein (ureF) |
| 1520 | 107 | cytoplasm | urease accessory protein (ureG) |
| 1523 | 334 | cytoplasm | ornithine carbamoyltransferase (arcB) |
| 1524 | 310 | cytoplasm | carbamate kinase (arcC) |

TABLE III-continued

Annotations
aa = length of polypeptide
PSORT = cellular location of polypeptide, according to PSORT algorithm

| NTH | aa | PSORT | Annotation |
|---|---|---|---|
| 1526 | 193 | inner 3 | efflux pump component MtrF mtrF |
| 1527 | 113 | inner 2 | anaerobic C4-dicarboxylate membrane transporter protein |
| 1528 | 136 | inner 1 | NADH dehydrogenase (ndh) |
| 1530 | 315 | cytoplasm | NADH dehydrogenase (ndh) |
| 1531 | 410 | inner 1 | glycerol-3-phosphate acyltransferase (plsB) |
| 1532 | 367 | inner 0 | glycerol-3-phosphate acyltransferase (plsB) |
| 1533 | 75 | cytoplasm | lexA repressor (lexA) |
| 1534 | 121 | cytoplasm | opacity protein or outer membrane protein NsgA nsgA |
| 1537 | 227 | inner 4 | arginine ABC transporter, permease protein (artM) |
| 1538 | 221 | inner 4 | arginine ABC transporter, permease protein (artQ) |
| 1539 | 72 | cytoplasm | arginine ABC transporter, periplasmic-binding protein (artI) |
| 1541 | 99 | periplasmic | arginine ABC transporter, periplasmic-binding protein |
| 1542 | 243 | cytoplasm | arginine ABC transporter, ATP-binding protein (artP) |
| 1544 | 69 | cytoplasm | phosphoheptose isomerase (gmhA) |
| 1545 | 73 | cytoplasm | shikimate 5-dehydrogenase-related protein |
| 1546 | 267 | cytoplasm | serine acetyltransferase (cysE) |
| 1548 | 332 | inner 1 | glycerol-3-phosphate dehydrogenase (NAD+) (gpsA) |
| 1549 | 567 | cytoplasm | adenylate cyclase (cyaA) |
| 1550 | 42 | cytoplasm | adenylate cyclase (cyaA) |
| 1551 | 228 | cytoplasm | adenylate cyclase (cyaA) |
| 1552 | 110 | lipo | ribosomal-protein-alanine acetyltransferase (rimI) |
| 1554 | 134 | cytoplasm | DNA polymerase III, psi subunit (holD) |
| 1556 | 222 | cytoplasm | hemK protein hemK |
| 1558 | 181 | cytoplasm | GTP-binding protein (era) |
| 1559 | 125 | inner 0 | GTP-binding protein (era) |
| 1561 | 227 | cytoplasm | ribonuclease III (rnc) |
| 1562 | 349 | inner 3 | signal peptidase I (lepB) |
| 1565 | 345 | cytoplasm | tail fibre protein |
| 1568 | 395 | cytoplasm | tyrosyl tRNA synthetase (tyrS) |
| 1569 | 315 | inner 1 | phosphoribosylpyrophosphate synthetase (prsA) |
| 1575 | 72 | inner 1 | IS1016-V6 protein |
| 1576 | 563 | cytoplasm | glucose-6-phosphate isomerase (pgi) |
| 1577 | 360 | cytoplasm | alanine racemase, biosynthetic (alr) |
| 1578 | 126 | cytoplasm | replicative DNA helicase (dnaB) |
| 1579 | 303 | cytoplasm | replicative DNA helicase (dnaB) |
| 1582 | 991 | outer-hand | hemoglobin-binding protein |
| 1583 | 237 | cytoplasm | zinc protease |
| 1584 | 276 | inner 1 | adenylosuccinate synthetase (purA) |
| 1585 | 41 | cytoplasm | adenylosuccinate synthetase (purA) |
| 1586 | 297 | inner 1 | 2,3,4,5-tetrahydropyridine-2-carboxylate |
| 1588 | 336 | inner 1 | purine nucleotide synthesis repressor (purR) |
| 1589 | 78 | cytoplasm | phosphoenolpyruvate carboxylase (ppc) |
| 1590 | 45 | inner 1 | ribosomal protein S1 (rpS1) |
| 1591 | 244 | cytoplasm | cytidylate kinase 2 (cmkB) |
| 1593 | 291 | cytoplasm | singlet oxygen resistance protein |
| 1597 | 549 | inner 1 | D-lactate dehydrogenase (dld) |
| 1609 | 462 | inner 1 | oxidoreductase |
| 1610 | 199 | cytoplasm | spermidine/putrescine ABC transporter, periplasmic-binding |
| 1613 | 41 | cytoplasm | carbonic anhydrase |
| 1614 | 647 | cytoplasm | ABC transporter, ATP-binding protein |
| 1618 | 289 | inner 6 | cytochrome C-type biogenesis protein (ccmF) |
| 1619 | 181 | periplasmic | thiol:disulfide interchange protein (dsbE) |
| 1624 | 152 | cytoplasm | DNA ligase (lig) |
| 1625 | 1027 | inner 1 | type I restriction enzyme (hsdR) |
| 1627 | 123 | cytoplasm | anticodon nuclease prrC |
| 1629 | 177 | inner 1 | oligopeptide ABC transporter, ATP-binding protein (oppD) or sulfate ABC transporter, ATP-binding protein cysA |
| 1630 | 356 | cytoplasm | oligopeptide ABC transporter, ATP-binding protein (oppF) or sulfate ABC transporter, ATP-binding protein cysA |
| 1631 | 292 | inner 1 | membrane protein (lapB) |
| 1635 | 683 | cytoplasm | 5-methyltetrahydropteroyltriglutamate-homocysteine |
| 1636 | 73 | cytoplasm | 5-methyltetrahydropteroyltriglutamate-homocysteine |
| 1639 | 363 | cytoplasm | GTP-binding protein |
| 1640 | 194 | cytoplasm | peptidyl-tRNA hydrolase (pth) |
| 1645 | 163 | cytoplasm | exodeoxyribonuclease VII, large subunit (xseA) |
| 1646 | 183 | cytoplasm | YhbX/YhjW/YijP/YjdB family protein |
| 1648 | 242 | cytoplasm | heat shock protein (dnaJ) |
| 1650 | 320 | cytoplasm | heat shock protein 70 (dnaK) |
| 1651 | 327 | cytoplasm | heat shock protein 70 (dnaK) |
| 1653 | 411 | inner 8 | gluconate permease gntP |
| 1659 | 269 | cytoplasm | molybdenum cofactor biosynthesis protein A (moaA) |
| 1662 | 337 | inner 2 | sugar isomerase, KpsF/GutQ family |
| 1664 | 531 | inner 1 | single-stranded-DNA-specific exonuclease (recJ) |
| 1665 | 39 | cytoplasm | single-stranded-DNA-specific exonuclease (recJ) |

TABLE III-continued

Annotations
aa = length of polypeptide
PSORT = cellular location of polypeptide, according to PSORT algorithm

| NTH | aa | PSORT | Annotation |
|---|---|---|---|
| 1666 | 235 | outer | thiol:disulfide interchange protein (dsbA) |
| 1668 | 230 | inner 1 | pfs protein (pfs) or 5-methylthioadenosine |
| 1670 | 565 | cytoplasm | transferrin-binding protein or TonB-dependent receptor |
| 1671 | 568 | inner 1 | lon protease or ATP-dependent protease La lon |
| 1672 | 139 | cytoplasm | 3-hydroxydecanoyl-(acyl carrier-protein) dehydratase (fabA) |
| 1678 | 155 | cytoplasm | bacterioferritin comigratory protein (bcp) |
| 1679 | 286 | cytoplasm | dihydrodipicolinate synthetase (dapA) |
| 1680 | 209 | lipo | lipoprotein |
| 1681 | 107 | cytoplasm | sigma(54) modulation protein |
| 1682 | 312 | cytoplasm | glycosyl transferase |
| 1688 | 613 | inner 2 | sensor histidine kinase |
| 1690 | 145 | inner 1 | UDP-N-acetylglucosamine acetyltransferase (lpxA) |
| 1692 | 403 | inner 0 | lipid-A-disaccharide synthetase (lpxB) |
| 1693 | 197 | inner 1 | ribonuclease HII (rnhB) |
| 1694 | 146 | cytoplasm | modification methylase |
| 1696 | 185 | cytoplasm | ribosome releasing factor (rrf) |
| 1698 | 226 | inner 1 | 1-deoxy-D-xylulose 5-phosphate reductoisomerase (dxr) |
| 1700 | 171 | cytoplasm | 1-deoxy-D-xylulose 5-phosphate reductoisomerase (dxr) |
| 1704 | 370 | cytoplasm | ribonucleoside-diphosphate reductase, alpha chain (nrdA) |
| 1705 | 39 | cytoplasm | ribonucleoside diphosphate reductase, beta chain (nrdB) |
| 1706 | 311 | cytoplasm | ribonucleoside diphosphate reductase, beta chain (nrdB) |
| 1707 | 409 | inner 1 | 2-oxoglutarate dehydrogenase E2 component, dihydrolipoamide |
| 1708 | 222 | inner 1 | 2-oxoglutarate dehydrogenase E1 component (sucA) |
| 1709 | 184 | cytoplasm | ribosomal protein S4 (rpS4) |
| 1712 | 314 | inner 2 | phosphoserine phosphatase (serB) |
| 1714 | 680 | cytoplasm | transketolase 1 (tktA) |
| 1716 | 333 | cytoplasm | biotin synthetase (bioB) |
| 1717 | 217 | cytoplasm | thiamin ABC transporter, ATP-binding protein or spermidine/putrescine ABC transporter, ATP-binding |
| 1718 | 84 | inner 1 | thiamin ABC transporter, permease protein |
| 1719 | 77 | inner 1 | molybdopeterin biosynthesis protein (mog) |
| 1720 | 112 | cytoplasm | nitrogen regulatory protein P-II (glnB) |
| 1722 | 348 | inner 6 | transporter |
| 1724 | 264 | periplasmic | primosomal protein N' (priA) |
| 1725 | 487 | inner 1 | primosomal protein N' (priA) |
| 1726 | 102 | cytoplasm | PTS system, glucose-specific IIA component (crr) |
| 1729 | 581 | inner 1 | phosphoenolpyruvate-protein phosphotransferase (ptsI) |
| 1730 | 92 | cytoplasm | phosphocarrier protein HPr (ptsH) |
| 1733 | 189 | cytoplasm | oligoribonuclease orn |
| 1735 | 294 | inner 2 | phenylalanyl-tRNA synthetase, beta subunit (pheT) |
| 1736 | 53 | cytoplasm | integration host factor, alpha-subunit (himA) |
| 1738 | 47 | cytoplasm | integration host factor, alpha-subunit (himA) |
| 1739 | 161 | lipo | lipoprotein (nlpC) |
| 1747 | 87 | cytoplasm | pyruvate kinase, type II (pykA) |
| 1758 | 387 | cytoplasm | modification methylase NlaIV |
| 1766 | 90 | cytoplasm | exodeoxyribonuclease, small subunit (xseB) |
| 1767 | 296 | inner 1 | geranyltranstransferase (ispA) |
| 1768 | 316 | cytoplasm | 1-deoxyxylulose-5-phosphate synthase (dxs) |
| 1770 | 99 | inner 1 | glycosyl transferase |
| 1771 | 464 | cytoplasm | fumarate hydratase, class II (fumC) |
| 1776 | 315 | cytoplasm | dihydroorotate dehydrogenase (pyrD) |
| 1780 | 669 | cytoplasm | transferrin-binding protein 2 precursor (tbp2) |
| 1781 | 560 | periplasmic | transferrin-binding protein 1 precursor (tbp1) |
| 1782 | 152 | inner 1 | deoxyuridinetriphosphatase (dut) |
| 1783 | 400 | inner 1 | DNA/pantothenate metabolism flavoprotein (dfp) |
| 1785 | 234 | cytoplasm | DNA repair protein (radC) |
| 1786 | 82 | cytoplasm | ribosomal protein L28 (rpL28) |
| 1787 | 56 | cytoplasm | ribosomal protein L33 (rpL33) |
| 1788 | 454 | inner 1 | L-2,4-diaminobutyrate:2-ketoglutarate 4-aminotransferase or acetylornithine aminotransferase argD |
| 1790 | 132 | cytoplasm | virulence associated protein C (vapC) |
| 1791 | 443 | cytoplasm | L-2,4-diaminobutyrate decarboxylase |
| 1792 | 434 | cytoplasm | ATP-dependent RNA helicase (hrpa) |
| 1793 | 780 | inner 1 | ATP-dependent RNA helicase (hrpa) |
| 1794 | 122 | cytoplasm | ATP-dependent helicase (hrpa) |
| 1799 | 243 | inner 5 | cytochrome D ubiquinol oxidase, subunit II (cydB) |
| 1800 | 198 | cytoplasm | uxu operon regulator (uxuR) |
| 1801 | 51 | cytoplasm | mannonate dehydratase (uxuA) |
| 1802 | 33 | cytoplasm | acyl carrier protein (acpP) |
| 1803 | 220 | inner 5 | anaerobic C4-dicarboxylate membrane transporter protein |
| 1805 | 486 | inner 5 | NAD(P) transhydrogenase, subunit alpha (pntA) |
| 1806 | 474 | inner 7 | NAD(P) transhydrogenase, subunit beta (pntB) |
| 1807 | 305 | periplasmic | transcriptional regulator |
| 1808 | 70 | cytoplasm | DNA topoisomerase I (topA) |

TABLE III-continued

Annotations
aa = length of polypeptide
PSORT = cellular location of polypeptide, according to PSORT algorithm

| NTH | aa | PSORT | Annotation |
|---|---|---|---|
| 1809 | 50 | cytoplasm | signal recognition particle protein (ffh) |
| 1812 | 88 | cytoplasm | type I restriction enzyme (hsdR) |
| 1813 | 646 | inner 1 | type I restriction enzyme (hsdR) |
| 1815 | 418 | inner 1 | type I restriction/modification specificity protein (hsdS) |
| 1819 | 545 | outer | heme-hemopexin utilization protein B (hxuB) |
| 1825 | 402 | cytoplasm | xylose isomerase (xylA) |
| 1826 | 493 | cytoplasm | xylulose kinase |
| 1827 | 308 | cytoplasm | ADP-L-glycero-D-mannoheptose-6-epimerase (rfaD) |
| 1828 | 167 | inner 1 | thioredoxin |
| 1830 | 223 | cytoplasm | deoxyribose-phosphate aldolase (deoC) |
| 1831 | 509 | cytoplasm | competence protein (comM) |
| 1834 | 72 | cytoplasm | glucose kinase |
| 1835 | 288 | inner 1 | RpiR/YebK/YfhH family protein |
| 1836 | 293 | inner 0 | N-acetylneuraminate lyase (nanA) or dihydrodipicolinate synthase dapA |
| 1838 | 270 | inner 1 | glucosamine-6-phosphate isomerase (nagB) |
| 1839 | 381 | cytoplasm | N-acetylglucosamine-6-phosphate deacetylase (nagA) |
| 1840 | 107 | cytoplasm | outer membrane protein P2 (ompP2) |
| 1841 | 38 | cytoplasm | DNA polymerase III, delta' subunit (holB) |
| 1845 | 716 | outer-hand | LavA virulence protein |
| 1846 | 237 | cytoplasm | thymidylate kinase |
| 1848 | 265 | cytoplasm | argininosuccinate synthetase (argG) |
| 1855 | 97 | cytoplasm | exoribonuclease II (rnb) |
| 1858 | 188 | cytoplasm | L-lactate dehydrogenase (lctD) |
| 1859 | 269 | inner 1 | glutamate racemase (murI) |
| 1860 | 693 | cytoplasm | ATP-dependent DNA helicase (recG) |
| 1861 | 515 | inner 1 | guanosine-3',5'-bis(diphosphate) 3'-pyrophosphohydrolase |
| 1867 | 69 | cytoplasm | molybdenum-pterin binding protein (mopI) |
| 1868 | 109 | cytoplasm | desulfoviridin gamma subunit |
| 1870 | 393 | inner 1 | killing protein (kicB) |
| 1871 | 343 | periplasmic | enolase (eno) |
| 1875 | 508 | cytoplasm | catalase (hktE) |
| 1876 | 50 | cytoplasm | glucosamine--fructose-6-phosphate aminotransferase (glmS) |
| 1877 | 232 | cytoplasm | glycogen synthase (glgA) |
| 1879 | 174 | cytoplasm | glucose-1-phosphate adenylyltransferase (glgC) |
| 1880 | 283 | cytoplasm | glucose-1-phosphate adenylyltransferase (glgC) |
| 1881 | 435 | inner 1 | glycogen operon protein (glgX) |
| 1882 | 229 | inner 1 | glycogen operon protein (glgX) |
| 1883 | 685 | cytoplasm | 1,4-alpha-glucan branching enzyme (glgB) |
| 1884 | 119 | cytoplasm | ribosomal protein S10 (rpS10) |
| 1885 | 315 | inner 1 | cys regulon transcriptional activator cysB |
| 1886 | 217 | cytoplasm | acetate CoA-transferase, alpha subunit |
| 1887 | 233 | cytoplasm | acetate CoA-transferase, beta subunit (atoA) |
| 1888 | 344 | inner 5 | short-chain fatty acids transporter (atoE) |
| 1889 | 84 | inner 1 | short-chain fatty acids transporter (atoE) |
| 1890 | 393 | cytoplasm | acetyl-CoA acetyltransferase (atoB) |
| 1891 | 310 | inner 4 | cell division protein (ftsX) |
| 1892 | 119 | periplasmic | cell division ATP-binding protein (ftsE) |
| 1893 | 129 | cytoplasm | cell division ATP-binding protein (ftsE) |
| 1894 | 175 | cytoplasm | signal recognition particle-docking protein FtsY (ftsY) |
| 1895 | 243 | cytoplasm | peptide ABC transporter, ATP-binding protein (sapD) |
| 1896 | 105 | inner 2 | peptide ABC transporter, permease protein (sapC) |
| 1897 | 50 | periplasmic | peptide ABC transporter, permease protein (sapC) |
| 1898 | 184 | inner 4 | peptide ABC transporter, permease protein (sapC) |
| 1899 | 321 | inner 6 | peptide ABC transporter, permease protein (sapB) |
| 1900 | 564 | outer | peptide ABC transporter, periplasmic-binding protein (sapA) |
| 1903 | 72 | cytoplasm | phosphoenolpyruvate carboxylase (ppc) |
| 1905 | 337 | cytoplasm | oxidoreductase |
| 1906 | 624 | inner 1 | oxidoreductase |
| 1908 | 323 | inner 0 | ferrochelatase (hemH) |
| 1913 | 321 | cytoplasm | thioredoxin reductase (trxB) |
| 1915 | 127 | cytoplasm | thiol peroxidase (tpx) |
| 1917 | 286 | periplasmic | phosphoribosylformylglycinamidine synthase (purL) |
| 1919 | 960 | inner 1 | phosphoribosylformylglycinamidine synthase (purL) |
| 1923 | 247 | inner 0 | lipooligosaccharide biosynthesis protein |
| 1925 | 172 | inner 5 | glp protein |
| 1926 | 235 | cytoplasm | ribosomal large subunit pseudouridine synthase D |
| 1927 | 923 | inner 1 | ATP-dependent helicase (hepA) |
| 1928 | 249 | cytoplasm | L-fucose operon activator (fucR) or transcriptional regulator, DeoR family |
| 1929 | 568 | cytoplasm | ABC transporter, ATP-binding protein |
| 1932 | 440 | cytoplasm | hemoglobin-binding protein |
| 1933 | 158 | cytoplasm | hemoglobin-binding protein |
| 1934 | 140 | cytoplasm | 3,4-dihydroxy-2-butanone 4-phosphate synthase (ribB) or GTP cyclohydrolase |

TABLE III-continued

Annotations
aa = length of polypeptide
PSORT = cellular location of polypeptide, according to PSORT algorithm

| NTH | aa | PSORT | Annotation |
|---|---|---|---|
| 1935 | 282 | inner 1 | lipooligosaccharide biosynthesis protein or lacto-N-neotetraose biosynthesis glycosyl |
| 1936 | 160 | cytoplasm | rRNA methylase |
| 1938 | 355 | cytoplasm | signal recognition particle-docking protein FtsY (ftsY) |
| 1939 | 622 | inner 9 | O-antigen acetylase |
| 1940 | 380 | cytoplasm | ribonuclease D (rnd) |
| 1941 | 562 | inner 2 | long chain fatty acid coenzyme A ligase (fadD) |
| 1942 | 183 | lipo | outer membrane protein |
| 1944 | 158 | cytoplasm | ATP-dependent helicase (dinG) |
| 1949 | 357 | cytoplasm | hemagglutinin/hemolysin-related protein |
| 1950 | 270 | cytoplasm | traN-related protein |
| 1953 | 232 | outer | outer membrane protein P2 (ompP2) |
| 1954 | 366 | cytoplasm | queuosine biosynthesis protein (queA) or S-adenosylmethionine:tRNA |
| 1958 | 1392 | outer | Adhesion and penetration protein |
| 1959 | 504 | cytoplasm | excinuclease ABC, subunit A (uvrA) |
| 1960 | 220 | inner 1 | excinuclease ABC, subunit A (uvrA) |
| 1962 | 384 | outer | membrane-bound lytic murein transglycosylase A |
| 1963 | 261 | inner 1 | HesA/MoeB/ThiF family protein |
| 1965 | 333 | periplasmic | adhesin |
| 1967 | 467 | inner 1 | NMB1183 |
| 1969 | 156 | cytoplasm | transcriptional regulator (ttk) |
| 1971 | 224 | cytoplasm | catabolite gene activator (crp) |
| 1972 | 392 | cytoplasm | tRNA (uracil-5-)-methyltransferase trmA |
| 1973 | 351 | cytoplasm | beta-hexosaminidase (exoII) or glycosyl hydrolase, family 3 |
| 1975 | 299 | cytoplasm | long-chain fatty acid transport protein (fadL) or outer membrane protein P1 |
| 1976 | 189 | cytoplasm | methylated-DNA--protein-cysteine methyltransferase (dat1) |
| 1977 | 87 | cytoplasm | DNA mismatch repair protein (mutH) |
| 1978 | 53 | inner 0 | DNA mismatch repair protein (mutH) |
| 1980 | 71 | cytoplasm | DNA mismatch repair protein (mutH) |
| 1981 | 430 | inner 1 | cell cycle protein (mesJ) |
| 1982 | 34 | cytoplasm | pyridoxine kinase |
| 1983 | 186 | cytoplasm | acetyl-CoA carboxylase, carboxyl transferase subunit alpha |
| 1984 | 141 | cytoplasm | acetyl-CoA carboxylase, carboxyl transferase subunit alpha |
| 1986 | 261 | inner 9 | membrane protein |
| 1988 | 212 | cytoplasm | ABC transporter, ATP-binding protein (yebM) |
| 1989 | 127 | cytoplasm | selenocysteine-specific elongation factor (selB) |
| 1991 | 55 | cytoplasm | selenocysteine-specific elongation factor (selB) or translation elongation factor Tu tufA |
| 1992 | 461 | inner 1 | L-seryl-tRNA selenium transferase (selA) |
| 1993 | 861 | inner 1 | DNA mismatch repair protein (mutS) |
| 1995 | 74 | inner 2 | tryptophan-specific transport protein (mtr) |
| 1996 | 339 | inner 5 | tryptophan-specific transport protein (mtr) |
| 1997 | 81 | inner 2 | ATP synthase F0, subunit a (atpB) |
| 1998 | 88 | inner 1 | ATP synthase F0, subunit c (atpE) |
| 1999 | 156 | periplasmic | ATP synthase F0, subunit b (atpF) |
| 2000 | 144 | cytoplasm | ATP synthase F1, subunit delta (atpH) |
| 2001 | 41 | inner 0 | ATP synthase F1, subunit delta (atpH) |
| 2002 | 513 | cytoplasm | ATP synthase F1, subunit alpha (atpA) |
| 2003 | 289 | cytoplasm | ATP synthase F1, subunit gamma (atpG) |
| 2005 | 76 | inner 1 | ATP synthase F1, subunit beta (atpD) |
| 2007 | 372 | cytoplasm | ATP synthase F1, subunit beta (atpD) |
| 2008 | 147 | inner 1 | ATP synthase F1, subunit epsilon (atpC) |
| 2009 | 54 | inner 1 | tyrosine-specific transport protein (tyrP) |
| 2010 | 117 | inner 1 | ribosomal protein L20 (rpL20) |
| 2011 | 77 | cytoplasm | exodeoxyribonuclease V, beta chain (recB) |
| 2012 | 1086 | cytoplasm | exodeoxyribonuclease V, beta chain (recB) |
| 2013 | 288 | cytoplasm | exodeoxyribonuclease V, alpha chain (recD) |
| 2014 | 47 | cytoplasm | exodeoxyribonuclease V, alpha chain (recD) |
| 2016 | 194 | cytoplasm | exodeoxyribonuclease V, alpha chain (recD) |
| 2021 | 107 | cytoplasm | virulence associated protein A (vapA) |
| 2022 | 556 | cytoplasm | ABC transporter, ATP-binding protein |
| 2028 | 435 | cytoplasm | transcription-repair coupling factor (mfd) |
| 2029 | 228 | cytoplasm | transcription-repair coupling factor (mfd) |
| 2030 | 392 | cytoplasm | transcription-repair coupling factor (mfd) |
| 2031 | 36 | cytoplasm | transcription-repair coupling factor (mfd) |
| 2032 | 86 | cytoplasm | leucyl-tRNA synthetase (leuS) |
| 2034 | 688 | cytoplasm | leucyl-tRNA synthetase (leuS) |
| 2036 | 281 | cytoplasm | undecaprenyl diphosphate synthase |
| 2038 | 288 | inner 7 | CDP-diglyceride synthetase (cdsA) |
| 2041 | 283 | inner 2 | protective surface antigen D15 Omp85 |
| 2044 | 256 | cytoplasm | RNA polymerase sigma-70 factor (rpoD) |
| 2045 | 300 | cytoplasm | RNA polymerase sigma-70 factor (rpoD) |
| 2046 | 347 | cytoplasm | DNA primase (dnaG) |
| 2047 | 191 | cytoplasm | DNA primase (dnaG) |

TABLE III-continued

Annotations
aa = length of polypeptide
PSORT = cellular location of polypeptide, according to PSORT algorithm

| NTH | aa | PSORT | Annotation |
|---|---|---|---|
| 2048 | 52 | cytoplasm | DNA primase (dnaG) |
| 2049 | 71 | cytoplasm | ribosomal protein S21 (rpS21) |
| 2050 | 342 | inner 1 | O-sialoglycoprotein endopeptidase (gcp) |
| 2051 | 206 | cytoplasm | thymidine kinase (tdk) |
| 2052 | 406 | inner 10 | tyrosine-specific transport protein (tyrP) or tryptophan transporter mtr |
| 2053 | 86 | cytoplasm | ferredoxin, 4Fe—4S bacterial type (fdx-2) |
| 2058 | 263 | cytoplasm | phosphoglycerate kinase (pgk) |
| 2059 | 81 | cytoplasm | phosphoglycerate kinase (pgk) |
| 2061 | 207 | cytoplasm | amino acid ABC transporter, ATP-binding protein |
| 2062 | 79 | inner 0 | amino acid ABC transporter, ATP-binding protein |
| 2065 | 230 | inner 4 | ribonuclease BN (rbn) |
| 2066 | 53 | cytoplasm | ribonuclease BN (rbn) |
| 2070 | 273 | inner 1 | uridine phosphorylase (udp) |
| 2071 | 438 | inner 9 | transport protein |
| 2073 | 568 | inner 1 | 2-succinyl-6-hydroxy-2,4-cyclohexadiene-1-carboxylate |
| 2074 | 185 | cytoplasm | menaquinone-specific isochorismate synthase (menF) or anthranilate synthase component I trpE |
| 2076 | 679 | cytoplasm | excinuclease ABC, subunit B (uvrB) |
| 2079 | 756 | inner 4 | malate oxidoreductase |
| 2081 | 238 | inner 5 | tyrosine-specific transport protein (tyrP) or tryptophan transporter mtr |
| 2083 | 228 | inner 0 | phosphoribosyl-AMP cyclohydrolase/phosphoribosyl-ATP |
| 2084 | 258 | cytoplasm | hisF cyclase (hisF) |
| 2085 | 249 | cytoplasm | phosphoribosylformimino-5-aminoimidazole carboxamide |
| 2086 | 199 | cytoplasm | amidotransferase (hisH) |
| 2087 | 381 | cytoplasm | imidazoleglycerol-phosphate dehydratase/ |
| 2088 | 367 | cytoplasm | histidinol-phosphate aminotransferase (hisC) |
| 2089 | 427 | inner 1 | histidinol dehydrogenase (hisD) |
| 2090 | 35 | cytoplasm | ATP phosphoribosyltransferase (hisG) |
| 2091 | 199 | inner 1 | biotin operon repressor/biotin acetyl coenzyme A or BirA protein/Bvg accessory factor |
| 2092 | 488 | inner 1 | inosine-5'-monophosphate dehydrogenase (guaB) |
| 2094 | 523 | inner 1 | GMP synthase (guaA) |
| 2095 | 296 | inner 7 | rarD protein |
| 2097 | 168 | inner 0 | transcriptional regulator |
| 2099 | 321 | inner 10 | Na+/H+ antiporter (nhaA) |
| 2100 | 32 | cytoplasm | hemolysin |
| 2101 | 522 | inner 7 | apolipoprotein N-acyltransferase (cutE) |
| 2106 | 193 | cytoplasm | recombination associated protein RdgC rdgC |
| 2108 | 105 | cytoplasm | recombination associated protein RdgC rdgC |
| 2110 | 290 | cytoplasm | integrase/recombinase |
| 2115 | 158 | inner 4 | colicin V production protein (cvpA) |
| 2118 | 441 | inner 2 | acetate kinase (ackA) |
| 2119 | 331 | periplasmic | phosphate acetyltransferase (pta) |
| 2120 | 403 | inner 1 | phosphate acetyltransferase (pta) |
| 2122 | 314 | inner 1 | adenine specific methylase |
| 2123 | 323 | cytoplasm | cys regulon transcriptional activator (cysB) |
| 2124 | 71 | cytoplasm | phosphoribosylaminoimidazole carboxylase, catalytic subunit |
| 2126 | 362 | inner 1 | phosphoribosylaminoimidazole carboxylase, ATPase subunit |
| 2127 | 396 | cytoplasm | aspartate aminotransferase (aspC) |
| 2128 | 220 | inner 1 | spermidine/putrescine ABC transporter, ATP-binding |
| 2134 | 152 | cytoplasm | mercuric resistance operon regulatory protein (merR2) |
| 2138 | 560 | inner 10 | PTS system, fructose-specific IIBC component (fruA) |
| 2139 | 313 | cytoplasm | 1-phosphofructokinase (fruK) or ADP-heptose synthase |
| 2140 | 499 | cytoplasm | PTS system, fructose-specific IIA/FPr component (fruB) |
| 2143 | 92 | cytoplasm | virulence associated protein D (vapD) |
| 2146 | 101 | inner 1 | hypoxanthine phosphoribosyltransferase (hpt) |
| 2147 | 451 | cytoplasm | pmbA protein (pmbA) |
| 2151 | 241 | cytoplasm | ABC transporter, ATP-binding protein |
| 2152 | 164 | cytoplasm | nitrogen regulatory IIA protein (ptsN) |
| 2155 | 202 | cytoplasm | chorismate mutase/prephenate dehydratase (pheA) |
| 2157 | 148 | cytoplasm | ABC transporter, ATP-binding protein |
| 2158 | 192 | cytoplasm | histidinol-phosphatase |
| 2160 | 221 | cytoplasm | 5,10 methylenetetrahydrofolate reductase (metF) |
| 2161 | 89 | cytoplasm | dethiobiotin synthase (bioD-1) |
| 2162 | 313 | inner 5 | TRK system potassium uptake protein (trkH) or bis(5'-nucleosyl)-tetraphosphatase, symmetrical/Trk |
| 2163 | 191 | inner 3 | TRK system potassium uptake protein (trkH) or bis(5'-nucleosyl)-tetraphosphatase, symmetrical/Trk |
| 2166 | 288 | inner 4 | heat shock protein (htpX) |
| 2168 | 130 | cytoplasm | ribonuclease |
| 2169 | 244 | inner 0 | lipoprotein (vacJ) |
| 2172 | 185 | cytoplasm | transcription antitermination protein (nusG) |
| 2173 | 138 | inner 3 | preprotein translocase SecE subunit (secE) |
| 2175 | 411 | cytoplasm | ATP-dependent Clp protease, ATP-binding subunit (clpX) |

TABLE III-continued

Annotations
aa = length of polypeptide
PSORT = cellular location of polypeptide, according to PSORT algorithm

| NTH | aa | PSORT | Annotation |
|---|---|---|---|
| 2176 | 211 | cytoplasm | ATP-dependent Clp protease, proteolytic subunit (clpP) |
| 2177 | 394 | cytoplasm | trigger factor (tig) |
| 2178 | 52 | cytoplasm | trigger factor (tig) |
| 2180 | 89 | cytoplasm | ribosomal protein S20 (rpS20) |
| 2181 | 524 | inner 11 | virulence factor (mviN) |
| 2182 | 312 | cytoplasm | riboflavin kinase/FMN adenylyltransferase (ribF) |
| 2183 | 484 | inner 1 | isoleucyl-tRNA synthetase ileS |
| 2184 | 485 | cytoplasm | isoleucyl-tRNA synthetase ileS |
| 2185 | 102 | cytoplasm | hit-related protein |
| 2186 | 184 | cytoplasm | lipoprotein |
| 2187 | 393 | periplasmic | penicillin-binding protein 5 (dacA) |
| 2189 | 212 | cytoplasm | lipoate biosynthesis protein B (lipB) |
| 2190 | 320 | cytoplasm | lipoate biosynthesis protein A (lipA) |
| 2191 | 335 | inner 1 | citrate lyase ligase (citC) |
| 2192 | 95 | cytoplasm | citrate lyase, gamma chain (citD) |
| 2193 | 291 | inner 0 | citrate lyase, beta chain (citE) |
| 2195 | 500 | inner 1 | citrate lyase, alpha chain (citF) |
| 2196 | 416 | inner 1 | citG protein (citG) |
| 2200 | 256 | inner 1 | heme-hemopexin utilization protein A (hxuA) |
| 2202 | 458 | cytoplasm | DNA repair protein (radA) |
| 2204 | 166 | inner 1 | leucine responsive regulatory protein (lrp) |
| 2205 | 554 | inner 5 | cell division protein FtsK ftsK-1 |
| 2208 | 169 | cytoplasm | polypeptide deformylase (def) |
| 2209 | 318 | inner 1 | methionyl-tRNA formyltransferase (fmt) |
| 2211 | 450 | cytoplasm | sun protein (sun) or 16S RNA methyltransferase rsmB |
| 2212 | 458 | cytoplasm | TRK system potassium uptake protein (trkA) |
| 2213 | 134 | inner 2 | large conductance mechanosensitive channel (mscL) |
| 2215 | 40 | cytoplasm | RNA polymerase sigma-E factor (rpoE) |
| 2231 | 347 | inner 1 | lipopolysaccharide biosynthesis protein or ADP-heptose--LPS heptosyltransferase II rfaF |
| 2232 | 539 | outer | heme-hemopexin utilization protein C or iron-regulated outer membrane protein FrpB frpB |
| 2233 | 170 | cytoplasm | heme-hemopexin utilization protein C |
| 2234 | 565 | outer | heme-hemopexin utilization protein B (hxuB) |
| 2235 | 758 | outer-hand | heme-hemopexin utilization protein A (hxuA) |
| 2236 | 231 | cytoplasm | DNA ligase ligA-2 |
| 2238 | 327 | cytoplasm | dipeptide ABC transporter, ATP-binding protein (dppF) |
| 2241 | 330 | cytoplasm | dipeptide ABC transporter, ATP-binding protein (dppD) |
| 2242 | 295 | inner 6 | dipeptide ABC transporter, permease protein (dppC) or thiol:disulfide interchange protein DsbD dsbD |
| 2243 | 333 | inner 5 | dipeptide ABC transporter, permease protein (dppB) |
| 2246 | 727 | cytoplasm | DNA helicase II (uvrD) |
| 2249 | 141 | cytoplasm | 6-pyruvoyl tetrahydrobiopterin synthase |
| 2250 | 227 | inner 0 | aluminum resistance protein |
| 2252 | 184 | cytoplasm | branched-chain-amino-acid transaminase (ilvE) |
| 2259 | 898 | inner 1 | exodeoxyribonuclease V, gamma chain (recC) |
| 2260 | 163 | cytoplasm | exodeoxyribonuclease V, gamma chain (recC) |
| 2262 | 372 | inner 1 | riboflavin biosynthesis protein (ribD) |
| 2263 | 357 | inner 1 | protease (degS) |
| 2274 | 192 | inner 0 | molybdopterin-guanine dinucleotide biosynthesis protein |
| 2277 | 216 | periplasmic | periplasmic oxidoreductase (por) or thiol:disulfide interchange protein DsbA dsbA-2 |
| 2280 | 363 | cytoplasm | tRNA (uracil-5-)-methyltransferase (trmA) |
| 2282 | 125 | inner 1 | sigma-E factor regulatory protein |
| 2283 | 33 | cytoplasm | sigma-E factor regulatory protein |
| 2285 | 178 | inner 0 | molybdopterin-guanine dinucleotide biosynthesis protein B |
| 2289 | 652 | cytoplasm | ATP-dependent Clp protease, ATPase subunit (clpB) |
| 2293 | 156 | cytoplasm | DNA polymerase I (polA) |
| 2294 | 785 | cytoplasm | DNA polymerase I (polA) |
| 2299 | 507 | inner 0 | N utilization substance protein A (nusA) |
| 2301 | 855 | cytoplasm | translation initiation factor 2 (infB) |
| 2303 | 466 | cytoplasm | type I restriction enzyme (hsdR) |
| 2304 | 285 | cytoplasm | type I restriction enzyme (hsdR) |
| 2307 | 518 | cytoplasm | anthranilate synthase component I (trpE) |
| 2308 | 195 | cytoplasm | anthranilate synthase component II (trpG) or para-aminobenzoate synthase glutamine |
| 2311 | 84 | cytoplasm | anthanilate phosphoribosyltransferase (trpD) |
| 2313 | 231 | cytoplasm | anthanilate phosphoribosyltransferase (trpD) |
| 2314 | 477 | cytoplasm | indole-3-glycerol phosphate synthase/ |
| 2317 | 239 | cytoplasm | valyl-tRNA synthetase (valS) |
| 2318 | 425 | inner 1 | valyl-tRNA synthetase (valS) |
| 2319 | 35 | cytoplasm | valyl-tRNA synthetase (valS) |
| 2321 | 150 | cytoplasm | valyl-tRNA synthetase (valS) |
| 2322 | 102 | cytoplasm | valyl-tRNA synthetase (valS) |

TABLE III-continued

Annotations
aa = length of polypeptide
PSORT = cellular location of polypeptide, according to PSORT algorithm

| NTH | aa | PSORT | Annotation |
|---|---|---|---|
| 2324 | 42 | inner 1 | transport protein |
| 2325 | 238 | cytoplasm | purine-nucleoside phosphorylase (deoD) or 5-methylthioadenosine |
| 2327 | 142 | inner 0 | ribosomal protein L11 (rpL11) |
| 2328 | 229 | cytoplasm | ribosomal protein L1 (rpL1) |
| 2329 | 1298 | cytoplasm | DNA-directed RNA polymerase, beta chain (rpoB) |
| 2331 | 158 | cytoplasm | iron(III) ABC transporter, periplasmic-binding protein |
| 2333 | 506 | inner 11 | iron(III) ABC transporter, permease protein (hitB) |
| 2335 | 356 | cytoplasm | iron(III) ABC transporter, ATP-binding protein (hitC) |
| 2338 | 377 | cytoplasm | succinyl-diaminopimelate desuccinylase (dapE) |
| 2341 | 631 | cytoplasm | heat shock protein (htpG) |
| 2344 | 106 | periplasmic | organic solvent tolerance protein |
| 2345 | 667 | cytoplasm | organic solvent tolerance protein |
| 2346 | 572 | inner 1 | prolyl-tRNA synthetase (proS) |
| 2347 | 630 | inner 1 | ATP-dependent DNA helicase (recQ) |
| 2348 | 113 | cytoplasm | cyaY protein (cyaY) |
| 2350 | 415 | cytoplasm | diaminopimelate decarboxylase (lysA) |
| 2351 | 208 | cytoplasm | nitrate/nitrite response regulator protein (narP) or transcriptional regulator, LuxR family |
| 2354 | 203 | cytoplasm | pseudouridine synthase RluD (rluD) or ribosomal large subunit pseudouridine synthase D |
| 2356 | 272 | lipo | lipoprotein or competence lipoprotein ComL comL |
| 2359 | 246 | cytoplasm | pyruvate formate-lyase activating enzyme (act) |
| 2360 | 772 | cytoplasm | formate acetyltransferase (pfl) |
| 2361 | 286 | inner 6 | formate transporter |
| 2365 | 276 | inner 2 | sugar kinase |
| 2368 | 377 | inner 5 | amino acid carrier protein |
| 2371 | 158 | inner 0 | YgbB/YacN family protein |
| 2373 | 146 | cytoplasm | mioC protein (mioC) or sulfite reductase (NADPH) flavoprotein, alpha |
| 2376 | 333 | inner 1 | glpX protein (glpX) |
| 2381 | 551 | inner 6 | ABC transporter, ATP-binding protein |
| 2382 | 360 | inner 2 | ATP-binding transport protein (cydD) |
| 2383 | 228 | cytoplasm | heat shock protein (grpE) |
| 2385 | 520 | cytoplasm | DNA repair protein (recN) |
| 2387 | 38 | cytoplasm | DNA repair protein (recN) |
| 2388 | 981 | inner 1 | glutamate-ammonia-ligase adenylyltransferase (glnE) |
| 2389 | 311 | cytoplasm | tRNA delta(2)-isopentenylpyrophosphate transferase (trpX) |
| 2390 | 390 | cytoplasm | DNA mismatch repair protein (mutL) |
| 2391 | 123 | cytoplasm | thymidylate synthetase (thyA) |
| 2392 | 173 | cytoplasm | cytidine and deoxycytidylate deaminase family |
| 2395 | 545 | cytoplasm | preprotein translocase SecA subunit (secA) |
| 2396 | 363 | cytoplasm | preprotein translocase SecA subunit (secA) |
| 2397 | 163 | cytoplasm | mutator mutT protein (mutT) |
| 2398 | 618 | inner 10 | glutathione-regulated potassium efflux system protein (kefC) |
| 2399 | 254 | cytoplasm | 3-demethylubiquinone-9 3-methyltransferase ubiG |
| 2401 | 245 | cytoplasm | ribosomal protein S2 (rpS2) |
| 2402 | 71 | inner 1 | preprotein translocase SecY subunit (secY) |
| 2403 | 144 | cytoplasm | ribosomal protein L15 (rpL15) |
| 2404 | 59 | cytoplasm | ribosomal protein L30 (rpL30) |
| 2405 | 267 | inner 1 | glucosamine--fructose-6-phosphate aminotransferase (glmS) |
| 2406 | 177 | inner 3 | disulfide bond formation protein B (dsbB) |
| 2407 | 238 | inner 5 | Na+/H+ antiporter (nhaB) |
| 2408 | 292 | inner 5 | Na+/H+ antiporter (nhaB) |
| 2410 | 241 | cytoplasm | fatty acid metabolism regulator protein (fadR) |
| 2411 | 455 | cytoplasm | phosphatidylserine synthase (pssA) or cardiolipin synthetase family protein |
| 2412 | 201 | cytoplasm | rRNA methylase |
| 2413 | 232 | cytoplasm | adenine specific methylase |
| 2415 | 122 | cytoplasm | ATP-dependent RNA helicase SrmB (srmB) |
| 2416 | 287 | cytoplasm | ATP-dependent RNA helicase SrmB (srmB) |
| 2417 | 231 | cytoplasm | protease |
| 2418 | 203 | cytoplasm | ATP phosphoribosyltransferase (hisG) |
| 2421 | 410 | cytoplasm | D-3-phosphoglycerate dehydrogenase (serA) |
| 2422 | 219 | inner 1 | ribose 5-phosphate isomerase A (rpiA) |
| 2423 | 383 | cytoplasm | oxygen-independent coproporphyrinogen III oxidase |
| 2424 | 658 | cytoplasm | ATP-dependent proteinase (lon) |
| 2428 | 298 | cytoplasm | transcriptional regulator, araC family |
| 2429 | 38 | cytoplasm | ABC transporter, ATP-binding protein |
| 2430 | 576 | inner 4 | ABC transporter, ATP-binding protein |
| 2432 | 92 | periplasmic | mercuric ion scavenger protein (merP) |
| 2433 | 120 | inner 3 | mercuric ion transport protein (merT) |
| 2435 | 472 | cytoplasm | anaerobic dimethyl sulfoxide reductase, chain A (dmsA) |
| 2436 | 352 | cytoplasm | anaerobic dimethyl sulfoxide reductase, chain A (dmsA) |
| 2437 | 205 | cytoplasm | anaerobic dimethyl sulfoxide reductase, chain B (dmsB) |
| 2438 | 279 | inner 7 | anaerobic dimethyl sulfoxide reductase, chain C (dmsC) |
| 2440 | 166 | cytoplasm | ferredoxin-type protein (napF) or NADH dehydrogenase I, I subunit nuoI |

TABLE III-continued

Annotations
aa = length of polypeptide
PSORT = cellular location of polypeptide, according to PSORT algorithm

| NTH | aa | PSORT | Annotation |
|---|---|---|---|
| 2443 | 133 | cytoplasm | 2-isopropylmalate synthase (leuA) |
| 2445 | 358 | cytoplasm | 3-isopropylmalate dehydrogenase (beta-IPM dehydrogenase) |
| 2446 | 469 | cytoplasm | 3-isopropylmalate dehydratase, alpha subunit (leuC) |
| 2447 | 200 | inner 0 | 3-isopropylmalate dehydratase small subunit (leuD) |
| 2448 | 1794 | outer-hand | immunoglobin A1 protease (iga1) or IgA-specific serine endopeptidase iga |
| 2449 | 378 | cytoplasm | DNA/ATP binding protein (recF) |
| 2450 | 366 | cytoplasm | DNA polymerase III, beta subunit (dnaN) |
| 2452 | 454 | cytoplasm | chromosomal replication initiator protein (dnaA) |
| 2453 | 118 | cytoplasm | transferrin-binding protein 1 precursor (tbp1) |
| 2454 | 231 | cytoplasm | transferrin-binding protein 1 precursor (tbp1) |
| 2457 | 199 | inner 1 | baseplate assembly protein V |
| 2462 | 861 | cytoplasm | tail fibre protein |
| 2476 | 69 | cytoplasm | aspartokinase I/homoserine dehydrogenase I (thrA) |
| 2477 | 307 | cytoplasm | aspartokinase I/homoserine dehydrogenase I (thrA) |
| 2478 | 314 | inner 1 | homoserine kinase (thrB) |
| 2479 | 425 | cytoplasm | threonine synthase (thrC) |
| 2480 | 238 | cytoplasm | integrase/recombinase (xerC) |
| 2491 | 176 | cytoplasm | ferredoxin-type 4Fe—4S protein (napF) |
| 2492 | 93 | cytoplasm | napD protein (napD) |
| 2493 | 832 | outer-hand | Formate dehydrogenase major subunit |
| 2494 | 279 | cytoplasm | ferredoxin-type protein (napG) |
| 2495 | 287 | inner 4 | ferredoxin-type 4Fe—4S protein (napH) |
| 2496 | 150 | periplasmic | periplasmic nitrate reductase (napB) |
| 2497 | 200 | inner 1 | cytochrome C-type protein (napC) |
| 2498 | 214 | inner 0 | adenylate kinase (adk) |
| 2499 | 412 | inner 10 | permease or AmpG-related protein |
| 2501 | 241 | inner 0 | UDP-glucose 4-epimerase (galE) |
| 2502 | 82 | cytoplasm | UDP-glucose 4-epimerase (galE) |
| 2504 | 244 | cytoplasm | iron(III) ABC transporter, ATP-binding protein fbpC |
| 2505 | 176 | inner 4 | ABC transporter, permease protein |
| 2508 | 241 | periplasmic | FkbP-type peptidyl-prolyl cis-trans isomerase (fkpA) or macrophage infectivity potentiator |
| 2509 | 73 | cytoplasm | slyX protein (slyX) |
| 2511 | 33 | cytoplasm | peroxiredoxin 2 family protein/glutaredoxin |
| 2512 | 48 | cytoplasm | peroxiredoxin 2 family protein/glutaredoxin |
| 2513 | 117 | cytoplasm | peroxiredoxin 2 family protein/glutaredoxin |
| 2514 | 301 | cytoplasm | hydrogen peroxide-inducible genes activator (oxyR) or transcriptional regulator, LysR family |
| 2517 | 158 | cytoplasm | transcription elongation factor (greB) |
| 2518 | 770 | cytoplasm | transcription accessory protein (tex) |
| 2519 | 736 | cytoplasm | DNA gyrase, subunit B (gyrB) |
| 2520 | 59 | cytoplasm | DNA gyrase, subunit B (gyrB) |
| 2521 | 234 | cytoplasm | ribulose-phosphate 3-epimerase (dod) |
| 2522 | 224 | cytoplasm | phosphoglycolate phosphatase (gph) |
| 2530 | 132 | cytoplasm | transposase |
| 2531 | 369 | inner 8 | multidrug resistance protein B (emrB) or fatty acid efflux system protein farB |
| 2532 | 256 | inner 1 | cell division protein (ftsN) |
| 2533 | 1032 | inner 12 | acriflavine resistance protein (acrB) or multiple transferable resistance system protein MtrD |
| 2534 | 419 | inner 1 | lipoprotein or membrane fusion protein mtrC |
| 2535 | 196 | cytoplasm | transcriptional repressor (Bm3R1) or trancscriptional regulator MtrR mtrR |
| 2538 | 418 | inner 1 | ATP-dependent RNA helicase (rhlB) |
| 2541 | 210 | periplasmic | kinase |
| 2542 | 421 | inner 1 | serine hydroxymethyltransferase (serine methylase) (glyA) |
| 2543 | 478 | inner 3 | YhbX/YhjW/YijP/YjdB family protein |
| 2544 | 85 | cytoplasm | phosphoribosylamine--glycine ligase (purD) |
| 2545 | 101 | inner 1 | cell division protein (ftsQ) |
| 2546 | 306 | inner 0 | D-alanine--D-alanine ligase (ddlB) |
| 2548 | 475 | inner 2 | UDP-N-acetylmuramate--alanine ligase (murC) |
| 2550 | 351 | inner 1 | UDP-N-acetylglucosamine--N-acetylmuramyl-(pentapeptide) |
| 2552 | 394 | inner 9 | cell division protein (ftsW) |
| 2553 | 437 | cytoplasm | UDP-N-acetylmuramoylalanine--D-glutamate ligase (murD) |
| 2554 | 360 | inner 10 | phospho-N-acetylmuramoyl-pentapeptide-transferase E (mraY) |
| 2555 | 457 | cytoplasm | UDP-MurNAc-pentapeptide synthetase (murF) |
| 2556 | 488 | inner 1 | UDP-N-acetylmuramyl-tripeptide synthetase (murE) |
| 2557 | 610 | inner 1 | penicillin-binding protein 3 (ftsI) |
| 2558 | 107 | inner 1 | cell division protein (ftsL) |
| 2561 | 208 | cytoplasm | fuculokinase (fucK) |
| 2564 | 68 | cytoplasm | transcriptional regulatory protein (asnC) |
| 2569 | 269 | inner 0 | sulfite synthesis pathway protein (cysQ) or inositol monophosphatase family protein |
| 2570 | 474 | inner 0 | glucose-6-phosphate 1-dehydrogenase (zwf) |
| 2571 | 245 | cytoplasm | oxidoreductase (devB) |

TABLE III-continued

Annotations
aa = length of polypeptide
PSORT = cellular location of polypeptide, according to PSORT algorithm

| NTH | aa | PSORT | Annotation |
|---|---|---|---|
| 2577 | 392 | inner 1 | 6-phosphogluconate dehydrogenase, decarboxylating (gnd) |
| 2578 | 76 | inner 0 | 6-phosphogluconate dehydrogenase, decarboxylating (gnd) |
| 2581 | 275 | cytoplasm | diadenosine-tetraphosphatase (apaH) or bis(5'-nucleosyl)-tetraphosphatase, symmetrical/Trk |
| 2582 | 312 | cytoplasm | lipooligosaccharide biosynthesis protein or lacto-N-neotetraose biosynthesis glycosyl |
| 2583 | 287 | cytoplasm | dimethyladenosine transferase (ksgA) |
| 2584 | 253 | cytoplasm | lipopolysaccharide glycosyl transferase |
| 2585 | 65 | cytoplasm | lipopolysaccharide glycosyl transferase |
| 2586 | 84 | cytoplasm | translation initiation factor 1 (infA) |
| 2587 | 480 | inner 8 | glycerol-3-phosphatase transporter (glpT) |
| 2588 | 364 | lipo | glycerophosphoryl diester phosphodiesterase (glpQ) |
| 2591 | 217 | inner 4 | glycerol uptake facilitator protein (glpF) |
| 2592 | 503 | cytoplasm | glycerol kinase (glpK) |
| 2593 | 155 | inner 1 | xanthine-guanine phosphoribosyltransferase (gptB) |
| 2594 | 45 | cytoplasm | glycerophosphoryl diester phosphodiesterase (glpQ) |
| 2595 | 274 | lipo | lipoprotein E (hel) |
| 2597 | 132 | inner 1 | exopolyphosphatase |
| 2598 | 212 | cytoplasm | exopolyphosphatase |
| 2600 | 133 | inner 1 | peptide chain release factor 3 (prfC) |
| 2606 | 309 | cytoplasm | transcriptional activator (metR) |
| 2610 | 89 | periplasmic | pyrroline-5-carboxylate reductase (proC) |
| 2612 | 189 | inner 0 | pyrroline-5-carboxylate reductase (proC) |
| 2617 | 297 | cytoplasm | integrase/recombinase (xerD) |
| 2619 | 335 | cytoplasm | Holliday junction DNA helicase (ruvB) |
| 2620 | 204 | cytoplasm | Holliday junction DNA helicase (ruvA) |
| 2621 | 190 | cytoplasm | crossover junction endodeoxyribonuclease (ruvC) |
| 2623 | 156 | cytoplasm | datP pyrophosphohydrolase (ntpA) |
| 2625 | 588 | cytoplasm | aspartyl-tRNA synthetase (aspS) |
| 2629 | 78 | cytoplasm | virulence associated protein B (vapB) |
| 2630 | 134 | cytoplasm | virulence associated protein C |
| 2631 | 135 | cytoplasm | lactoylglutathione lyase (gloA) |
| 2632 | 229 | cytoplasm | ribonuclease T (rnt) |
| 2636 | 188 | cytoplasm | translation elongation factor P (efp) |
| 2640 | 431 | inner 1 | opacity associated protein (oapA) |
| 2641 | 134 | lipo | opacity associated protein (oapB) |
| 2642 | 236 | cytoplasm | DNA repair protein (recO) |
| 2643 | 438 | cytoplasm | tRNA (uracil-5-)-methyltransferase trmA |
| 2644 | 651 | cytoplasm | elongation factor G (fusA) |
| 2646 | 394 | cytoplasm | elongation factor Tu (tufB) |
| 2647 | 75 | inner 2 | chloride channel protein-related protein |
| 2649 | 245 | inner 3 | chloride channel protein-related protein |
| 2654 | 336 | cytoplasm | tryptophanyl-tRNA synthetase (trpS) |
| 2657 | 92 | cytoplasm | adenylosuccinate lyase (purB) |
| 2659 | 364 | cytoplasm | adenylosuccinate lyase (purB) |
| 2660 | 163 | cytoplasm | ribosomal protein L10 (rpL10) |
| 2661 | 126 | inner 0 | ribosomal protein L7/L12 (rpL7/L12) |
| 2663 | 456 | inner 0 | UDP-N-acetylglucosamine pyrophosphorylase (glmU) |
| 2665 | 311 | cytoplasm | lysophospholipase L2 (pldB) |
| 2666 | 371 | cytoplasm | aspartate-semialdehyde dehydrogenase (asd) |
| 2667 | 243 | inner 4 | transport protein |
| 2670 | 136 | cytoplasm | modulator of drug activity B (mdaB) |
| 2671 | 42 | cytoplasm | modulator of drug activity B (mdaB) |
| 2672 | 676 | cytoplasm | ATP-dependent DNA helicase (rep) |
| 2674 | 156 | inner 1 | lipopolysaccharide core biosynthesis protein (kdtB) |
| 2675 | 427 | inner 2 | 3-deoxy-d-manno-octulosonic-acid transferase (kdtA) |
| 2676 | 254 | cytoplasm | lipopolysaccharide biosynthesis protein or beta-1,4-glucosyltransferase lgtF |
| 2678 | 192 | cytoplasm | DNA-3-methyladenine glycosidase I (tagI) |
| 2680 | 268 | inner 1 | shikimate 5-dehydrogenase (aroE) |
| 2682 | 178 | cytoplasm | DNA topoisomerase I topA |
| 2683 | 63 | cytoplasm | ABC transporter, ATP-binding protein |
| 2685 | 115 | cytoplasm | anaerobic ribonucleoside-triphosphate reductase (nrdD) |
| 2686 | 272 | cytoplasm | anaerobic ribonucleoside-triphosphate reductase (nrdD) |
| 2687 | 286 | cytoplasm | acyl-CoA thioesterase II (tesB) |
| 2688 | 469 | cytoplasm | cysteinyl-tRNA synthetase (cysS) |
| 2689 | 169 | cytoplasm | peptidyl-prolyl cis-trans isomerase B (ppiB) |
| 2698 | 107 | cytoplasm | thioredoxin (trxM) |
| 2701 | 335 | inner 1 | D-lactate dehydrogenase, fermentative (ldhA) |
| 2702 | 393 | inner 1 | cystathionine gamma-synthase (metB) |
| 2703 | 175 | inner 1 | ParA family protein |
| 2705 | 451 | periplasmic | replicative DNA helicase (dnaB) |
| 2714 | 140 | cytoplasm | single-stranded DNA binding protein (ssb) |
| 2717 | 686 | cytoplasm | DNA topoisomerase III (topB) |
| 2722 | 156 | cytoplasm | DNA repair protein (radC) |

TABLE III-continued

Annotations
aa = length of polypeptide
PSORT = cellular location of polypeptide, according to PSORT algorithm

| NTH | aa | PSORT | Annotation |
|---|---|---|---|
| 2733 | 150 | cytoplasm | mutT protein mutT |
| 2735 | 170 | inner 3 | transport protein |
| 2736 | 280 | cytoplasm | aspartate ammonia-lyase (aspA) |
| 2738 | 236 | periplasmic | aspartokinase I/homoserine dehydrogenase I (thrA) |
| 2739 | 317 | cytoplasm | transaldolase B (talB) |
| 2740 | 217 | inner 1 | glyceraldehyde-3-phosphate dehydrogenase (gapdH) |
| 2741 | 34 | cytoplasm | inner membrane protein, 60 kDa (yidC) |
| 2742 | 204 | cytoplasm | inner membrane protein, 60 kDa (yidC) |
| 2745 | 229 | cytoplasm | sufI protein (sufI) |
| 2747 | 167 | cytoplasm | heat shock protein (hslU) or ATP-dependent Clp protease, ATP-binding subunit |
| 2748 | 94 | cytoplasm | spermidine/putrescine ABC transporter, periplasmic-binding |
| 2749 | 287 | inner 8 | drug resistance translocase family protein |
| 2750 | 325 | inner 2 | potassium/copper-transporting ATPase or cation transport ATPase, E1-E2 family |
| 2751 | 349 | cytoplasm | 2-oxoglutarate dehydrogenase E1 component (sucA) |
| 2752 | 34 | cytoplasm | 2-oxoglutarate dehydrogenase E1 component (sucA) |
| 2755 | 38 | inner 1 | serine transporter (sdaC) |
| 2756 | 217 | inner 4 | serine transporter (sdaC) |
| 2758 | 75 | lipo | thermonuclease family protein |
| 2761 | 144 | cytoplasm | orfG protein |
| 2762 | 51 | cytoplasm | methionine aminopeptidase (map) |
| 2763 | 343 | cytoplasm | protein-PII uridylyltransferase glnD |
| 2764 | 107 | inner 4 | transporter |
| 2765 | 282 | inner 5 | protein-export membrane protein (secF) |
| 2766 | 96 | cytoplasm | recA protein (recA) |
| 2768 | 152 | cytoplasm | regulatory protein (recX) |
| 2769 | 111 | lipo | crcB protein |
| 2772 | 163 | cytoplasm | transcriptional regulatory protein (tyrR) or nitrogen assimilation regulatory protein NtrX ntrX |
| 2774 | 209 | inner 1 | glutathione transferase (bphH) or stringent starvation protein A sspA |
| 2780 | 43 | cytoplasm | CTP synthetase (pyrG) |
| 2782 | 138 | cytoplasm | CTP synthetase (pyrG) |
| 2785 | 167 | cytoplasm | transcriptional regulator |
| 2786 | 93 | cytoplasm | guanylate kinase (gmk) |
| 2788 | 88 | cytoplasm | DNA-directed RNA polymerase, omega chain (rpoZ) |
| 2789 | 84 | cytoplasm | guanosine-3',5'-bis(diphosphate) 3'-pyrophosphohydrolase |
| 2790 | 38 | cytoplasm | guanosine-3',5'-bis(diphosphate) 3'-pyrophosphohydrolase |
| 2792 | 90 | cytoplasm | S-adenosylmethionine:2-demethylmenaquinone methyltransferase |
| 2795 | 120 | cytoplasm | rbs repressor (rbsR) |
| 2801 | 113 | cytoplasm | ferredoxin (fdx-1) or ferredoxin, 2Fe—2S type fdx-2 |
| 2807 | 266 | inner 1 | modification methylase (hindIIIM) |
| 2811 | 350 | cytoplasm | asparaginyl-tRNA synthetase (asnS) or aspartyl-tRNA synthetase aspS |
| 2812 | 31 | cytoplasm | riboflavin synthase, beta chain (ribH) |
| 2813 | 228 | inner 3 | PqiA family protein |
| 2814 | 282 | inner 1 | pqiB protein pqiB |
| 2815 | 112 | cytoplasm | asparaginyl-tRNA synthetase (asnS) or aspartyl-tRNA synthetase aspS |
| 2817 | 128 | cytoplasm | carbonic anhydrase |
| 2818 | 122 | cytoplasm | transcriptional regulatory protein (tyrR) |
| 2825 | 215 | cytoplasm | pqiB protein pqiB |
| 2827 | 194 | cytoplasm | phosphoheptose isomerase gmhA |
| 2831 | 233 | cytoplasm | 28 kDa outer membrane protein (hlpA) |
| 2832 | 33 | cytoplasm | glycerol-3-phosphate regulon repressor (glpR) |

REFERENCES

The Contents of which are Hereby Incorporated by Reference

[1] Fleischmann et al. (1995) *Science* 269:496-512.
[2] Li et al. (2003) *Mol Microbiol* 47:1101-1111.
[3] GenBank accession NC_000907.
[4] Geysen et al. (1984) *PNAS USA* 81:3998-4002.
[5] Carter (1994) *Methods Mol Biol* 36:207-23.
[6] Jameson, B A et al. 1988, *CABIOS* 4(1):181-186.
[7] Raddrizzani & Hammer (2000) *Brief Bioinform* 1(2):179-89.
[8] De Lalla et al. (1999) *J. Immunol.* 163:1725-29.
[9] Brusic et al. (1998) *Bioinformatics* 14(2):121-30
[10] Meister et al. (1995) *Vaccine* 13(6):581-91.
[11] Roberts et al. (1996) *AIDS Res Hum Retroviruses* 12(7): 593-610.
[12] Maksyutov & Zagrebelnaya (1993) *Comput Appl Biosci* 9(3):291-7.
[13] Feller & de la Cruz (1991) *Nature* 349(6311):720-1.
[14] Hopp (1993) *Peptide Research* 6:183-190.
[15] Welling et al. (1985) *FEBS Lett.* 188:215-218.
[16] Davenport et al. (1995) *Immunogenetics* 42:392-297.
[17] Bodanszky (1993) *Principles of Peptide Synthesis* (ISBN: 0387564314).
[18] Fields et al. (1997) *Meth Enzymol* 289: *Solid-Phase Peptide Synthesis.* ISBN: 0121821900.
[19] Chan & White (2000) *Fmoc Solid Phase Peptide Synthesis.* ISBN: 0199637245.

[20] Kullmann (1987) *Enzymatic Peptide Synthesis*. ISBN: 0849368413.
[21] Ibba (1996) *Biotechnol Genet Eng Rev* 13:197-216.
[22] Breedveld (2000) *Lancet* 355(9205):735-740.
[23] Gorman & Clark (1990) *Semin. Immunol.* 2:457-466.
[24] Sambrook et al. (1989) *Molecular Cloning: A Laboratory Manual*.
[25] *Short protocols in molecular biology* (4th ed, 1999) Ausubel et al. eds. ISBN 0-471-32938-X.
[26] U.S. Pat. No. 5,707,829
[27] *Current Protocols in Molecular Biology* (F. M. Ausubel et al. eds., 1987) Supplement 30.
[28] EP-B-0509612.
[29] EP-B-0505012.
[30] Yadav et al. (2003) *Lett Appl Microbiol* 37(3):190-5.
[31] Singhi et al. (2002) *Ann Trop Paediatr* 22(4):347-53.
[32] Tang et al. (1997) *Clin. Chem.* 43:2021-2038.
[33] *Vaccine Design* . . . (1995) eds. Powell & Newman. ISBN: 030644867X. Plenum.
[34] WO00/23105.
[35] WO90/14837.
[36] U.S. Pat. No. 5,057,540.
[37] WO96/33739.
[38] EP-A-0109942.
[39] WO96/11711.
[40] WO00/07621.
[41] Barr et al. (1998) *Advanced Drug Delivery Reviews* 32:247-271.
[42] Sjolanderet et al. (1998) *Advanced Drug Delivery Reviews* 32:321-338.
[43] Niikura et al. (2002) *Virology* 293:273-280.
[44] Lenz et al. (2001) *J Immunol* 166:5346-5355.
[45] Pinto et al. (2003) *J Infect Dis* 188:327-338.
[46] Gerber et al. (2001) *Virol* 75:4752-4760.
[47] WO03/024480
[48] WO03/024481
[49] Gluck et al. (2002) *Vaccine* 20:B10-B16.
[50] EP-A-0689454.
[51] Johnson et al. (1999) *Bioorg Med Chem Lett* 9:2273-2278.
[52] Evans et al. (2003) *Expert Rev Vaccines* 2:219-229.
[53] Meraldi et al. (2003) *Vaccine* 21:2485-2491.
[54] Pajak et al. (2003) *Vaccine* 21:836-842.
[55] Kandimalla et al. (2003) *Nucleic Acids Research* 31:2393-2400.
[56] WO02/26757.
[57] WO99/62923.
[58] Krieg (2003) *Nature Medicine* 9:831-835.
[59] McCluskie et al. (2002) *FEMS Immunology and Medical Microbiology* 32:179-185.
[60] WO98/40100.
[61] U.S. Pat. No. 6,207,646.
[62] U.S. Pat. No. 6,239,116.
[63] U.S. Pat. No. 6,429,199.
[64] Kandimalla et al. (2003) *Biochemical Society Transactions* 31 (part 3):654-658.
[65] Blackwell et al. (2003) *J Immunol* 170:4061-4068.
[66] Krieg (2002) *Trends Immunol* 23:64-65.
[67] WO01/95935.
[68] Kandimalla et al. (2003) *BBRC* 306:948-953.
[69] Bhagat et al. (2003) *BBRC* 300:853-861.
[70] WO03/035836.
[71] WO95/17211.
[72] WO98/42375.
[73] Beignon et al. (2002) *Infect Immun* 70:3012-3019.
[74] Pizza et al. (2001) *Vaccine* 19:2534-2541.
[75] Pizza et al. (2000) *Int J Med Microbiol* 290:455-461.
[76] Scharton-Kersten et al. (2000) *Infect Immun* 68:5306-5313.
[77] Ryan et al. (1999) *Infect Immun* 67:6270-6280.
[78] Partidos et al. (1999) *Immunol Lett* 67:209-216.
[79] Peppoloni et al. (2003) *Expert Rev Vaccines* 2:285-293.
[80] Pine et al. (2002) *J Control Release* 85:263-270.
[81] Domenighini et al. (1995) *Mol Microbiol* 15:1165-1167.
[82] WO99/40936.
[83] WO99/44636.
[84] Singh et al] (2001) *J Cont Release* 70:267-276.
[85] WO99/27960.
[86] U.S. Pat. No. 6,090,406.
[87] U.S. Pat. No. 5,916,588.
[88] EP-A-0626169.
[89] WO99/52549.
[90] WO01/21207.
[91] WO01/21152.
[92] Andrianov et al. (1998) *Biomaterials* 19:109-115.
[93] Payne et al. (1998) *Adv Drug Delivery Review* 31:185-196.
[94] Stanley (2002) *Clin Exp Dermatol* 27:571-577.
[95] Jones (2003) *Curr Opin Investig Drugs* 4:214-218.
[96] WO99/11241.
[97] WO94/00153.
[98] WO98/57659.
[99] European patent applications 0835318, 0735898 and 0761231.
[100] WO03/009869.
[101] Almeida & Alpar (1996) *J. Drug Targeting* 3:455-467.
[102] Agarwal & Mishra (1999) *Indian J Exp Biol* 37:6-16.
[103] Costantino et al. (1992) *Vaccine* 10:691-698.
[104] Costantino et al. (1999) *Vaccine* 17:1251-1263.
[105] WO03/007985.
[106] Watson (2000) *Pediatr Infect Dis J* 19:331-332.
[107] Rubin (2000) *Pediatr Clin North Am* 47:269-285, v.
[108] Jedrzejas (2001) *Microbiol Mol Biol Rev* 65:187-207.
[109] Bell (2000) *Pediatr Infect Dis J* 19:1187-1188.
[110] Iwarson (1995) *APMIS* 103:321-326.
[111] Gerlich et al. (1990) *Vaccine* 8 Suppl:S63-68 & 79-80.
[112] *Vaccines* (1988) eds. Plotkin & Mortimer. ISBN 0-7216-1946-0.
[113] Del Guidice et al. (1998) *Molecular Aspects of Medicine* 19:1-70.
[114] Gustafsson et al. (1996) *N. Engl. J. Med.* 334:349-355.
[115] Rappuoli et al. (1991) *TIBTECH* 9:232-238.
[116] Sutter et al. (2000) *Pediatr Clin North Am* 47:287-308.
[117] Zimmerman & Spann (1999) *Am Fam Physician* 59:113-118, 125-126.
[118] McMichael (2000) *Vaccine* 19 Suppl 1:S101-107.
[119] Schuchat (1999) *Lancet* 353(9146):51-6.
[120] WO02/34771.
[121] Dale (1999) *Infect Dis Clin North Am* 13:227-43, viii.
[122] Ferretti et al. (2001) *PNAS USA* 98: 4658-4663.
[123] Kuroda et al. (2001) *Lancet* 357(9264):1225-1240; see also pages 1218-1219.
[124] EP-A-0372501
[125] EP-A-0378881
[126] EP-A-0427347
[127] WO93/17712
[128] WO94/03208
[129] WO98/58668
[130] EP-A-0471177
[131] WO00/56360
[132] WO91/01146
[133] WO00/61761
[134] WO01/72337
[135] *Research Disclosure*, 453077 (January 2002)

[136] Needleman & Wunsch (1970) *J. Mol. Biol.* 48, 443-453.
[137] Rice et al. (2000) *Trends Genet.* 16:276-277.
[138] Gennaro (2000) *Remington: The Science and Practice of Pharmacy.* 20th edition, ISBN: 0683306472.
[139] *Methods In Enzymology* (S. Colowick and N. Kaplan, eds., Academic Press, Inc.)
[140] *Handbook of Experimental Immunology*, Vols. I-IV (D. M. Weir and C. C. Blackwell, eds., 1986, Blackwell Scientific Publications)
[141] Sambrook, et al., *Molecular Cloning: A Laboratory Manual* (2nd Edition, 1989).
[142] *Handbook of Surface and Colloidal Chemistry* (Birdi, K. S. ed., CRC Press, 1997)
[143] *Short Protocols in Molecular Biology,* 4th ed. (Ausubel et al. eds., 1999, John Wiley & Sons)
[144] *Molecular Biology Techniques: An Intensive Laboratory Course,* (Ream et al., eds., 1998, Academic Press)
[145] *PCR (Introduction to Biotechniques Series),* 2nd ed. (Newton & Graham eds., 1997, Springer Verlag)
[146] Mason et al. (2003) *Infect Immun* 71:3454-3462.
[147] Erdile et al. (1993) *Infect Immun* 61:81-90.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09102729B2). An electronic copy of the "Sequence Listing" will also be available from the USPTO upon request and payment of the fee set forth in 37 CFR 1.19(b)(3).

The invention claimed is:

1. An immunogenic composition comprising an effective amount of (a) an isolated, immunogenic polypeptide, wherein the polypeptide comprises the amino acid sequence of SEQ ID NO: 1842 from *Haemophilus influenzae* strain 86-028NP, or the amino acid sequence of SEQ ID NO: 1842 that lacks a signal sequence; (b) a pharmaceutically acceptable carrier, and (c) an adjuvant.

2. The composition of claim 1, wherein the polypeptide comprises the amino acid sequence of SEQ ID NO:1842.

3. An immunogenic comprising an effective amount of (a) an isolated polypeptide that comprises an amino acid sequence with at least 95% sequence identity to the amino acid sequence of SEQ ID NO: 1842; (b) a pharmaceutically acceptable carrier, and (c) an adjuvant.

4. The composition of claim 1, wherein the adjuvant comprises an aluminium salt.

5. The composition of claim 2, wherein the adjuvant comprises an aluminium salt.

6. The composition of claim 3, wherein the adjuvant comprises an aluminium salt.

7. The composition of claim 1, wherein the adjuvant is an oil emulsion.

8. The composition of claim 2, wherein the adjuvant is an oil emulsion.

9. The composition of claim 3, wherein the adjuvant is an oil emulsion.

10. The composition of claim 7, wherein the adjuvant is MF59.

11. The composition of claim 8, wherein the adjuvant is MF59.

12. The composition of claim 9, wherein the adjuvant is MF59.

13. The composition of claim 7, wherein the adjuvant is Complete Freund's adjuvant or Incomplete Freund's adjuvant.

14. The composition of claim 8, wherein the adjuvant is Complete Freund's adjuvant or Incomplete Freund's adjuvant.

15. The composition of claim 9, wherein the adjuvant is Complete Freund's adjuvant or Incomplete Freund's adjuvant.

* * * * *